US012744124B2

(12) United States Patent
Hytopoulos et al.

(10) Patent No.: US 12,744,124 B2
(45) Date of Patent: Sep. 22, 2026

(54) CARDIAC ARRHYTHMIA DETECTION

(71) Applicant: iRhythm Technologies, Inc., San Francisco, CA (US)

(72) Inventors: Evangelos Hytopoulos, San Mateo, CA (US); Justin Cambra, Oakland, CA (US)

(73) Assignee: iRhythm Technologies, Inc., San Francisco, CA (US)

( * ) Notice: Subject to any disclaimer, the term of this patent is extended or adjusted under 35 U.S.C. 154(b) by 76 days.

(21) Appl. No.: 18/732,380

(22) Filed: Jun. 3, 2024

(65) Prior Publication Data

US 2024/0321455 A1 Sep. 26, 2024

Related U.S. Application Data

(63) Continuation of application No. PCT/US2022/081409, filed on Dec. 13, 2022.

(Continued)

(51) Int. Cl.
*G16H 50/20* (2018.01)
*G16H 10/60* (2018.01)
(Continued)

(52) U.S. Cl.
CPC ............. *G16H 50/20* (2018.01); *G16H 10/60* (2018.01); *G16H 50/30* (2018.01); *G16H 50/70* (2018.01)

(58) Field of Classification Search
CPC ........ G16H 50/30; G16H 40/67; G16H 50/20; G16H 10/60; G16H 50/70; A61B 5/257;
(Continued)

(56) References Cited

U.S. PATENT DOCUMENTS 1,497,079 A 6/1924 Gullborg
2,179,922 A 11/1939 Dana
(Continued)

FOREIGN PATENT DOCUMENTS

AU 2011252998 8/2015
AU 2014209376 6/2017
(Continued)

OTHER PUBLICATIONS

US 8,750,980 B2, 06/2014, Katra et al. (withdrawn)
(Continued)

*Primary Examiner* — Igor N Borissov
(74) *Attorney, Agent, or Firm* — Knobbe, Martens, Olson & Bear, LLP

(57) ABSTRACT

The present disclosure relates to a non-invasive cardiac monitoring device that records cardiac data to infer onset physiological characteristics of a human, such as an onset condition for cardiac arrhythmia, and recommend treatments/interventions. Some implementations include clustering historical patient data to determine efficacy of treatments based on the patient data and corresponding cluster groups. Further implementations allow for processing of the detected cardiac rhythm signals partially on the wearable cardiac monitor device, and partially on a remote computing system. Some implementations include a wearable cardiac monitor device for long-term adhesion to a patient for prolonged detection of cardiac rhythm signals.

15 Claims, 34 Drawing Sheets

Related U.S. Application Data

(60) Provisional application No. 63/265,335, filed on Dec. 13, 2021.

(51) Int. Cl.
*G16H 50/30* (2018.01)
*G16H 50/70* (2018.01)

(58) Field of Classification Search
CPC ....... A61B 5/7267; A61B 5/363; A61B 5/361; A61B 5/02455; A61B 5/7203; A61B 2562/164; A61B 2560/0462; A61B 2560/0412; A61B 2562/0209
USPC .............................................................. 705/3
See application file for complete search history.

(56) References Cited

U.S. PATENT DOCUMENTS 2,201,645 A 5/1940 Epner
2,311,060 A 2/1943 Lurrain
2,444,552 A 7/1948 Sigurd
2,500,840 A 3/1950 Lyons
3,215,136 A 11/1965 Holter et al.
3,547,107 A 12/1970 Chapman et al.
3,697,706 A 10/1972 Huggard
3,870,034 A 3/1975 James
3,882,853 A 5/1975 Gofman
3,911,906 A 10/1975 Reinhold
4,023,312 A 5/1977 Stickney
4,027,664 A 6/1977 Heavner, Jr. et al.
4,082,087 A 4/1978 Howson
4,121,573 A 10/1978 Crovella et al.
4,123,785 A 10/1978 Cherry et al.
4,126,126 A 11/1978 Bare
4,202,139 A 5/1980 Hong et al.
4,274,419 A 6/1981 Tam et al.
4,274,420 A 6/1981 Hymes
4,280,507 A 7/1981 Rosenberg
4,286,610 A 9/1981 Jones
4,333,475 A 6/1982 Moreno et al.
4,361,990 A 12/1982 Link
4,381,792 A 5/1983 Busch
4,438,767 A 3/1984 Nelson
4,459,987 A 7/1984 Pangburn
4,535,783 A 8/1985 Marangoni
4,537,207 A 8/1985 Gilhaus
4,572,187 A 2/1986 Schetrumpf
4,621,465 A 11/1986 Pangburn
4,622,979 A 11/1986 Katchis et al.
4,623,206 A 11/1986 Fuller
4,658,826 A 4/1987 Weaver
4,712,552 A 12/1987 Pangburn
4,736,752 A 4/1988 Munck et al.
4,763,660 A 8/1988 Kroll et al.
4,795,516 A 1/1989 Strand
4,855,294 A 8/1989 Patel
4,925,453 A 5/1990 Kannankeril
4,938,228 A 7/1990 Righter et al.
4,981,141 A 1/1991 Segalowitz
5,003,987 A 4/1991 Grinwald
5,027,824 A 7/1991 Dougherty et al.
5,082,851 A 1/1992 Appelbaum et al.
5,086,778 A 2/1992 Mueller et al.
5,191,891 A 3/1993 Righter
5,205,295 A 4/1993 Del Mar et al.
5,226,425 A 7/1993 Righter
5,228,450 A 7/1993 Sellers
5,230,119 A 7/1993 Woods et al.
5,289,824 A 3/1994 Mills et al.
5,305,746 A 4/1994 Fendrock
5,309,909 A 5/1994 Gadsby
5,328,935 A 7/1994 Van Phan
5,365,935 A 11/1994 Righter et al.
5,458,141 A 10/1995 Neil
5,483,967 A 1/1996 Ohtake
5,489,624 A 2/1996 Kantner et al.
5,511,548 A 4/1996 Riazzi et al.
5,511,553 A 4/1996 Segalowitz
5,515,858 A 5/1996 Myllymaki
5,536,768 A 7/1996 Kantner et al.
5,581,369 A 12/1996 Righter et al.
5,626,140 A 5/1997 Feldman et al.
5,634,468 A 6/1997 Platt et al.
5,645,063 A 7/1997 Straka
5,645,068 A 7/1997 Mezack et al.
5,730,143 A 3/1998 Schwarzberg
5,738,104 A 4/1998 Lo et al.
5,749,365 A 5/1998 Magill
5,749,367 A 5/1998 Gamlyn et al.
5,771,524 A 6/1998 Woods et al.
5,772,604 A 6/1998 Langberg et al.
5,776,072 A 7/1998 Hsu et al.
5,881,743 A 3/1999 Nadel
D408,541 S 4/1999 Dunshee et al.
5,916,239 A 6/1999 Geddes et al.
5,931,791 A 8/1999 Saltzstein et al.
5,941,829 A 8/1999 Saltzstein et al.
5,957,854 A 9/1999 Besson et al.
5,959,529 A 9/1999 Kail
6,013,007 A 1/2000 Root et al.
6,032,060 A 2/2000 Carim
6,038,464 A 3/2000 Axelgaard et al.
6,038,469 A 3/2000 Karlsson et al.
6,044,515 A 4/2000 Zygmont
6,093,146 A 7/2000 Filangeri
D429,336 S 8/2000 Francis et al.
6,102,856 A 8/2000 Groff et al.
6,117,077 A 9/2000 Del Mar et al.
6,121,508 A 9/2000 Bischof
6,132,371 A 10/2000 Dempsey et al.
6,134,480 A 10/2000 Minogue
6,136,008 A 10/2000 Becker et al.
6,161,036 A 12/2000 Matsumura et al.
6,169,915 B1 1/2001 Krumbiegel et al.
6,178,357 B1 1/2001 Gliner et al.
6,200,265 B1 3/2001 Walsh et al.
6,223,080 B1 4/2001 Thompson
6,225,901 B1 5/2001 Kail
6,232,366 B1 5/2001 Wang et al.
6,238,338 B1 5/2001 DeLuca et al.
6,248,115 B1 6/2001 Halk
6,287,252 B1 9/2001 Lugo
6,290,707 B1 9/2001 Street
6,315,719 B1 11/2001 Rode et al.
6,379,237 B1 4/2002 Gordon
6,385,473 B1 5/2002 Haines et al.
6,389,308 B1 5/2002 Shusterman
6,416,471 B1 7/2002 Kumar et al.
6,434,410 B1 8/2002 Cordero et al.
6,441,747 B1 8/2002 Khair et al.
6,453,186 B1 9/2002 Lovejoy et al.
6,454,708 B1 9/2002 Ferguson et al.
6,456,871 B1 9/2002 Hsu et al.
6,456,872 B1 9/2002 Faisandier
6,464,815 B1 10/2002 Beaudry
6,493,898 B1 12/2002 Woods et al.
6,496,705 B1 12/2002 Ng et al.
6,510,339 B2 1/2003 Kovtun et al.
6,546,285 B1 4/2003 Owen et al.
6,564,090 B2 5/2003 Taha et al.
6,569,095 B2 5/2003 Eggers
6,577,893 B1 6/2003 Besson et al.
6,580,942 B1 6/2003 Willshire
6,585,707 B2 7/2003 Cabiri et al.
6,589,170 B1 7/2003 Flach et al.
6,589,187 B1 7/2003 Dimberger et al.
6,605,046 B1 8/2003 Del Mar et al.
6,615,083 B2 9/2003 Kupper
6,622,035 B1 9/2003 Merilainen
6,626,865 B1 9/2003 Prisell
6,656,125 B2 12/2003 Misczynski et al.
6,664,893 B1 12/2003 Eveland et al.
6,665,385 B2 12/2003 Rogers et al.

(56) References Cited

U.S. PATENT DOCUMENTS 6,690,959 B2 2/2004 Thompson
6,694,177 B2 2/2004 Eggers et al.
6,701,184 B2 3/2004 Henkin
6,711,427 B1 3/2004 Ketelhohn
6,730,028 B2 5/2004 Eppstein
D492,607 S 7/2004 Curkovic et al.
6,773,396 B2 8/2004 Flach et al.
6,775,566 B2 8/2004 Nissila
6,801,137 B2 10/2004 Eggers
6,801,802 B2 10/2004 Sitzman et al.
6,871,089 B2 3/2005 Korzinov et al.
6,871,211 B2 3/2005 Labounty et al.
6,875,174 B2 4/2005 Braun et al.
6,881,191 B2 4/2005 Oakley et al.
6,893,396 B2 5/2005 Schulze et al.
6,897,788 B2 5/2005 Khair et al.
6,904,312 B2 6/2005 Bardy
6,925,324 B2 8/2005 Shusterman
6,940,403 B2 9/2005 Kail
6,954,163 B2 10/2005 Toumazou et al.
6,957,107 B2 10/2005 Rogers et al.
6,987,965 B2 1/2006 Ng et al.
7,002,468 B2 2/2006 Eveland et al.
7,020,508 B2 3/2006 Stivoric et al.
7,024,248 B2 4/2006 Penner et al.
7,031,770 B2 4/2006 Collins et al.
7,072,708 B1 7/2006 Andresen et al.
7,072,709 B2 7/2006 Xue
7,076,283 B2 7/2006 Cho et al.
7,076,287 B2 7/2006 Rowlandson
7,076,288 B2 7/2006 Skinner
7,076,289 B2 7/2006 Sarkar et al.
7,079,977 B2 7/2006 Osorio et al.
7,082,327 B2 7/2006 Houben
7,089,048 B2 8/2006 Matsumura et al.
7,099,715 B2 8/2006 Korzinov et al.
7,117,031 B2 10/2006 Lohman et al.
7,120,485 B2 10/2006 Glass et al.
7,130,396 B2 10/2006 Rogers et al.
7,161,484 B2 1/2007 Tsoukalis
7,171,166 B2 1/2007 Ng et al.
7,179,152 B1 2/2007 Rhoades
7,186,264 B2 3/2007 Liddicoat et al.
7,193,264 B2 3/2007 Lande
7,194,300 B2 3/2007 Korzinov
7,206,630 B1 4/2007 Tarler
7,212,850 B2 5/2007 Prystowsky et al.
7,222,054 B2 5/2007 Geva
7,242,318 B2 7/2007 Harris
7,266,361 B2 9/2007 Burdett
7,316,671 B2 1/2008 Lastovich et al.
7,349,947 B1 3/2008 Slage et al.
D567,949 S 4/2008 Lash et al.
7,354,423 B2 4/2008 Zelickson et al.
7,387,607 B2 6/2008 Holt et al.
7,444,177 B2 10/2008 Nazeri
D584,414 S 1/2009 Lash et al.
7,477,933 B2 1/2009 Ueyama
7,478,108 B2 1/2009 Townsend et al.
7,481,772 B2 1/2009 Banet
7,482,314 B2 1/2009 Grimes et al.
7,502,643 B2 3/2009 Farringdon et al.
7,539,533 B2 5/2009 Tran
7,542,878 B2 6/2009 Nanikashvili
D600,351 S 9/2009 Phillips et al.
7,587,237 B2 9/2009 Korzinov et al.
7,630,756 B2 12/2009 Linker
7,632,174 B2 12/2009 Gringer et al.
D607,570 S 1/2010 Phillips et al.
7,672,714 B2 3/2010 Kuo et al.
7,715,905 B2 5/2010 Kurzweil et al.
D618,357 S 6/2010 Navies
7,729,753 B2 6/2010 Kremliovsky et al.
7,733,224 B2 6/2010 Tran
D621,048 S 8/2010 Severe et al.
7,815,494 B2 10/2010 Gringer et al.
7,841,039 B1 11/2010 Squire
7,889,070 B2 2/2011 Reeves et al.
7,894,888 B2 2/2011 Chan et al.
D634,431 S 3/2011 Severe et al.
7,904,133 B2 3/2011 Gehman et al.
7,907,956 B2 3/2011 Uhlik
7,907,996 B2 3/2011 Prystowsky et al.
7,941,207 B2 5/2011 Korzinov
D639,437 S 6/2011 Bishay et al.
7,970,450 B2 6/2011 Kroecker et al.
7,979,111 B2 7/2011 Acquista
7,996,075 B2 8/2011 Korzinov et al.
7,996,187 B2 8/2011 Nanikashvili et al.
8,002,701 B2 8/2011 John et al.
D645,968 S 9/2011 Kasabach et al.
D650,911 S 12/2011 Odeh
8,077,042 B2 12/2011 Peeters
8,103,333 B2 1/2012 Tran
8,108,036 B2 1/2012 Tran
8,116,841 B2 2/2012 Bly et al.
8,150,502 B2 4/2012 Kumar et al.
8,156,945 B2 4/2012 Hart
8,160,682 B2 4/2012 Kumar et al.
D659,836 S 5/2012 Bensch et al.
8,170,639 B2 5/2012 Hauge
8,200,319 B2 6/2012 Pu et al.
8,200,320 B2 6/2012 Kovacs
D663,432 S 7/2012 Nichols
8,214,007 B2 7/2012 Baker et al.
8,244,335 B2 8/2012 Kumar et al.
8,249,686 B2 8/2012 Libbus et al.
8,261,754 B2 9/2012 Pitstick
8,265,907 B2 9/2012 Nanikashvili et al.
RE43,767 E 10/2012 Eggers et al.
8,280,749 B2 10/2012 Hsieh et al.
8,285,356 B2 10/2012 Bly et al.
8,290,129 B2 10/2012 Rogers et al.
8,290,574 B2 10/2012 Field et al.
8,301,219 B2 10/2012 Chen et al.
8,301,236 B2 10/2012 Baumann et al.
8,311,604 B2 11/2012 Rowlandson et al.
8,315,687 B2 11/2012 Cross et al.
8,315,695 B2 11/2012 Sebelius et al.
8,323,188 B2 12/2012 Tran
8,326,394 B2 12/2012 Rowlandson et al.
8,326,407 B2 12/2012 Linker
8,328,718 B2 12/2012 Tran
D674,009 S 1/2013 Nichols
8,343,116 B2 1/2013 Ignon
8,369,936 B2 2/2013 Farringdon et al.
8,374,688 B2 2/2013 Libbus et al.
8,386,009 B2 2/2013 Lindberg et al.
8,388,543 B2 3/2013 Chon et al.
8,406,843 B2 3/2013 Tiegs et al.
8,412,317 B2 4/2013 Mazar
8,417,326 B2 4/2013 Chon et al.
8,425,414 B2 4/2013 Eveland
D682,437 S 5/2013 Olson et al.
8,449,471 B2 5/2013 Tran
8,452,356 B2 5/2013 Vestel et al.
8,460,189 B2 6/2013 Libbus et al.
8,473,039 B2 6/2013 Michelson et al.
8,473,047 B2 6/2013 Chakravarthy et al.
8,478,418 B2 7/2013 Fahey
8,483,809 B2 7/2013 Kim et al.
8,500,636 B2 8/2013 Tran
8,515,529 B2 8/2013 Pu et al.
8,525,673 B2 9/2013 Tran
8,535,223 B2 9/2013 Corroy et al.
8,538,503 B2 9/2013 Kumar et al.
8,540,731 B2 9/2013 Kay
8,560,046 B2 10/2013 Kumar et al.
8,562,527 B2 10/2013 Braun et al.
8,571,645 B2 10/2013 Wu et al.
8,588,908 B2 11/2013 Moorman et al.
8,591,430 B2 11/2013 Amurthur et al.
8,591,599 B1 11/2013 Kaliki
8,594,763 B1 11/2013 Bibian

(56) References Cited

U.S. PATENT DOCUMENTS 8,626,262 B2 1/2014 McGusty et al.
8,630,699 B2 1/2014 Baker et al.
8,639,319 B2 1/2014 Hugh et al.
8,668,643 B2 3/2014 Kinast
8,684,900 B2 4/2014 Tran
8,684,925 B2 4/2014 Amurthur et al.
8,688,189 B2 4/2014 Shennib
8,688,190 B2 4/2014 Libbus et al.
8,688,202 B2 4/2014 Brockway et al.
8,718,742 B2 5/2014 Beck et al.
8,718,752 B2 5/2014 Libbus et al.
8,718,753 B2 5/2014 Chon et al.
8,731,632 B1 5/2014 Sereboff et al.
8,738,118 B2 5/2014 Moon et al.
8,744,561 B2 6/2014 Fahey
8,755,876 B2 6/2014 Chon et al.
8,782,308 B2 7/2014 Vlach
8,789,727 B2 7/2014 Mortazavi
8,790,257 B2 7/2014 Libbus et al.
8,795,174 B2 8/2014 Manicka et al.
8,818,481 B2 8/2014 Bly et al.
8,823,490 B2 9/2014 Libbus et al.
8,838,218 B2 9/2014 Khair
8,858,450 B2 10/2014 Chon et al.
8,874,185 B2 10/2014 Sonnenborg
D719,267 S 12/2014 Vaccarella
8,903,477 B2 12/2014 Berkner
8,903,484 B2 12/2014 Mazar
8,909,328 B2 12/2014 Chon
8,909,330 B2 12/2014 McCombie et al.
8,909,332 B2 12/2014 Vitali et al.
8,909,333 B2 12/2014 Rossi
8,909,832 B2 12/2014 Vlach et al.
8,926,509 B2 1/2015 Magar et al.
8,945,019 B2 2/2015 Prystowsky et al.
8,948,854 B2 2/2015 Friedman et al.
8,954,129 B1 2/2015 Schlegel et al.
8,956,293 B2 2/2015 McCombie et al.
8,968,195 B2 3/2015 Tran
8,972,000 B2 3/2015 Manera
8,979,755 B2 3/2015 Szydlo-Moore et al.
9,014,777 B2 4/2015 Woo
9,015,008 B2 4/2015 Geva et al.
9,017,255 B2 4/2015 Raptis et al.
9,017,256 B2 4/2015 Gottesman
9,021,161 B2 4/2015 Vlach et al.
9,021,165 B2 4/2015 Vlach
9,026,190 B2 5/2015 Shenasa et al.
9,037,223 B2 5/2015 Oral et al.
9,044,148 B2 6/2015 Michelson et al.
9,084,548 B2 7/2015 Bouguerra
9,095,274 B2 8/2015 Fein et al.
9,101,264 B2 8/2015 Acquista
9,138,144 B2 9/2015 Geva
9,149,228 B2 10/2015 Kinast
9,173,670 B2 11/2015 Sepulveda et al.
9,179,851 B2 11/2015 Baumann et al.
D744,659 S 12/2015 Bishay et al.
9,211,076 B2 12/2015 Kim
9,226,679 B2 1/2016 Balda
9,241,649 B2 1/2016 Kumar et al.
9,241,650 B2 1/2016 Amirim
9,277,864 B2 3/2016 Yang et al.
9,282,894 B2 3/2016 Banet et al.
9,307,921 B2 4/2016 Friedman et al.
9,345,414 B1 5/2016 Bardy et al.
9,355,215 B2 5/2016 Vlach
D759,653 S 6/2016 Toth et al.
9,357,939 B1 6/2016 Nosrati
9,364,150 B2 6/2016 Sebelius et al.
9,364,155 B2 6/2016 Bardy et al.
9,398,853 B2 7/2016 Nanikashvili
9,408,545 B2 8/2016 Felix et al.
9,408,551 B2 8/2016 Bardy et al.
9,408,576 B2 8/2016 Chon et al.
9,414,753 B2 8/2016 Chon et al.
9,414,786 B1 8/2016 Brockway et al.
D766,447 S 9/2016 Bishay et al.
9,433,367 B2 9/2016 Felix et al.
9,433,380 B1 9/2016 Bishay et al.
9,439,566 B2 9/2016 Arne et al.
9,439,599 B2 9/2016 Thompson et al.
9,445,719 B2 9/2016 Libbus et al.
9,451,890 B2 9/2016 Gitlin et al.
9,451,975 B2 9/2016 Sepulveda et al.
9,474,445 B2 10/2016 Eveland
9,474,461 B2 10/2016 Fisher et al.
9,478,998 B1 10/2016 Lapetina et al.
D773,056 S 11/2016 Vlach
9,492,084 B2 11/2016 Behar et al.
9,504,423 B1 11/2016 Bardy et al.
D775,361 S 12/2016 Vosch et al.
9,510,764 B2 12/2016 Li et al.
9,510,768 B2 12/2016 Rossi
9,526,433 B2 12/2016 Lapetina et al.
9,545,204 B2 1/2017 Bishay et al.
9,545,228 B2 1/2017 Bardy et al.
9,554,715 B2 1/2017 Bardy et al.
9,579,020 B2 2/2017 Libbus et al.
D780,914 S 3/2017 Kyvik et al.
9,585,584 B2 3/2017 Marek et al.
9,597,004 B2 3/2017 Hughes et al.
9,615,763 B2 4/2017 Felix et al.
9,615,793 B2 4/2017 Solosko et al.
9,619,660 B1 4/2017 Felix et al.
9,642,537 B2 5/2017 Felix et al.
9,655,518 B2 5/2017 Lin
9,655,537 B2 5/2017 Bardy et al.
9,655,538 B2 5/2017 Felix
9,662,030 B2 5/2017 Thng et al.
9,675,264 B2 6/2017 Acquista et al.
9,700,227 B2 7/2017 Bishay et al.
9,706,938 B2 7/2017 Chakravarthy et al.
9,706,956 B2 7/2017 Brockway et al.
9,713,428 B2 7/2017 Chon et al.
D793,566 S 8/2017 Bishay et al.
D794,812 S 8/2017 Matsushita
9,717,432 B2 8/2017 Bardy et al.
9,717,433 B2 8/2017 Felix et al.
9,730,593 B2 8/2017 Bardy et al.
9,730,604 B2 8/2017 Li et al.
9,730,641 B2 8/2017 Felix et al.
9,736,625 B1 8/2017 Landgraf et al.
9,737,211 B2 8/2017 Bardy et al.
9,737,224 B2 8/2017 Bardy et al.
D797,301 S 9/2017 Chen
D797,943 S 9/2017 Long
D798,170 S 9/2017 Toth et al.
D798,294 S 9/2017 Toth et al.
9,775,534 B2 10/2017 Korzinov et al.
9,775,536 B2 10/2017 Felix et al.
9,782,095 B2 10/2017 Ylostalo et al.
9,782,132 B2 10/2017 Golda et al.
9,788,722 B2 10/2017 Bardy et al.
9,801,562 B1 10/2017 Host-Madsen
9,820,665 B2 11/2017 Felix et al.
9,839,363 B2 12/2017 Albert
D810,308 S 2/2018 Lind et al.
D811,610 S 2/2018 Abel et al.
D811,611 S 2/2018 Lind et al.
D811,615 S 2/2018 Lind et al.
9,888,866 B2 2/2018 Chon et al.
9,901,274 B2 2/2018 Bishay et al.
9,907,478 B2 3/2018 Friedman et al.
9,936,875 B2 4/2018 Bardy et al.
9,955,885 B2 5/2018 Felix et al.
9,955,887 B2 5/2018 Hughes et al.
9,955,888 B2 5/2018 Felix et al.
9,955,911 B2 5/2018 Bardy et al.
9,968,274 B2 5/2018 Korzinov et al.
9,986,921 B2 6/2018 Chon et al.
10,004,415 B2 6/2018 Bishay et al.
D823,466 S 7/2018 Marogil
D824,526 S 7/2018 Ramjit et al.

(56) References Cited

U.S. PATENT DOCUMENTS 10,045,709 B2 8/2018 Bardy et al.
10,052,022 B2 8/2018 Bardy et al.
10,076,257 B2 9/2018 Lin et al.
10,095,841 B2 10/2018 Dettinger et al.
10,098,559 B2 10/2018 Hughes et al.
10,111,601 B2 10/2018 Bishay et al.
10,123,703 B2 11/2018 Bardy et al.
10,154,793 B2 12/2018 Felix et al.
10,165,946 B2 1/2019 Bardy et al.
10,172,534 B2 1/2019 Felix et al.
10,176,575 B2 1/2019 Isgum et al.
10,251,575 B2 4/2019 Bardy et al.
10,251,576 B2 4/2019 Bardy et al.
10,264,992 B2 4/2019 Felix et al.
10,265,015 B2 4/2019 Bardy et al.
10,270,898 B2 4/2019 Soli et al.
10,271,754 B2 4/2019 Bahney et al.
10,271,755 B2 4/2019 Felix et al.
10,271,756 B2 4/2019 Felix et al.
10,278,603 B2 5/2019 Felix et al.
10,278,606 B2 5/2019 Bishay et al.
10,278,607 B2 5/2019 Prystowsky et al.
10,299,691 B2 5/2019 Hughes et al.
10,321,823 B2 6/2019 Chakravarthy et al.
10,327,657 B2 6/2019 Spencer et al.
D852,965 S 7/2019 Bahney et al.
D854,167 S 7/2019 Bahney et al.
10,362,467 B2 7/2019 Landgraf et al.
10,368,808 B2 8/2019 Lee et al.
10,376,172 B2 8/2019 Kuppuraj et al.
10,390,700 B2 8/2019 Bardy et al.
10,398,344 B2 9/2019 Felix et al.
10,405,799 B2 9/2019 Kumar et al.
10,413,205 B2 9/2019 Bardy et al.
10,426,634 B1 10/2019 Al-Jazaeri et al.
10,433,743 B1 10/2019 Felix et al.
10,433,748 B2 10/2019 Bishay et al.
10,433,751 B2 10/2019 Bardy et al.
10,441,184 B2 10/2019 Baumann et al.
10,463,269 B2 11/2019 Boleyn et al.
10,478,083 B2 11/2019 Felix et al.
10,499,812 B2 12/2019 Bardy et al.
10,517,500 B2 12/2019 Kumar et al.
10,555,683 B2 2/2020 Bahney et al.
10,561,326 B2 2/2020 Felix et al.
10,561,328 B2 2/2020 Bishay
10,568,533 B2 2/2020 Soli et al.
10,588,527 B2 3/2020 McNamara et al.
10,595,371 B2 3/2020 Gopalakrishnan et al.
10,602,942 B2 3/2020 Shakur et al.
10,602,977 B2 3/2020 Bardy et al.
10,624,551 B2 4/2020 Bardy et al.
10,660,520 B2 5/2020 Lin
10,667,712 B2 6/2020 Park et al.
10,729,361 B2 8/2020 Hoppe et al.
10,758,139 B2 9/2020 Rapin et al.
10,772,521 B2 9/2020 Korzinov et al.
10,779,744 B2 9/2020 Rapin et al.
10,813,565 B2 10/2020 Park et al.
10,827,938 B2 11/2020 Fontanarava et al.
10,866,619 B1 12/2020 Bushnell et al.
10,869,610 B2 12/2020 Lu et al.
10,987,018 B2 4/2021 Aga et al.
11,004,198 B2 5/2021 Isgum et al.
11,017,887 B2 5/2021 Finkelmeier et al.
11,026,632 B2 6/2021 Narasimhan et al.
11,051,738 B2 7/2021 Bahney et al.
11,051,743 B2 7/2021 Felix et al.
11,062,804 B2 7/2021 Selvaraj et al.
11,083,371 B1 8/2021 Szabados et al.
11,141,091 B2 10/2021 Uday et al.
11,172,882 B2 11/2021 Upadhya et al.
11,246,523 B1 2/2022 Abercrombie, II et al.
11,246,524 B2 2/2022 Szabados et al.
11,253,185 B2 2/2022 Szabados et al.
11,253,186 B2 2/2022 Szabados et al.
11,276,491 B2 3/2022 Petterson et al.
11,289,197 B1 3/2022 Park et al.
11,324,420 B2 5/2022 Selvaraj et al.
11,324,441 B2 5/2022 Bardy et al.
11,331,034 B2 5/2022 Rapin et al.
11,337,632 B2 5/2022 Abercrombie, II et al.
11,350,864 B2 6/2022 Abercrombie, II et al.
11,350,865 B2 6/2022 Abercrombie, II et al.
11,375,941 B2 7/2022 Szabados et al.
11,382,555 B2 7/2022 Szabados et al.
11,399,760 B2 8/2022 Abercrombie, II et al.
11,445,967 B2 9/2022 Felix et al.
11,497,432 B2 11/2022 Szabados et al.
11,504,041 B2 11/2022 Abercrombie, II et al.
11,589,792 B1 2/2023 Abercrombie, II et al.
11,605,458 B2 3/2023 Park et al.
11,627,902 B2 4/2023 Bahney et al.
11,660,037 B2 5/2023 Felix et al.
D988,518 S 6/2023 Levy et al.
11,678,832 B2 6/2023 Boleyn et al.
11,751,789 B2 9/2023 Abercrombie, II et al.
11,756,684 B2 9/2023 Park et al.
11,806,150 B2 11/2023 Abercrombie, II et al.
D1,012,295 S 1/2024 Peremen et al.
11,925,469 B2 3/2024 Szabados et al.
12,133,731 B2 11/2024 Abercrombie, II et al.
12,133,734 B2 11/2024 Kumar et al.
12,213,791 B2 2/2025 Abercrombie, II et al.
12,245,859 B2 3/2025 Bahney et al.
12,245,860 B2 3/2025 Bahney et al.
12,274,554 B2 4/2025 Kumar et al.
12,285,261 B2 4/2025 Bishay et al.
12,303,275 B2 5/2025 Bahney et al.
12,303,277 B2 5/2025 Kumar et al.
12,310,735 B2 5/2025 Felix et al.
12,324,668 B2 6/2025 Kumar et al.
12,357,212 B2 7/2025 Bahney et al.
12,402,819 B1 9/2025 Bahney et al.
12,408,856 B1 9/2025 Kumar et al.
12,582,339 B2 3/2026 Abercrombie, II et al.
2001/0056262 A1 12/2001 Cabiri et al.
2002/0007126 A1 1/2002 Nissila
2002/0026112 A1 2/2002 Nissila et al.
2002/0067256 A1 6/2002 Kail
2002/0082491 A1 6/2002 Nissila
2002/0087167 A1 7/2002 Winitsky
2002/0180605 A1 12/2002 Ozguz et al.
2003/0023178 A1 1/2003 Bischoff et al.
2003/0069510 A1 4/2003 Semler
2003/0083559 A1 5/2003 Thompson
2003/0125786 A1 7/2003 Gliner
2003/0149349 A1 8/2003 Jensen
2003/0176795 A1 9/2003 Harris et al.
2003/0195408 A1 10/2003 Hastings
2003/0199811 A1 10/2003 Sage, Jr. et al.
2003/0212319 A1 11/2003 Magill
2004/0032957 A1 2/2004 Mansy et al.
2004/0068195 A1 4/2004 Massicotte et al.
2004/0077954 A1 4/2004 Oakley et al.
2004/0082843 A1 4/2004 Menon
2004/0187297 A1 9/2004 Su
2004/0199063 A1 10/2004 O'Neil
2004/0215091 A1 10/2004 Lohman et al.
2004/0236202 A1 11/2004 Burton
2004/0238819 A1 12/2004 Maghribi et al.
2004/0254587 A1 12/2004 Park
2004/0260189 A1 12/2004 Eggers et al.
2005/0096513 A1 5/2005 Ozguz et al.
2005/0101875 A1 5/2005 Semler et al.
2005/0118246 A1 6/2005 Wong et al.
2005/0119580 A1 6/2005 Eveland
2005/0165318 A1 7/2005 Brodnick et al.
2005/0165323 A1 7/2005 Montgomery et al.
2005/0204636 A1 9/2005 Azar et al.
2005/0277841 A1 12/2005 Shennib
2005/0280531 A1 12/2005 Fadem et al.
2006/0030781 A1 2/2006 Shennib
2006/0030782 A1 2/2006 Shennib

(56) References Cited

U.S. PATENT DOCUMENTS

2006/0047215 A1 3/2006 Newman et al.
2006/0084883 A1 4/2006 Linker
2006/0142648 A1 6/2006 Banet et al.
2006/0142654 A1 6/2006 Rytky
2006/0149156 A1 7/2006 Cochran et al.
2006/0155173 A1 7/2006 Anttila et al.
2006/0155183 A1 7/2006 Kroecker et al.
2006/0155199 A1 7/2006 Logier et al.
2006/0155200 A1 7/2006 Ng et al.
2006/0161064 A1 7/2006 Watrous et al.
2006/0161065 A1 7/2006 Elion
2006/0161066 A1 7/2006 Elion
2006/0161067 A1 7/2006 Elion
2006/0161068 A1 7/2006 Hastings et al.
2006/0167353 A1 7/2006 Nazeri
2006/0224072 A1 10/2006 Shennib
2006/0264767 A1 11/2006 Shennib
2007/0003695 A1 1/2007 Tregub et al.
2007/0010729 A1 1/2007 Virtanen
2007/0027388 A1 2/2007 Chou
2007/0088419 A1 4/2007 Florina et al.
2007/0156054 A1 7/2007 Korzinov et al.
2007/0208266 A1 9/2007 Hadley
2007/0225611 A1 9/2007 Kumar et al.
2007/0249946 A1 10/2007 Kumar et al.
2007/0255153 A1 11/2007 Kumar et al.
2007/0270678 A1 11/2007 Fadem et al.
2007/0285868 A1 12/2007 Lindberg et al.
2007/0293776 A1 12/2007 Korzinov et al.
2007/0299325 A1 12/2007 Farrell
2008/0039730 A1 2/2008 Pu et al.
2008/0091089 A1 4/2008 Guillory et al.
2008/0108890 A1 5/2008 Teng et al.
2008/0114232 A1 5/2008 Gazit
2008/0139953 A1 6/2008 Baker et al.
2008/0167567 A1 7/2008 Bashour et al.
2008/0214901 A1 9/2008 Gehman et al.
2008/0275327 A1 11/2008 Faarbaek et al.
2008/0281215 A1 11/2008 Alhussiny
2008/0288026 A1 11/2008 Cross et al.
2008/0309287 A1 12/2008 Reed
2009/0048556 A1 2/2009 Durand
2009/0062670 A1 3/2009 Sterling et al.
2009/0062671 A1 3/2009 Brockway
2009/0073991 A1 3/2009 Landrum et al.
2009/0076336 A1 3/2009 Mazar et al.
2009/0076340 A1 3/2009 Libbus et al.
2009/0076341 A1 3/2009 James et al.
2009/0076342 A1 3/2009 Amurthur et al.
2009/0076343 A1 3/2009 James et al.
2009/0076344 A1 3/2009 Libbus et al.
2009/0076345 A1 3/2009 Manicka et al.
2009/0076346 A1 3/2009 James et al.
2009/0076349 A1 3/2009 Libbus et al.
2009/0076350 A1 3/2009 Bly et al.
2009/0076363 A1 3/2009 Bly et al.
2009/0076364 A1 3/2009 Libbus et al.
2009/0076397 A1 3/2009 Libbus et al.
2009/0076401 A1 3/2009 Mazar et al.
2009/0076559 A1 3/2009 Libbus et al.
2009/0182204 A1 7/2009 Semler et al.
2009/0253975 A1 10/2009 Tiegs
2009/0283300 A1 11/2009 Grunthaner
2009/0292193 A1 11/2009 Wijesiriwardana
2009/0292194 A1 11/2009 Libbus et al.
2009/0306485 A1 12/2009 Bell
2010/0001541 A1 1/2010 Sugiyama
2010/0016701 A1 1/2010 Cheng et al.
2010/0022864 A1 1/2010 Cordero
2010/0042113 A1 2/2010 Mah
2010/0049006 A1 2/2010 Magar et al.
2010/0051039 A1 3/2010 Ferrara
2010/0056881 A1 3/2010 Libbus et al.
2010/0057056 A1 3/2010 Gurtner
2010/0076533 A1 3/2010 Dar et al.
2010/0081913 A1 4/2010 Cross et al.
2010/0145359 A1 6/2010 Keller
2010/0191310 A1 7/2010 Bly
2010/0234716 A1 9/2010 Engel
2010/0249625 A1 9/2010 Lin
2010/0268103 A1 10/2010 McNamara et al.
2010/0312131 A1 12/2010 Naware et al.
2010/0331711 A1 12/2010 Krauss et al.
2011/0021937 A1 1/2011 Hugh et al.
2011/0087083 A1 4/2011 Poeze et al.
2011/0098583 A1 4/2011 Pandia et al.
2011/0119212 A1 5/2011 De Bruin et al.
2011/0144470 A1 6/2011 Mazar et al.
2011/0160601 A1 6/2011 Wang et al.
2011/0166468 A1 7/2011 Prystowsky et al.
2011/0190650 A1 8/2011 McNair
2011/0218415 A1 9/2011 Chen
2011/0237922 A1 9/2011 Parker, III et al.
2011/0237924 A1 9/2011 McGusty et al.
2011/0251504 A1 10/2011 Tereshchenko et al.
2011/0270049 A1 11/2011 Katra et al.
2011/0279963 A1 11/2011 Kumar et al.
2011/0306862 A1 12/2011 Hayes-Gill
2012/0029306 A1 2/2012 Paquet et al.
2012/0029307 A1 2/2012 Paquet et al.
2012/0071730 A1 3/2012 Romero
2012/0071731 A1 3/2012 Gottesman
2012/0071743 A1 3/2012 Todorov et al.
2012/0083670 A1 4/2012 Rotondo et al.
2012/0088999 A1 4/2012 Bishay et al.
2012/0101396 A1 4/2012 Solosko et al.
2012/0108917 A1 5/2012 Libbus et al.
2012/0108920 A1 5/2012 Bly et al.
2012/0110226 A1 5/2012 Vlach et al.
2012/0110228 A1 5/2012 Vlach et al.
2012/0123232 A1 5/2012 Najarian et al.
2012/0133162 A1 5/2012 Sgobero
2012/0172676 A1 7/2012 Penders et al.
2012/0173470 A1* 7/2012 Bashour ................ G16H 50/30
706/15
2012/0197150 A1 8/2012 Cao et al.
2012/0209102 A1 8/2012 Ylotalo et al.
2012/0209126 A1 8/2012 Amos et al.
2012/0215123 A1 8/2012 Kumar et al.
2012/0220835 A1 8/2012 Chung
2012/0259233 A1 10/2012 Chan et al.
2012/0271141 A1 10/2012 Davies
2012/0310070 A1 12/2012 Kumar et al.
2012/0316532 A1 12/2012 McCormick
2012/0323257 A1 12/2012 Sutton
2012/0330126 A1 12/2012 Hoppe et al.
2013/0023816 A1 1/2013 Bachinski et al.
2013/0041273 A1 2/2013 Houben et al.
2013/0046151 A1 2/2013 Bsoul et al.
2013/0085347 A1 4/2013 Manicka et al.
2013/0085538 A1 4/2013 Volpe et al.
2013/0096395 A1 4/2013 Katra et al.
2013/0116533 A1 5/2013 Lian et al.
2013/0116585 A1 5/2013 Bouguerra
2013/0144146 A1 6/2013 Linker
2013/0150698 A1 6/2013 Hsu et al.
2013/0158494 A1 6/2013 Ong
2013/0172763 A1 7/2013 Wheeler
2013/0184662 A1 7/2013 Aali et al.
2013/0191035 A1 7/2013 Chon et al.
2013/0225938 A1 8/2013 Vlach
2013/0225967 A1 8/2013 Esposito
2013/0226018 A1 8/2013 Kumar et al.
2013/0245415 A1 9/2013 Kumar et al.
2013/0245472 A1 9/2013 Eveland
2013/0253285 A1 9/2013 Bly et al.
2013/0274584 A1 10/2013 Finlay et al.
2013/0289424 A1 10/2013 Brockway et al.
2013/0296680 A1 11/2013 Linker
2013/0300575 A1 11/2013 Kurzweil et al.
2013/0324868 A1 12/2013 Kaib et al.
2013/0331663 A1 12/2013 Albert et al.
2013/0331665 A1 12/2013 Bly et al.
2013/0338448 A1 12/2013 Libbus et al.

(56) References Cited

U.S. PATENT DOCUMENTS

2014/0012154 A1 1/2014 Mazar
2014/0058280 A1 2/2014 Chefles et al.
2014/0088394 A1 3/2014 Sunderland
2014/0094676 A1 4/2014 Gani et al.
2014/0094709 A1 4/2014 Korzinov et al.
2014/0100432 A1 4/2014 Golda et al.
2014/0116825 A1 5/2014 Lindeman
2014/0171751 A1 6/2014 Sankman et al.
2014/0206976 A1 7/2014 Thompson et al.
2014/0206977 A1 7/2014 Bahney et al.
2014/0243621 A1 8/2014 Weng et al.
2014/0275827 A1 9/2014 Gill et al.
2014/0275840 A1 9/2014 Osorio
2014/0275928 A1 9/2014 Acquista et al.
2014/0303647 A1 10/2014 Sepulveda et al.
2014/0330136 A1 11/2014 Manicka et al.
2015/0005854 A1 1/2015 Said
2015/0022372 A1 1/2015 Vosch
2015/0057512 A1 2/2015 Kapoor
2015/0073252 A1 3/2015 Mazar
2015/0081959 A1 3/2015 Vlach et al.
2015/0082623 A1 3/2015 Felix et al.
2015/0087921 A1 3/2015 Felix et al.
2015/0087922 A1 3/2015 Bardy et al.
2015/0087923 A1 3/2015 Bardy et al.
2015/0087933 A1 3/2015 Gibson et al.
2015/0087948 A1 3/2015 Bishay et al.
2015/0087949 A1 3/2015 Felix et al.
2015/0087950 A1 3/2015 Felix et al.
2015/0087951 A1 3/2015 Felix et al.
2015/0088007 A1 3/2015 Bardy et al.
2015/0088020 A1 3/2015 Dreisbach et al.
2015/0094556 A1 4/2015 Geva et al.
2015/0148637 A1 5/2015 Golda et al.
2015/0157273 A1 6/2015 An et al.
2015/0173671 A1 6/2015 Paalasmaa et al.
2015/0193595 A1 7/2015 McNamara et al.
2015/0223711 A1 8/2015 Raeder et al.
2015/0238107 A1 8/2015 Acquista et al.
2015/0289814 A1 10/2015 Magar et al.
2015/0297134 A1 10/2015 Albert et al.
2015/0327781 A1 11/2015 Hernandez-Silverira et al.
2015/0351689 A1 12/2015 Adams
2015/0351799 A1 12/2015 Sepulveda et al.
2015/0374244 A1 12/2015 Yoo et al.
2016/0022161 A1 1/2016 Khair
2016/0029906 A1 2/2016 Tompkins et al.
2016/0066808 A1 3/2016 Hijazi
2016/0085927 A1 3/2016 Dettinger et al.
2016/0085937 A1 3/2016 Dettinger et al.
2016/0086297 A1 3/2016 Dettinger et al.
2016/0098536 A1 4/2016 Dettinger et al.
2016/0098537 A1 4/2016 Dettinger et al.
2016/0113520 A1 4/2016 Manera
2016/0120433 A1 5/2016 Hughes et al.
2016/0120434 A1 5/2016 Park et al.
2016/0128597 A1 5/2016 Lin et al.
2016/0135746 A1 5/2016 Kumar et al.
2016/0149292 A1 5/2016 Ganton
2016/0157744 A1 6/2016 Wu et al.
2016/0166155 A1 6/2016 Banet et al.
2016/0192852 A1 7/2016 Bozza et al.
2016/0192855 A1 7/2016 Geva et al.
2016/0192856 A1 7/2016 Lee
2016/0198972 A1 7/2016 Lee et al.
2016/0232807 A1 8/2016 Ghaffari et al.
2016/0262619 A1 9/2016 Marcus et al.
2016/0278658 A1 9/2016 Bardy et al.
2016/0287177 A1 10/2016 Huppert et al.
2016/0287207 A1 10/2016 Xue
2016/0296132 A1 10/2016 Bojovic et al.
2016/0302725 A1 10/2016 Schultz et al.
2016/0302726 A1 10/2016 Chang
2016/0317048 A1 11/2016 Chan et al.
2016/0317057 A1 11/2016 Li et al.
2016/0359150 A1 12/2016 de Francisco Martin et al.
2016/0361015 A1 12/2016 Wang et al.
2016/0367164 A1 12/2016 Felix et al.
2016/0374583 A1 12/2016 Cerruti et al.
2017/0042447 A1 2/2017 Rossi
2017/0055896 A1 3/2017 Al-Ali et al.
2017/0056682 A1 3/2017 Kumar
2017/0065823 A1 3/2017 Kaib et al.
2017/0076641 A1 3/2017 Senanayake
2017/0188872 A1 7/2017 Hughes et al.
2017/0188971 A1 7/2017 Hughes et al.
2018/0049698 A1 2/2018 Berg
2018/0049716 A1 2/2018 Rajagopal et al.
2018/0064388 A1 3/2018 Heneghan et al.
2018/0110266 A1 4/2018 Lee et al.
2018/0125387 A1 5/2018 Hadley et al.
2018/0144241 A1 5/2018 Liu et al.
2018/0146875 A1 5/2018 Friedman et al.
2018/0161211 A1 6/2018 Beckey
2018/0242876 A1 8/2018 Hughes et al.
2018/0257346 A1 9/2018 Austin
2018/0260706 A1 9/2018 Galloway et al.
2018/0289274 A1 10/2018 Bahney et al.
2018/0374576 A1 12/2018 Dettinger et al.
2019/0015008 A1 1/2019 Alizadeh et al.
2019/0021671 A1 1/2019 Kumar et al.
2019/0038148 A1 2/2019 Valys
2019/0046066 A1 2/2019 Hughes et al.
2019/0069788 A1 3/2019 Coleman et al.
2019/0090769 A1 3/2019 Boleyn et al.
2019/0097339 A1 3/2019 Lim et al.
2019/0098758 A1 3/2019 Hassemer et al.
2019/0099132 A1 4/2019 Mulinti et al.
2019/0125260 A1 5/2019 Levesque et al.
2019/0133468 A1 5/2019 Aliamiri et al.
2019/0167143 A1 6/2019 Li et al.
2019/0209022 A1 7/2019 Sobol
2019/0246928 A1 8/2019 Bahney et al.
2019/0274574 A1 9/2019 Hughes et al.
2019/0282178 A1 9/2019 Volosin et al.
2019/0290147 A1 9/2019 Persen et al.
2019/0298201 A1 10/2019 Persen et al.
2019/0298209 A1 10/2019 Persen et al.
2019/0298272 A1 10/2019 Persen
2019/0320930 A1* 10/2019 Derkx .................... A61B 5/313
2019/0328264 A1 10/2019 Jeong
2019/0370636 A1 12/2019 Isopoussu
2019/0374163 A1 12/2019 Faabaek et al.
2019/0378617 A1 12/2019 Charles et al.
2020/0060563 A1 2/2020 Boleyn
2020/0093388 A1 3/2020 Bouguerra et al.
2020/0100693 A1 4/2020 Velo
2020/0101278 A1 4/2020 Freeman et al.
2020/0108260 A1 4/2020 Haddad et al.
2020/0121209 A1 4/2020 Kumar et al.
2020/0170529 A1 6/2020 Bahney et al.
2020/0178825 A1 6/2020 Lu
2020/0178828 A1 6/2020 Bahney et al.
2020/0193597 A1 6/2020 Fan et al.
2020/0214563 A1 7/2020 Lin
2020/0214584 A1 7/2020 McNamara et al.
2020/0237309 A1 7/2020 Golda et al.
2020/0289014 A1 9/2020 Park et al.
2020/0297230 A1 9/2020 Thakur et al.
2020/0337608 A1 10/2020 Garai et al.
2020/0352489 A1 11/2020 Hoppe et al.
2020/0367779 A1 11/2020 Korzinov et al.
2020/0397313 A1 12/2020 Attia et al.
2021/0038102 A1 2/2021 Boleyn et al.
2021/0059612 A1 3/2021 Krebs et al.
2021/0076960 A1* 3/2021 Fornwalt ................ A61B 5/361
2021/0085215 A1 3/2021 Auerbach et al.
2021/0085255 A1 3/2021 Vule et al.
2021/0125722 A1 4/2021 Sherkat et al.
2021/0153761 A1 5/2021 Jung et al.
2021/0217519 A1 7/2021 Park et al.
2021/0269046 A1 9/2021 Hashimoto et al.
2021/0298688 A1 9/2021 Banerjee et al.
2021/0304855 A1 9/2021 Ansari et al.

(56) References Cited

U.S. PATENT DOCUMENTS

| | | | |
|---|---|---|---|
| 2021/0315470 | A1 | 10/2021 | Wu et al. |
| 2021/0315504 | A1 | 10/2021 | Kumar et al. |
| 2021/0361218 | A1 | 11/2021 | Szabados et al. |
| 2021/0374502 | A1 | 12/2021 | Roth et al. |
| 2021/0378579 | A1 | 12/2021 | Doron et al. |
| 2021/0393187 | A1 | 12/2021 | Amos et al. |
| 2022/0022798 | A1 | 1/2022 | Soon-Shiong et al. |
| 2022/0031223 | A1 | 2/2022 | Li et al. |
| 2022/0039719 | A1 | 2/2022 | Abercrombie, II et al. |
| 2022/0039720 | A1 | 2/2022 | Abercrombie, II et al. |
| 2022/0079497 | A1 | 3/2022 | Bardy et al. |
| 2022/0084669 | A1 | 3/2022 | Van Berkel et al. |
| 2022/0084680 | A1* | 3/2022 | Schmid .................. G16H 40/20 |
| 2022/0093247 | A1 | 3/2022 | Park et al. |
| 2022/0095982 | A1 | 3/2022 | de Saint Victor et al. |
| 2022/0142493 | A1 | 5/2022 | Albert |
| 2022/0142495 | A1 | 5/2022 | De Marco et al. |
| 2022/0280093 | A1 | 9/2022 | Abercrombie, II et al. |
| 2022/0296144 | A1 | 9/2022 | Abercrombie, II et al. |
| 2022/0330874 | A1 | 10/2022 | Szabados et al. |
| 2022/0361793 | A1 | 11/2022 | Abercrombie, II et al. |
| 2023/0036193 | A1 | 2/2023 | Li et al. |
| 2023/0056777 | A1 | 2/2023 | Abercrombie, II et al. |
| 2023/0172511 | A1 | 6/2023 | Abercrombie, II et al. |
| 2023/0172518 | A1 | 6/2023 | Szabados et al. |
| 2023/0248288 | A1 | 8/2023 | Bahney et al. |
| 2023/0371873 | A1 | 11/2023 | Abercrombie, II et al. |
| 2023/0371874 | A1 | 11/2023 | Abercrombie, II et al. |
| 2024/0145080 | A1 | 5/2024 | Park et al. |
| 2024/0331875 | A1 | 10/2024 | Hytopoulos et al. |
| 2024/0358310 | A1 | 10/2024 | Szabados et al. |
| 2024/0382130 | A1 | 11/2024 | Bahney et al. |
| 2024/0382131 | A1 | 11/2024 | Bahney et al. |
| 2024/0398309 | A1 | 12/2024 | Kumar et al. |
| 2024/0398310 | A1 | 12/2024 | Kumar et al. |
| 2025/0009271 | A1 | 1/2025 | Bahney et al. |
| 2025/0057459 | A1 | 2/2025 | Kumar et al. |
| 2025/0241578 | A1 | 7/2025 | Abercrombie, II et al. |
| 2026/0007345 | A1 | 1/2026 | Bahney et al. |
| 2026/0026726 | A1 | 1/2026 | Kumar et al. |

FOREIGN PATENT DOCUMENTS

| | | |
|---|---|---|
| AU | 2021218704 | 2/2024 |
| AU | 2021320404 | 7/2025 |
| AU | 2023251520 | 9/2025 |
| CA | 2 752 154 | 8/2010 |
| CA | 2 898 626 | 7/2014 |
| CA | 2 797 980 | 8/2015 |
| CA | 2 651 203 | 9/2017 |
| CA | 2 966 182 | 6/2020 |
| CA | 3 171 482 | 3/2024 |
| CN | 102038497 | 7/2012 |
| CN | 102917638 | 2/2013 |
| CN | 102883775 | 12/2014 |
| CN | 103997955 | 11/2016 |
| CN | 303936805 | 11/2016 |
| CN | 106456984 | 2/2017 |
| CN | 107072603 | 8/2017 |
| CN | 107205504 | 9/2017 |
| CN | 107205679 | 9/2017 |
| CN | 107708991 | 2/2018 |
| CN | 108113647 | 6/2018 |
| CN | 108135929 | 6/2018 |
| CN | 109363659 | 2/2019 |
| CN | 110491500 | 11/2019 |
| CN | 110766691 | 2/2020 |
| CN | 110890155 | 3/2020 |
| CN | 110974217 | 4/2020 |
| CN | 111031926 | 4/2020 |
| CN | 111067509 | 4/2020 |
| CN | 115426940 | 12/2022 |
| CN | 116322498 | 6/2023 |
| CN | 116530951 | 8/2023 |
| CN | 120152655 | 6/2025 |
| EM | 001857966-0001 | 5/2011 |
| EM | 003611714-0001 | 1/2017 |
| EM | 003611714-0002 | 1/2017 |
| EM | 003611714-0003 | 1/2017 |
| EM | 003611714-0004 | 1/2017 |
| EM | 003611714-0005 | 1/2017 |
| EP | 0509689 | 4/1992 |
| EP | 1738686 | 6/2006 |
| EP | 1782729 | 5/2007 |
| EP | 1981402 | 10/2008 |
| EP | 1962686 | 11/2009 |
| EP | 2262419 | 12/2010 |
| EP | 2395911 | 12/2011 |
| EP | 2568878 | 3/2013 |
| EP | 2635179 | 9/2013 |
| EP | 2635180 | 9/2013 |
| EP | 2635938 | 9/2013 |
| EP | 2948050 | 12/2015 |
| EP | 2983593 | 2/2016 |
| EP | 3165161 | 5/2017 |
| EP | 3212061 | 9/2017 |
| EP | 3753483 | 12/2020 |
| EP | 3387991 | 6/2022 |
| EP | 4103051 | 12/2022 |
| EP | 4615312 | 9/2025 |
| GB | 2 299 038 | 9/1996 |
| GB | 2 348 707 | 10/2000 |
| IN | 002592907-0001 | 12/2014 |
| JP | S58-152770 U | 10/1983 |
| JP | S61-137539 | 6/1986 |
| JP | H05-329123 | 12/1993 |
| JP | H08-317913 | 3/1996 |
| JP | H08-322952 | 12/1996 |
| JP | H09-108195 | 4/1997 |
| JP | H10-179531 | 7/1998 |
| JP | 2000-037413 | 2/2000 |
| JP | 2000-126145 | 5/2000 |
| JP | 2001-057967 | 3/2001 |
| JP | 2003-275186 | 9/2003 |
| JP | 2004-121360 | 4/2004 |
| JP | 2006-110180 | 4/2006 |
| JP | 2006-136405 | 6/2006 |
| JP | 2006-520657 | 9/2006 |
| JP | 2007-045967 | 2/2007 |
| JP | 2007-503910 | 3/2007 |
| JP | 2007-504917 | 3/2007 |
| JP | 2007-097822 | 4/2007 |
| JP | 2007-296266 | 11/2007 |
| JP | 2008-532596 | 8/2008 |
| JP | 2008-200120 | 9/2008 |
| JP | 2009-518099 | 5/2009 |
| JP | 2009-525816 | 7/2009 |
| JP | 2011-514831 | 5/2011 |
| JP | 2011-516110 | 5/2011 |
| JP | 2011-519583 | 7/2011 |
| JP | 3180038 U | 11/2012 |
| JP | 2013-521966 | 6/2013 |
| JP | 5203973 | 6/2013 |
| JP | 2013-531512 | 8/2013 |
| JP | 1483906 S | 10/2013 |
| JP | 2014-008166 | 1/2014 |
| JP | 5559425 | 7/2014 |
| JP | 2014-150826 | 8/2014 |
| JP | 2014-236982 | 12/2014 |
| JP | 2015-521085 | 7/2015 |
| JP | 2015-530225 | 10/2015 |
| JP | 2015-531954 | 11/2015 |
| JP | 2016-504159 | 2/2016 |
| JP | 2013-517053 | 5/2016 |
| JP | 2016-523139 | 8/2016 |
| JP | 2017-136380 | 8/2017 |
| JP | 6198849 | 9/2017 |
| JP | 2017-209482 | 11/2017 |
| JP | 2018-504148 | 2/2018 |
| JP | 2018-508325 | 3/2018 |
| JP | 2018-513702 | 5/2018 |
| JP | 6336640 | 5/2018 |
| JP | D1596476 | 8/2018 |
| JP | 2018-153651 | 10/2018 |

(56) References Cited

FOREIGN PATENT DOCUMENTS

| | | | |
|---|---|---|---|
| JP | 2018-174995 | | 11/2018 |
| JP | 2018-202159 | | 12/2018 |
| JP | 2019-503761 | | 2/2019 |
| JP | 6491826 | | 3/2019 |
| JP | 6495228 | | 3/2019 |
| JP | 2019-140680 | | 8/2019 |
| JP | 2019-528511 | | 10/2019 |
| JP | 2020-058819 | | 4/2020 |
| JP | 2020-509840 | | 4/2020 |
| JP | 6766199 | | 9/2020 |
| JP | 2021-003591 | | 1/2021 |
| JP | 6901543 | | 6/2021 |
| JP | 2021-525616 | | 9/2021 |
| JP | 2021-166726 | | 10/2021 |
| JP | 2022-501123 | | 1/2022 |
| JP | 2022-037153 | | 3/2022 |
| JP | 2022-038858 | | 3/2022 |
| JP | 2022-126807 | | 8/2022 |
| JP | 2023-508235 | | 3/2023 |
| JP | 2023-074267 | | 5/2023 |
| JP | 2023-100210 | | 7/2023 |
| JP | 2023-536981 | | 8/2023 |
| JP | 2023-536982 | | 8/2023 |
| JP | 7406001 | | 12/2023 |
| JP | 2024-009608 | | 1/2024 |
| JP | 2024-502335 | | 1/2024 |
| JP | 2024-021061 | | 2/2024 |
| JP | 2024-026058 | | 2/2024 |
| JP | 7431777 | | 2/2024 |
| JP | 2024-050777 | | 4/2024 |
| JP | 2024-521799 | | 6/2024 |
| JP | 2024-087811 | | 7/2024 |
| JP | 2024-104034 | | 8/2024 |
| JP | 7551696 | | 9/2024 |
| JP | 2024-164285 | | 11/2024 |
| JP | 2025-000653 | | 1/2025 |
| JP | 2025-500035 | | 1/2025 |
| JP | 7667221 | | 4/2025 |
| JP | 7796108 | | 12/2025 |
| KR | 3003784570000 | | 3/2005 |
| KR | 1020050055072 | | 6/2005 |
| KR | 1020140050374 | | 4/2014 |
| KR | 10-1513288 | | 4/2015 |
| KR | 3008476060000 | | 3/2016 |
| KR | 3008476090000 | | 3/2016 |
| KR | 3008482960000 | | 3/2016 |
| KR | 3008584120000 | | 6/2016 |
| KR | 3008953750000 | | 2/2017 |
| KR | 3008953760000 | | 2/2017 |
| KR | 3008987790000 | | 3/2017 |
| KR | 1020170133527 | | 12/2017 |
| KR | 3009445870000 | | 2/2018 |
| KR | 3009547690000 | | 4/2018 |
| KR | 3009547710000 | | 4/2018 |
| KR | 10-2019-0114694 | | 10/2019 |
| KR | 10-2563372 | | 7/2023 |
| KR | 10-2023-0119036 | | 8/2023 |
| KR | 10-2024-0116830 | | 7/2024 |
| KR | 10-2811696 | | 5/2025 |
| WO | WO 87/01024 | | 2/1987 |
| WO | WO 99/023943 | | 5/1999 |
| WO | WO 01/016607 | | 3/2001 |
| WO | WO 2003/043494 | | 5/2003 |
| WO | WO 2004/100785 | | 11/2004 |
| WO | WO 2005/025668 | | 3/2005 |
| WO | WO 2005/037946 | | 4/2005 |
| WO | WO 2005/084533 | | 9/2005 |
| WO | WO 2006/094513 | | 9/2006 |
| WO | WO 2007/049080 | | 3/2007 |
| WO | WO 2007/036748 | | 4/2007 |
| WO | WO 2007/063436 | | 6/2007 |
| WO | WO 2007/066270 | | 6/2007 |
| WO | WO 2007/071180 | | 6/2007 |
| WO | WO 2007/072069 | | 6/2007 |
| WO | WO 2007/092543 | | 8/2007 |

| | | | |
|---|---|---|---|
| WO | WO 2008/005015 | | 1/2008 |
| WO | WO 2008/005016 | | 1/2008 |
| WO | WO 2008/057884 | | 5/2008 |
| WO | WO 2008/120154 | | 10/2008 |
| WO | WO 2009/055397 | | 4/2009 |
| WO | WO 2009/074928 | | 6/2009 |
| WO | WO 2009/112972 | | 9/2009 |
| WO | WO 2009/112976 | | 9/2009 |
| WO | WO 2009/112979 | | 9/2009 |
| WO | WO 2009/134826 | | 11/2009 |
| WO | WO 2010/014490 | | 2/2010 |
| WO | WO 2010/104952 | | 9/2010 |
| WO | WO 2010/105203 | | 9/2010 |
| WO | WO 2010/107913 | A2 | 9/2010 |
| WO | WO 2010/093900 | | 10/2010 |
| WO | WO 2011/077097 | | 6/2011 |
| WO | WO 2011/084636 | | 7/2011 |
| WO | WO 2011/112420 | | 9/2011 |
| WO | WO 2011/143490 | | 11/2011 |
| WO | WO 2011/149755 | | 12/2011 |
| WO | WO 2012/003840 | | 1/2012 |
| WO | WO 2012/009453 | | 1/2012 |
| WO | WO 2012/061509 | | 5/2012 |
| WO | WO 2012/061518 | | 5/2012 |
| WO | WO 2012/125425 | | 9/2012 |
| WO | WO 2012/140559 | | 10/2012 |
| WO | WO 2012/160550 | | 11/2012 |
| WO | WO 2013/065147 | | 5/2013 |
| WO | WO 2013/179368 | | 12/2013 |
| WO | WO 2014/047032 | | 3/2014 |
| WO | WO 2014/047205 | | 3/2014 |
| WO | WO 2014/051563 | | 4/2014 |
| WO | WO 2014/055994 | | 4/2014 |
| WO | WO 2014/116825 | | 7/2014 |
| WO | WO 2014/168841 | | 10/2014 |
| WO | WO 2014/197822 | | 12/2014 |
| WO | WO 2015/089484 | | 6/2015 |
| WO | WO 2015/127466 | | 8/2015 |
| WO | WO 2016/044514 | | 3/2016 |
| WO | WO 2016/044515 | | 3/2016 |
| WO | WO 2016/044519 | | 3/2016 |
| WO | WO 2016/057728 | | 4/2016 |
| WO | WO 2016/070128 | | 5/2016 |
| WO | WO 2016/130545 | | 8/2016 |
| WO | WO 2016/172201 | | 10/2016 |
| WO | WO 2016/181321 | | 11/2016 |
| WO | WO 2017/039518 | | 3/2017 |
| WO | WO 2017/041014 | | 3/2017 |
| WO | WO 2017/043597 | | 3/2017 |
| WO | WO 2017/043603 | | 3/2017 |
| WO | WO 2017/108215 | | 6/2017 |
| WO | WO 2017/159635 | | 9/2017 |
| WO | WO 2018/164840 | | 9/2018 |
| WO | WO 2018/218310 | | 12/2018 |
| WO | WO 2019/070978 | | 4/2019 |
| WO | WO 2019/071201 | | 4/2019 |
| WO | WO 2019/188311 | | 10/2019 |
| WO | WO 2019/191487 | | 10/2019 |
| WO | WO 2019/233807 | | 12/2019 |
| WO | WO 2020/008864 | | 1/2020 |
| WO | WO 2020/013895 | | 1/2020 |
| WO | WO 2020/041363 | | 2/2020 |
| WO | WO 2020/058314 | | 3/2020 |
| WO | WO 2020/072989 | | 4/2020 |
| WO | WO 2020/224041 | | 11/2020 |
| WO | WO 2020/0226852 | | 11/2020 |
| WO | WO 2020/262403 | | 12/2020 |
| WO | WO 2021/055870 | | 3/2021 |
| WO | WO 2021/150122 | | 7/2021 |
| WO | WO 2021/163331 | | 8/2021 |
| WO | WO 2021/200245 | | 10/2021 |
| WO | WO 2021/200764 | | 10/2021 |
| WO | WO 2021/205788 | | 10/2021 |
| WO | WO 2021/210592 | | 10/2021 |
| WO | WO 2021/241308 | | 12/2021 |
| WO | WO 2021245203 | | 12/2021 |
| WO | WO 2022034045 | | 2/2022 |
| WO | WO 2022093709 | | 5/2022 |
| WO | WO 2022/147520 | | 7/2022 |

(56) References Cited

FOREIGN PATENT DOCUMENTS

| | | |
|---|---|---|
| WO | WO 2022/251636 | 12/2022 |
| WO | WO 2023/114742 | 6/2023 |
| WO | WO 2024/102663 A2 | 5/2024 |

OTHER PUBLICATIONS

Poungponsri et al.—"An adaptive filtering approach for electrocardiogram (ECG) signal noise reduction using neural networks"; Neurocomputing 117 (2013) pp. 206-213.*
Behind the Design: How iRhythm Built Its New Zio Monitor. Online, published date Oct. 4, 2023. Retrieved on Jun. 18, 2024 from URL: https://www.mddionline.com/cardiovascular/behind-the-design-how-irhythm-built-its-new-zio-monitor.
3M Corporation, "3M Surgical Tapes—Choose the Correct Tape" quicksheet (2004).
Akram, Muhammad Usman, "Application of Prototype Based Fuzzy Classifiers for ECG based Cardiac Arrhythmia Recognition", Jan. 1, 2008 retrieved from faculty.pieas.edu.pk/Fayyaz/_static/pubfiles/student/usman_thesis.pdf [retrieved on Feb. 17, 2015] in 93 pages.
Altini, et al., An ECG Patch Combining a Customized Ultra-Low-Power ECG SOC Withbluetooth Low Energy for Long Term Ambulatory Monitoring, Conference: Proceddings of Wireless Health 2011, WH 2011, Oct. 10-13, 2011.
British-Made Early Warning Monitor a "Game Changer", healthcare-in-europe.com, Mar. 31, 2014.
Comstock, Proteus Digital Health Quietly Launches Consumer-Facing Wearable for Athletes, Mobile Health News, Oct. 29, 2014.
Coxworth, Small Adhesive Partch Outperforms Traditional Tech for Detecting Arrhythmia, Scripps, iRhythm Technologies, Jan. 3, 2014.
Del Mar et al.; The history of clinical holter monitoring; A.N.E.; vol. 10; No. 2; pp. 226-230; Apr. 2005.
Design Search Project Overview as referenced in Petition to Request Expedited Examination.
English translation of Office Action for Japanese Application No. 2015-555272 dated Aug. 30, 2016.
Enseleit et al.; Long-term continuous external electrocardiogramecording: a review; Eurospace; vol. 8; pp. 255-266; 2006.
Examination Report No. 1, dated Oct. 7, 2022 for Application No. 2021218704, Filed Aug. 19, 2022 (3pages).
Extended European Search Report for EP 23161870 dated Jul. 4, 2023 in 14 pages.
Feng-Tso Sun et al., "PEAR: Power efficiency through activity recognition (for ECG-based sensing)", Pervasive Computing Technologies for Healthcare (Pervasivehealth) 2011 5th International Conference on, IEEE, May 23, 2011. pp. 115-122.
Hoefman et al.; Optimal duration of event recording for diagnosis of arrhythmias in patients with palpitations and light-headedness in the general practice; Family Practice; Dec. 7, 2006.
Huyett "Keystock & Shim Stock Catalog" p. 9 Feb. 2014. found at https://issuu.com/glhuyett/docs/gl-huyett-keystock-catalog/20 (Year: 2014).
Ikeda Y. et al., "A Method for Transmission Data Reduction for Automated Monitoring System via CNN Distribution Process", Proceedings of the Symposium of Multi-media, Distribution, Coordination, and Mobile (DOCOMO2019), Jul. 2019.
International Preliminary Report on Patentability and Written Opinion in PCT Application No. PCT/US07/003343, dated Aug. 12, 2008.
International Preliminary Report on Patentability and Written Opinion in PCT Application No. PCT/US2011/036335), dated Nov. 22, 2012.
International Preliminary Report on Patentability and Written Opinion in PCT Application No. PCT/US2014/012749, dated Aug. 6, 2015.
International Preliminary Report on Patentability and Written Opinion in PCT Application No. PCT/US2014/033064, dated Oct. 22, 2015.
International Preliminary Report on Patentability and Written Opinion in PCT Application No. PCT/US2015/058478, dated May 11, 2017.
International Search Report and Written Opinion in PCT Application No. PCT/US07/003343, as dated Feb. 28, 2008.
International Search Report and Written Opinion in PCT Application No. PCT/US2011/036335, dated Oct. 31, 2011.
International Search Report and Written Opinion in PCT Application No. PCT/US2014/012749, dated Mar. 21, 2014.
International Search Report and Written Opinion in PCT Application No. PCT/US2014/033064, dated Sep. 23, 2014.
International Search Report and Written Opinion for International Application No. PCT/US2015/058478 mailed Feb. 16, 2016 in 12 pages.
International Search Report and Written Opinion for International Application No. PCT/US2021/044976 mailed Jan. 24, 2022 in 24 pages.
International Search Report and Written Opinion received in PCT Application No. PCT/US2022/081409, dated May 4, 2023 in 24 pages.
International Search Report and Written Opinion received in PCT Application No. PCT/US2023/078848, dated May 7, 2024 in 18 pages.
Jan. 24, 2023 Japanese Office Action from related JP 2022-549034 (7 pgs).
Japanese Office Action for JP Application No. 2021-174323 mailed Nov. 1, 2022.
Kennedy et al.; The history, science, and innovation of holter technology; A.N.E.; vol. 11; No. 1; pp. 85-94; 2006.
"Mayo Alumni", Mayo Clinic, Rochester, MN, Spring 2011, in 24 pages.
Medtronic Launches Seeq Wearable Cardiac Monitoring System in United States, Diagnostic and Interventional Cardiology, Oct. 7, 2014.
Mundt et al. "A Multiparameter Wearable Physiologic Monitoring System for Space and Terrestrial Applications" IEEE Transactions on Information Technology in Biomedicine, vol. 9, No. 3, pp. 382-384, Sep. 2005.
Official Communication received in European Search Report received in European Patent Application No. 11781310.5, dated Aug. 29, 2014.
Official Communication received in European Search Report received in European Patent Application No. 22171519, dated Nov. 17, 2022.
Office Action received in Chinese Patent Application No. 202180027882.9, dated Mar. 16, 2024.
PCT Search Report of May 6, 2021 for International Patent Application No. PCT/US2021/017667.
Prakash, New Patch-Based Wearable Sensor Combines Advanced Skin Adhesives and Sensor Technologies, Advantage Business Marketing, Jul. 17, 2012.
Rajpurkar et al., "Cardiologist-Level Arrhythmia Detection with Convolutinal Neural Networks," ARXIV.org, https://arxiv.org/abs/1707.01836, Jul. 6, 2017 in 9 pages.
Redjem Bouhenguel et al, "A risk and Incidence Based Atrial Fibrillation Detection Scheme forWearable Healthcare Computing Devices," Pervasive Computer Technologies for Healthcare, 2012 6th International Conference on, IEEE, pp. 97-104, May 21, 2012.
Reiffel et al.; Comparison of autotriggered memory loop recorders versus standard loop recordersversus 24-hour holter monitors for arrhythmia detection; Am. J. Cardiology; vol. 95; pp. 1055-1059; May 1, 2005.
Request for Reexamination of U.S. Pat. No. 7,020,508 under 35 U.S.C. §§ 311-318 and 37 C.F.R. § 1.913 as submitted Sep. 14, 2012 in 78 pages.
Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Sep. 24, 2012.
Strong, Wearable Technologies Conference 2013 Europe—Notes and Roundup, Wearable Technologies Conference, Feb. 8, 2013.
Sumner, Stanford Engineers Monitor Heart Health Using Paper-Thin Flexible 'Skin', Stanford Report, May 14, 2013.

(56) References Cited

OTHER PUBLICATIONS

Supplementary European Search Report received in European Patent Application No. 11781310.5, dated Jul. 30, 2014.
Supplementary European Search Report received in European Patent Application No. 114743121.7, dated Oct. 14, 2016.
Ward et al.; Assessment of the diagnostic value of 24-hour ambulatory electrocardiographic monitoring; Biotelemetry Patient monitoring; vol. 7; 1980.
Ziegler et al.; Comparison of continuous versus intermittent monitoring of atrial arrhythmias; Heart Rhythm; vol. 3; No. 12; pp. 1445-1452; Dec. 2006.
Zimetbaum et al.; The evolving role of ambulatory arrhythmia monitoring in general clinic practice; Ann. Intern. Med.; vol. 130; pp. 846-8556; 1999.
Zimetbaum et al.; Utility of patient-activated cardiac event recorders in general clinical practice; The Amer. J. of Cardiology; vol. 79; Feb. 1, 1997.
AAMI, "Ambulatory electrocardiographs," American National Standards Institute, Inc. Oct. 29, 1998, in 67 pages.
AAMI, "Cardiac monitors, heart rate meters, and alarms," American National Standards Institute, Inc., May 6, 2002, in 87 pages.
ACLS Medical Training, "The Basics of ECG," retrieved from URL: https://www.aclsmedicaltraining.com/basics-of-ecg/, in 3 pages.
Adamec et al., "ECG Holter: Guide to Electrocardiographic Interpretation," Springer Science Business Media, LLC, in 9 pages.
AlGhatrif et al., "A brief review: history to understand fundamentals of electrocardiography," CoActrion, Apr. 30, 2012, in 5 pages.
Ashley et al., "Cardiology Explained," Remedica, 2004, retreieved from URL: https://www.ncbi.nlm.nih.gov/books/NBK2204/?report=printable, in 4 pages.
Cadogan, "Norman J. Holter," Life in the Fastlane, Jul. 27, 2022 in 8 pages.
Chung, "Ambulatory Electrocardiography," Springer-Veriag New York Inc., 1979 in 25 pages.
Crawford et al., "ACC/AHA Guidelines for Ambulatory Electrocardiography: Executive Summary and Recommendations," American College of Cardiology / American Heart Association, Aug. 24, 1999, in 20 pages.
Dexcom STS Sensor, "Instructions for Use," in 51 pages.
Grant, "Spatial Vector Electrocardiography: a Method for Calculating the Spatial Electrical Vectors of the Heart from Conventional Leads," Circulation, vol. 11, Nov. 1950, in 20 pages.
Harland et al., "Electric potential probes—new directions in the remote sensing of the human body," Institute of Physics Publishing, Dec. 21, 2001, pp. 163-169.
Hubner, "Which Disposable Chest Electrode?" British Medical Journal, 1969, pp. 507-510.
Japanese Office Action received in JP Application No. 2023-173428 dated Dec. 3, 2024.
Kalahasty et al., "A Brief History of Remote Cardiac Monitoring," Virginia Commonwealth University School of Medicine and VCUHS Medical Center, 2013 in 8 pages.
Khandpur, "Printed Circuit Boards: Design, Fabrication, Assembly and Testing," McGraw-Hill, 2006, in 43 pages.
Morganroth, "Ambulatory Holter Electrocardiography: Choice of Technologies and Clinical Uses," Annais of Internal Medicine, vol. 102, No. 1, Jan. 1985, in 9 pages.
National Library of Medicine, "In brief: What is an electrocardiogram (ECG)?" Jun. 6, 2023, retrieved from URL: https://www.ncbi.nlm.nih.gov/books/NBK536878/ in 4 pages.
Prutchi et al., "Design and Development of Medical Electronic Instrumentation: a Practical Perspective of the Design, Construction, and Test of Medical Devices," Wiley-Interscience, 2005 in 6 pages.
Thakor, "From Holter Monitors to Automatic Defibrillators: Developments in Ambulatory Arrhythmia Monitoring," IEEE Transactions on Biomedical Engineering, vol. BME-31, No. 12, Dec. 1984, in 9 pages.
Trend et al., "Are ECG Welsh cup electrodes effectively cleaned?" Journal of Hospital Infection, 1989, pp. 325-331.
Young et al., "University Physics," Sears & Zemansky, Fifteenth Edition, in 8 pages.
Youtube.com, "Demonstration of Nintendo controller repair," https://www.youtube.com/watch?v=hzybDNChNeU, Aug. 2010.
Chapfuwa et al., "Adversarial Time-to-Event Modeling", 2018 Proceedings of the 35th International Conference on Machine Learning (Year: 2018).
Gensheimer et al., "A Scalable Discrete-time Survivial Model for Neural Networks", Jan. 25, 2019, Peer J:e6257 (Year:2019).
Mill-Max, "Spring-Loaded Connectors," Mil-Max mfg. Corp, Catalog in 85 pages (accessed Jul. 30, 2025).
Office Action received in Chinese Patent Application No. 202180068765.7, dated Aug. 12, 2025.
Office Action received in Indian Patent Application No. 202227051649, dated Aug. 12, 2025.
Shu et al., Feature Extraction and Arrhythmia Classification from 2-Lead Electrocardiogram Using Stacked Convolutional Denoising Autoencoders, Journal of Information Processing Society of Japan, Japan, Dec. 2018, vol. 59, No. 12, pp. 2213-2220.

* cited by examiner

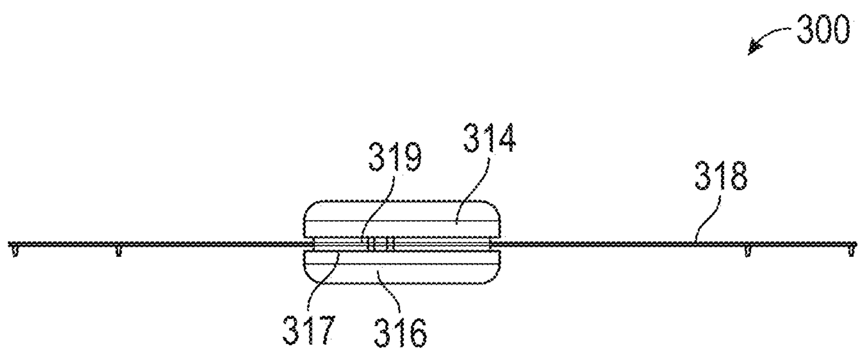
FIG. 3D1
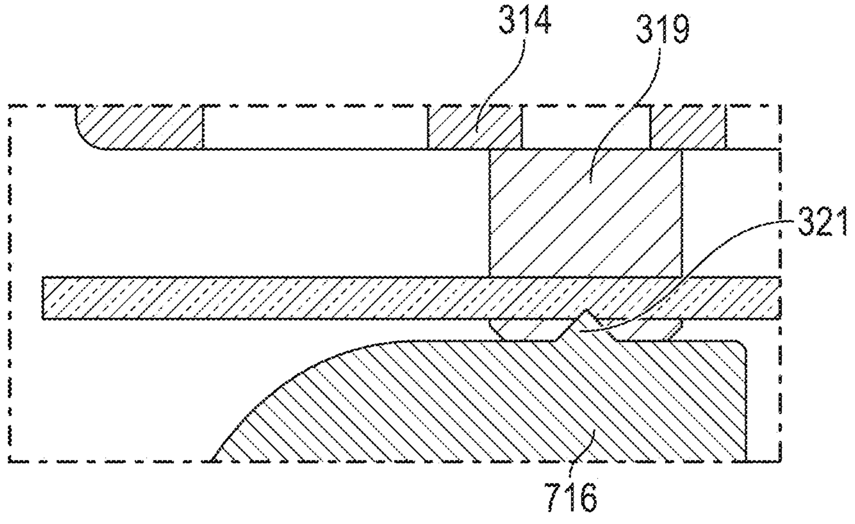
FIG. 3D2

1100

No Atrial Fibrillation Found

AF was not Detected During this Monitoring Period. Below is an Assessment of the Likelihood of AF Developing the Future.

| Risk of Onset(<Follow up Time) | Absolute Risk (%) |
|---|---|
| 12 Months | 3.2% |
| 36 Months | 6.3% |
| 60 Months | 18.0% |

1200

Patient Outcome Risk Predictions

Below is a Visualization of the Risk of Adverse Patient Outcomes Occuring Over Time. Each Outcome has a Corresponding Risk Score, Which Indicates the Likelihood of that Event Occuring Within 36 Months. Both the Score and the Corresponding Risk Curve can be Generated by a Deep Learning Algorithm that can Take Into Account a Patient's Morphology, Findings, Heart Rate, and/or Demographics

Treatment Insights

For Patients with a Similar Risk Profile, Either an Atrial Fibrillation Ablation or Anticoagulant Therapy have been Shown to Reduce the Risk of Adverse Events.

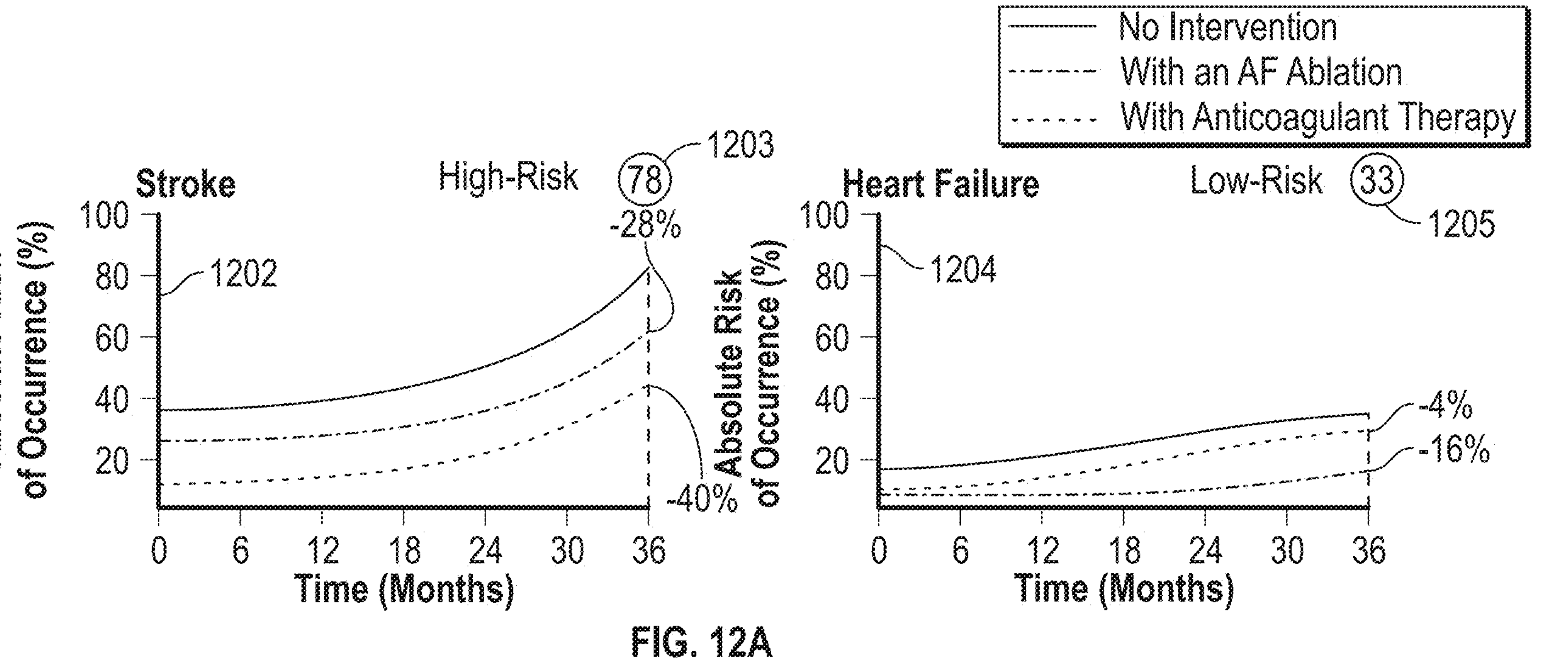

CARDIAC ARRHYTHMIA DETECTION

CROSS-REFERENCE TO RELATED APPLICATIONS

This application is a continuation of International Application No. PCT/US2022/081409, filed on Dec. 13, 2022, which claims priority to provisional U.S. Pat. App. No. 63/265,335, filed on Dec. 13, 2021, which are each hereby incorporated by reference in its entirety. Any and all applications for which a foreign or domestic priority claim is identified in the Application Data Sheet as filed with the present application are hereby incorporated by reference under 37 CFR 1.57.

BACKGROUND

For purposes of this disclosure, certain aspects, advantages, and novel features of various implementations are described herein. It is to be understood that not necessarily all such advantages may be achieved in accordance with any particular implementation. Thus, various implementations may be or carried out in a manner that achieves one advantage or group of advantages as taught herein without necessarily achieving other advantages as may be taught or suggested herein.

BRIEF SUMMARY OF IMPLEMENTATIONS

Implementations described herein are directed to a physiological monitoring device that may be worn continuously and comfortably by a human or animal subject for at least one week or more and more typically two to three weeks or more. In one implementation, the device is specifically designed to sense and record cardiac rhythm (for example, electrocardiogram, ECG) data, although in various alternative implementations one or more additional physiological parameters may be sensed and recorded. Such physiological monitoring devices may include a number of features to facilitate and/or enhance the patient experience and to make diagnosis of cardiac arrhythmias more accurate and timely.

Some implementations described herein can include a computing system for inferring an onset of cardiac arrythmia of a user, the computing system comprising: a sensor configured to detect cardiac signals from a user; and a hardware processor configured to apply the detected cardiac signals to a first machine learning process, wherein the first machine learning process is configured to infer an onset of cardiac arrhythmia based on the detected cardiac signals of the user, wherein the first machine learning process has been trained by: accessing historical cardiac signal patient data for a plurality of patients; accessing status of cardiac arrhythmia for the plurality of patients, wherein the status of cardiac arrhythmia for the plurality of patients was determined subsequent to a time when the historical cardiac signal patient data was recorded; and training the first machine learning process based on the historical cardiac signal patient data and the status of cardiac arrhythmia to infer an onset of cardiac arrhythmia, wherein the user is different than the plurality of patients.

In some implementations, the hardware processor is further configured to apply a second machine learning process, wherein the second machine learning process has been trained to remove or detect noisy segments or artifacts from the detected cardiac signals of the user, wherein the first machine learning process receives as input the cardiac signals where the noisy segments or artifacts have been removed. In some implementations, the hardware processor is further configured to apply a second machine learning process, wherein the second machine learning process has been trained to mitigate noise from the detected cardiac signals of the user, wherein the first machine learning process receives as input the cardiac signals where the noise has been mitigated. In some implementations, the onset of cardiac arrhythmia comprises a probability of ascertaining cardiac arrythmia at a later time. In some implementations, at least a portion of the historical cardiac signal patient data does not indicate cardiac arrhythmia at a time of recording the historical cardiac signal patient data. In some implementations, the first machine learning process is further configured to process photoplethysmography (PPG) data, heartbeat or acceleration data to infer the onset of cardiac arrythmia. In some implementations, the cardiac arrhythmia comprises at least one of: ventricular tachycardia, supraventricular tachycardia, ectopy, or ventricular fibrillation. In some implementations, the computing system comprises a wearable smart watch. In some implementations, the sensor is an electrode.

Some implementations include an electronic device for monitoring physiological signals in a user, the electronic device comprising: an adhesive assembly comprising a housing and a flexible wing, the housing enclosing a circuit board, a flexible wing extending from the housing and configured to conform to a surface of the user; a sensor coupled to the flexible wing, the sensor in electrical communication with the circuit board and being configured to be positioned in conformal contact with the surface of the user to detect physiological signals; and one or more hardware processors configured to apply the detected physiological signals to a machine learning process, wherein the machine learning process is configured to infer an onset of cardiac arrhythmia based on the detected physiological signals, wherein the machine learning process is trained by: accessing historical cardiac signal patient data for a plurality of patients; accessing status of cardiac arrhythmia for the plurality of patients, wherein the status of cardiac arrhythmia for the plurality of patients was determined subsequent to a time when the historical cardiac signal patient data were recorded; and training the machine learning process based on the historical cardiac signal patient data and the status of cardiac arrhythmia to infer an onset of cardiac arrhythmia, wherein the user is different than the plurality of patients.

In some implementations, to infer an onset of cardiac arrhythmia comprises generating a risk score for cardiac arrhythmia at a time subsequent to the physiological signals being detected by the sensor. In some implementations, the one or more hardware processors are further configured to, prior to inferring the onset of cardiac arrhythmia, determine that cardiac arrhythmia is not currently present in the detected physiological signals. In some implementations, to infer the onset of cardiac arrhythmia is in response to determining that cardiac arrhythmia is not currently present in the detected physiological signals. In some implementations, the one or more hardware processors are further configured to adjust a function of the electronic device based on the inferred onset of cardiac arrhythmia. In some implementations, to adjust the function of the electronic device comprises adjusting a window of physiological signals being processed by the electronic device. In some implementations, in response to the risk score meeting a threshold score, the one or more hardware processors are further configured to transmit an alert to a device of the user or a physician. In some implementations, the one or more hardware processors are further configured to recommend a treatment or intervention for the onset of cardiac arrhythmia. In some implementations, to recommend the treatment or intervention is based on clustering prior patient data. In some implementations, the clusters include a plurality of centroids, wherein the one or more hardware processors apply a distance process from the centroids of corresponding clusters to a record of the user to recommend the treatment. In some implementations, the clustering process clusters patients based on a status of cardiac arrhythmia, an intervention type, and outcomes of the application of the intervention type.

Some implementations include a method of training a machine learning process to infer an onset of cardiac arrhythmia, the method comprising: accessing historical cardiac signal patient data for a plurality of patients, wherein at least a portion of the historical cardiac signal patient data of cardiac signals do not indicate cardiac arrhythmia at the time of recording the cardiac signals; accessing status of cardiac arrhythmia for the plurality of patients, wherein the status of the plurality of patients was determined subsequent to a time when the cardiac signals were recorded; and training a first machine learning process based on the historical cardiac signal patient data and the status of cardiac arrhythmia to infer an onset of cardiac arrhythmia, wherein the user is different than the plurality of patients.

In some implementations, training the first machine learning process further comprises training the first machine learning process to infer hospitalization, heart failure onset, the onset of a stroke, or a death condition. In some implementations, the method further comprises training a second machine learning process to infer hospitalization, heart failure onset, the onset of a stroke or a death condition, wherein the input to the second machine learning process includes cardiac signals of a longer duration than inputted cardiac signals for the first machine learning process. In some implementations, the method further comprises determining an atrial fibrillation burden from the detected cardiac signals, wherein the atrial fibrillation burden comprises an amount of time spent in atrial fibrillation by the user during a period of time.

Some implementations include a method comprising: detecting cardiac signals from a user; and applying the detected cardiac signals to a first machine learning process, wherein the first machine learning process is configured to infer an onset of cardiac arrhythmia based on input data, wherein the first machine learning process is trained by: accessing historical cardiac signal patient data for a plurality of patients; accessing status of cardiac arrhythmia for the plurality of patients, wherein the status of the plurality of patients was determined subsequent to a time when the historical cardiac signal patient data were recorded; and training the first machine learning process based on the historical cardiac signal patient data and the status of cardiac arrhythmia to infer an onset of cardiac arrhythmia of a user, wherein the user is different than the plurality of patients.

These and other aspects and implementations of the invention are described in greater detail below, with reference to the drawing figures.

BRIEF DESCRIPTION OF THE DRAWINGS

FIG. 1A depicts a perspective view of the physiological monitoring device. FIG. 1B depicts an exploded view of the physiological monitoring device.

FIG. 2A shows a top perspective view, FIG. 2B shows a bottom view, FIG. 2C shows a top perspective view including liners, FIG. 2D shows a bottom view including liners.

FIGS. 3A-3H illustrate various views of examples of a physiological monitoring device. FIG. 3A depicts a perspective view, FIG. 3B shows a top view, FIG. 3C shows a bottom view, and FIG. 3D1 depicts a side view. FIG. 3D2 depicts a side view of a ridge configured for sealing the top and bottom portions of the housing. FIGS. 3E and 3F show a bottom and a top view of the physiological monitoring device with the layers illustrated transparently, to provide visualization through the device. FIGS. 3G and 3H illustrate exploded views of the various components of the physiological monitoring device.

FIGS. 12A and 12B illustrate an implementation of a report of a patient with AF identified in the recording of the cardiac monitor.

FIG. 13C illustrates an example implementation of a flow diagram for training an encoder, decoder, and machine learning model using historical patient cardiac data to infer an onset of cardiac arrhythmia.

DETAILED DESCRIPTION OF IMPLEMENTATIONS

Figure 1A:
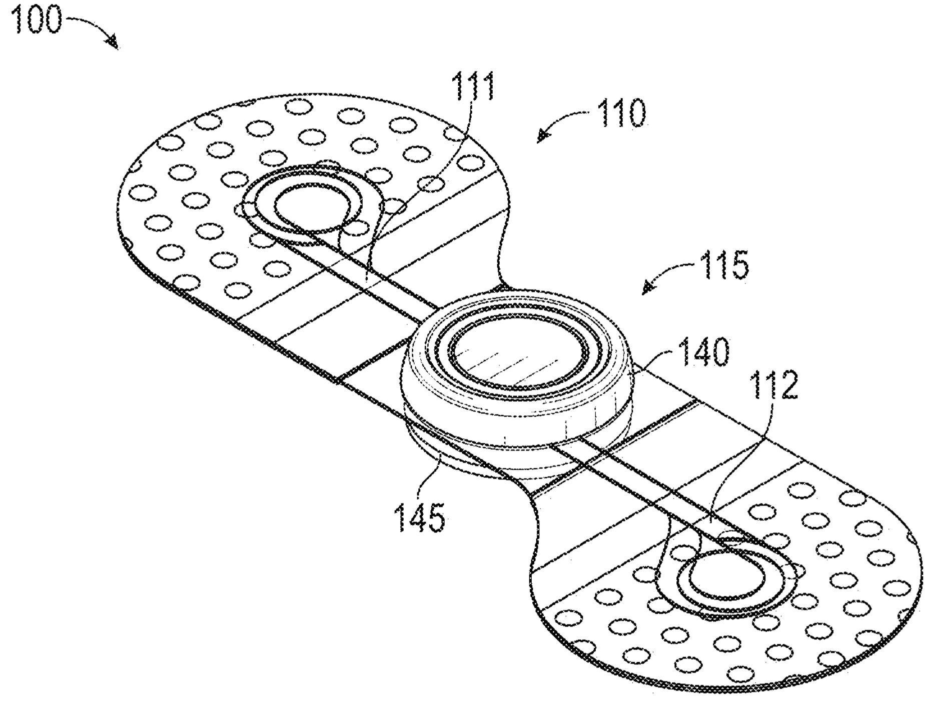
FIGS. 1A-1B illustrate multiple views of an example of a physiological monitoring device.

The following description is directed to a number of various implementations. The described implementations, however, may be implemented and/or varied in many different ways. For example, the described implementations may be implemented in any suitable device, apparatus, or system to monitor any of a number of physiological parameters. For example, the following discussion focuses primarily on long-term, patch-based cardiac rhythm monitoring devices. In one alternative implementation, a physiological monitoring device may be used, for example, for pulse oximetry and diagnosis of obstructive sleep apnea. The method of using a physiological monitoring device may also vary. In some cases, a device may be worn for one week or less, while in other cases, a device may be worn for at least seven days and/or for more than seven days, for example between fourteen days and twenty-one days or even longer.

Since abnormal heart rhythms or arrhythmias can often be due to other, less serious causes, a key challenge is to determine when any of these symptoms are due to an arrhythmia. Oftentimes, arrhythmias occur infrequently and/or episodically, making rapid and reliable diagnosis difficult. Currently, cardiac rhythm monitoring is primarily accomplished through the use of devices, such as Holter monitors, that use short-duration (less than 1 day) electrodes affixed to the chest. Wires connect the electrodes to a recording device, usually worn on a belt. The electrodes need daily changing and the wires are cumbersome. The devices also have limited memory and recording time. Wearing the device interferes with patient movement and often precludes performing certain activities while being monitored, such as bathing. Further, Holter monitors are capital equipment with limited availability, a situation that often leads to supply constraints and corresponding testing delays. These limitations severely hinder the diagnostic usefulness of the device, the compliance of patients using the device, and the likelihood of capturing all important information. Lack of compliance and the shortcomings of the devices often lead to the need for additional devices, follow-on monitoring, or other tests to make a correct diagnosis.

Current methods to correlate symptoms with the occurrence of arrhythmias, including the use of cardiac rhythm monitoring devices, such as Holter monitors and cardiac event recorders, are often not sufficient to allow an accurate diagnosis to be made. In fact, Holter monitors have been shown to not lead to a diagnosis up to 90% of the time ("Assessment of the Diagnostic Value of 24-Hour Ambulatory Electrocardiogramonitoring", by DE Ward et al. Biotelemetry Patient Monitoring, vol. 7, published in 1980).

Additionally, the medical treatment process to actually obtain a cardiac rhythm monitoring device and initiate monitoring is typically very complicated. There are usually numerous steps involved in ordering, tracking, monitoring, retrieving, and analyzing the data from such a monitoring device. In most cases, cardiac monitoring devices used today are ordered by a cardiologist or a cardiac electrophysiologist (EP), rather than the patient's primary care physician (PCP). This is of significance since the PCP is often the first physician to see the patient and determine that the patient's symptoms could be due to an arrhythmia. After the patient sees the PCP, the PCP will make an appointment for the patient to see a cardiologist or an EP. This appointment is usually several weeks from the initial visit with the PCP, which in itself leads to a delay in making a potential diagnosis as well as increases the likelihood that an arrhythmia episode will occur and go undiagnosed. When the patient finally sees the cardiologist or EP, a cardiac rhythm monitoring device will usually be ordered. The monitoring period can last 24 to 48 hours (Holter monitor) or up to a month (cardiac event monitor or mobile telemetry device). Once the monitoring has been completed, the patient typically must return the device to the clinic, which itself can be an inconvenience. After the data has been processed by the monitoring company or by a technician on-site at a hospital or office, a report will finally be sent to the cardiologist or EP for analysis. This complex process results in fewer patients receiving cardiac rhythm monitoring than would ideally receive it.

To address some of these issues with cardiac monitoring, the assignee of the present application developed various implementations of a small, long-term, wearable, physiological monitoring device. One implementation of the device is the Zio® Patch and Zio® Monitoring platform/systems. Various implementations are also described, for example, in U.S. Pat. Nos. 8,150,502, 8,160,682 8,244,335, 8,560,046, 8,538,503, 9,597,004, and 11246524 the full disclosures of which are hereby incorporated herein by reference. Generally, the physiological patch-based monitors described in the above references fit comfortably on a patient's chest and are designed to be worn for at least one week and typically two to three weeks. The monitors detect and record cardiac rhythm signal data continuously while the device is worn, and this cardiac rhythm data is then available for processing and analysis.

Physiological Monitoring Devices

Figure 1B:
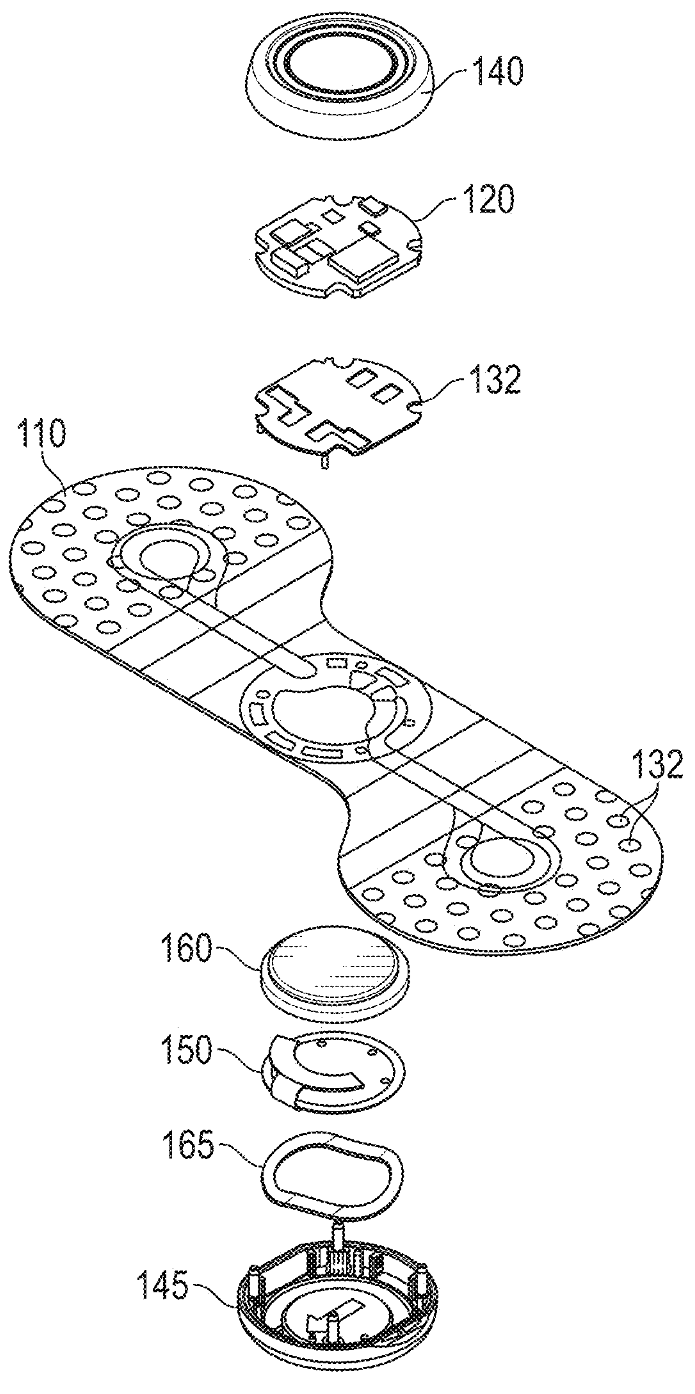

FIGS. 1A-1B illustrate multiple views of another example of a physiological monitoring device 100, such as the features described in U.S. Pat. Nos. 11,350,864 and 11,337,632, which are incorporated by reference in their entirety. The physiological monitoring device 100 may comprise one or more of the components described elsewhere herein. The physiological monitoring device 100 may comprise a housing 115 comprising an upper housing 140 and a lower housing 145 which are configured to mate together sandwiching a flexible body 110 between the upper housing 140 and the lower housing 145. The flexible body 110 may comprise the trace layer 109 and one or more substrate layers forming the wings of the physiological monitoring device 100. The wings may comprise adhesive layers 140 and electrodes 150 as described elsewhere herein. The rigid body and/or housing 115 may enclose a PCBA 120, a flexible upper frame 142, a battery 160, a battery terminal connector 150, a portion of the trace layer 109, a spring contact spacer 132, and a spring 165.

FIG. 1A depicts a perspective view of an example of the physiological monitoring device 100. FIG. 1B depicts an exploded view of the physiological monitoring device 600.

The upper housing 140 and the lower housing 145 may sandwich the flexible body 110 as described elsewhere herein. In some examples, the flexible body 110 may comprise one or more apertures 132 through extending through one or more of the substrate layers to provide breathability and moisture management and/or to facilitate drug delivery to the skin of the surface, as described elsewhere herein. An upper gasket layers 160 and/or a lower gasket layer 170 (not shown) may be provided on opposite sides of the flexible body 110 (not shown). The gasket layers 160, 170 may be adhesive for adhering to the flexible body 110. A compressible seal may be formed above and/or below the flexible body 110. In some implementations, a compressive seal may be formed with the flexible upper frame 142. The battery 160 may be positioned below the flexible body 110 comprising the trace layer 109. The PCBA 120 may be positioned above the flexible body 110 comprising the trace layer 109. A battery terminal connector 150 may be adhered or otherwise coupled to the battery 160 such that first and second battery traces 152, 153 are exposed on an outer surface of the battery terminal connector 150 on a top side of the battery 160. The first and second battery traces 152, 153 may be exposed to the internal volume of the upper housing 140 through a large central opening in the housing area of the trace layer 109.

Electrical contact between the PCBA 120 and the first and second battery traces 152, 153 and/or electrical contact between the PCBA 120 and the electrocardiogram interface portions 113 of the electrical traces 111, 112 may be established by spring contacts 137. The spring contacts 137 may be coupled to the bottom surface of the PCBA 120. The housing 115 may comprise a spring contact spacer 132 positioned below the PCBA 120. In some examples, the spring contact spacer 132 may be rigidly affixed (e.g., adhered) to the bottom of the PCBA 120. In examples, the spring contact spacer may be attached or integrated into the flexible body 110. In some examples, the spring contact spacer may be integrated into the battery terminal connector. The spring contact spacer 132 may comprise a flat body and a plurality of downward extending legs 133. The legs 133 may be configured to be seated against a top surface and/or a lateral surface of the battery 160, such that the spring contact spacer 132 maintains a minimum separation distance between the battery 160 and the PCBA 120 and provides sufficient space for the spring contacts 137. The spring contact spacer 132 may comprise one or more holes 134 through which the spring contacts 137 may extend downward from the bottom surface of the PCBA 120. The lower housing 145 may comprise a spring 165, as described elsewhere herein positioned below the battery 160. The spring 165 may bias the battery 160 upward and may bias the first and second battery traces 152, 153 into physical and electrical contact with corresponding spring contacts 137. The electrocardiogram interface portions 113 of the traces 111, 112 may be seated on a top side of the battery 160 such that biasing the battery 160 upward also biases the electrocardiogram interface portions 113 of the traces 111, 112 into physical and electrical contact with corresponding spring contacts 137. The substantially consistent spacing between the traces and the PCBA 120 provided by the spring 165 and the spring contact spacer 132 may reduce, minimize, or eliminate noise in the electrical signal caused by fluctuating degrees of electrical contact between the spring contacts 137 and the traces. The assembly may comprise at least one spring contact 137 for each of the first battery trace 152, second battery trace 153, first electrical trace 111, and second electrical trace 112. The assembly may comprise more than one spring contacts 137 for some or all of the traces. The spring contacts 137 may be configured under compression induced by the arrangement of the various components, including spring 165, to establish an electrical pathway between each of the traces and the PCBA 120. The compressive contact between the spring contacts 137 and the traces may be maintained even under nominal changes in the separation distances between the traces and the PCBA 120 (e.g., caused by movement) since the spring contacts 137 may extend further downward if the separation distance increases and the biasing corresponding decreases. In some examples, the first and second battery traces 152, 153 may be configured to be positioned on an opposite side of the housing 115 from the first and second electrical traces 111, 112. In some examples, the spring contacts may be configured to carry electrical signals from battery or electrocardiogram signals by contacting electrical traces applied to the upper housing 140 or the bottom housing 145. These electrical traces may be applied to the housings through the use of laser direct structuring, plating to a palatable substrate applied in a secondary mold process, or printing via aerosol jet, inkjet or screen printing of conductive materials. In some examples, RF antennas for wireless communication (such as Bluetooth) could be configured through the use of such electrical traces in the top housing 140 or bottom housing 145.

FIGS. 2A-2D depict multiple views of an example of a physiological monitoring device 200, similar to the physiological monitoring devices depicted in FIGS. 1A-1B. Here, the physiological monitoring device includes a central housing 202, comprising an upper housing 202 and a lower housing 206 sandwiched over flexible substrate 210. One of skill in the art will understand that the housing may be constructed from any suitable material disclosed herein, such as a rigid polymer or a soft, flexible polymer. In some examples, the housing may include an indicator 208, which may be in any suitable shape such as an oval, a circle, a square, or a rectangle. The indicator may comprise an LED light source (not shown) or any suitable light source, which may be overlain by a transparent or translucent viewing layer positioned against the inner surface of the upper housing. The viewing layer may be constructed from thermoplastic polyurethane or any suitable material. The indicator may be used to indicate a status of the physiological monitoring device such as the battery life of the physiological monitoring device. In some examples, the indicator may indicate whether the physiological monitoring device is collecting data, transmitting data, paused, experiencing an error, or analyzing data. The indicator may display any suitable color, for example red, amber, or green.

Extending outward from the housing are a plurality of wings 212. One of skill in the art will understand that although two wings are depicted here, some examples of the physiological monitoring device 200 may include more than two wings. As explained elsewhere in the specification, the wings may be shaped in such a way to improve adhesion to the skin and retention of the physiological monitoring device against the skin. In examples, the wings may asymmetric, with a greater portion of one wing (an upper lobe) 214 lying above the longitudinal line and a greater portion of another wing lying (a lower lobe) 216 below the longitudinal line, thereby allowing the physiological monitoring device to be positioned diagonally over the heart such that the lower lobe is positioned lower than the heart when a patient is in a standing position.

Figure 2A:
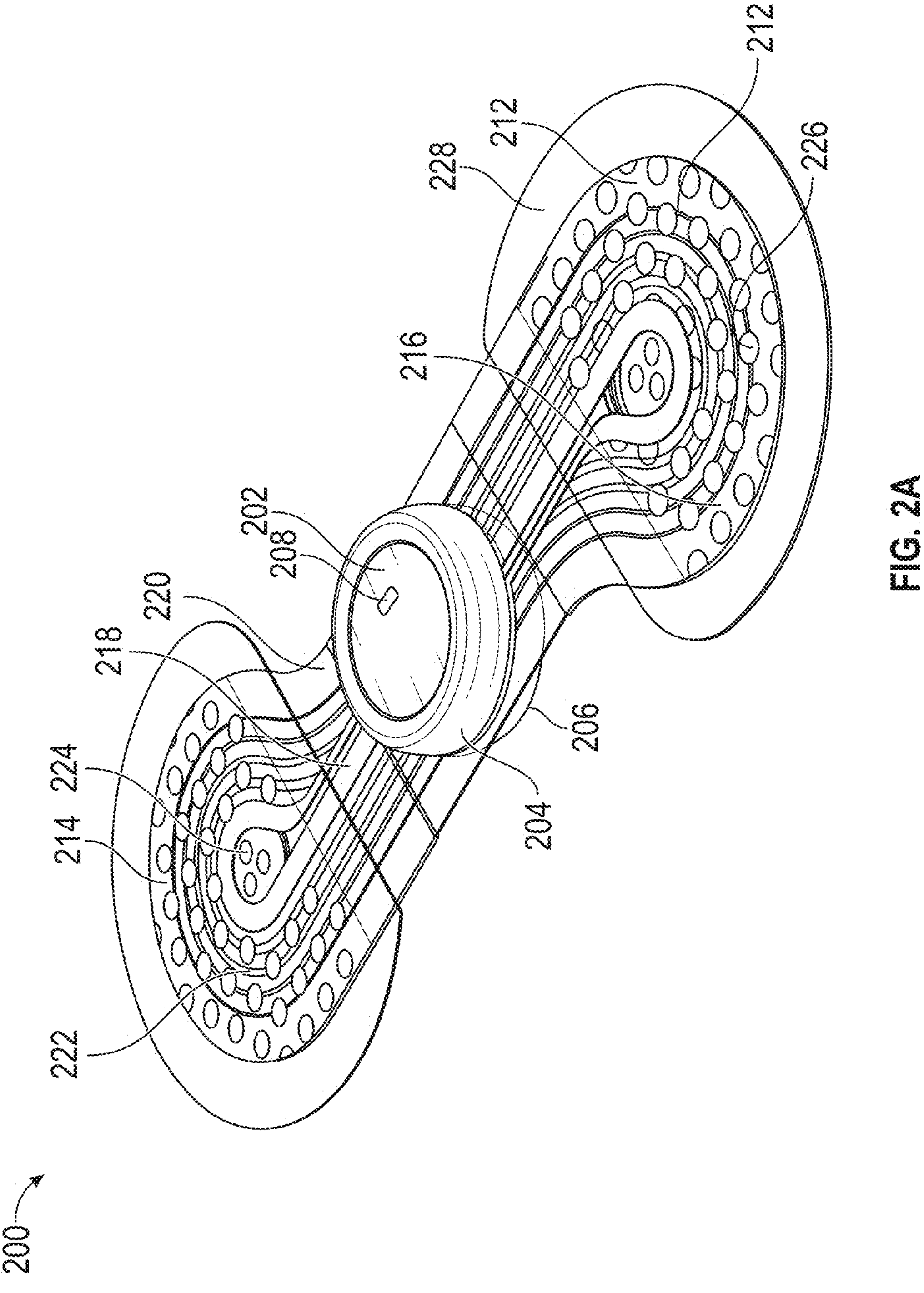
FIGS. 2A-2D illustrate multiple views of examples of a physiological monitoring device.
Figure 2B:
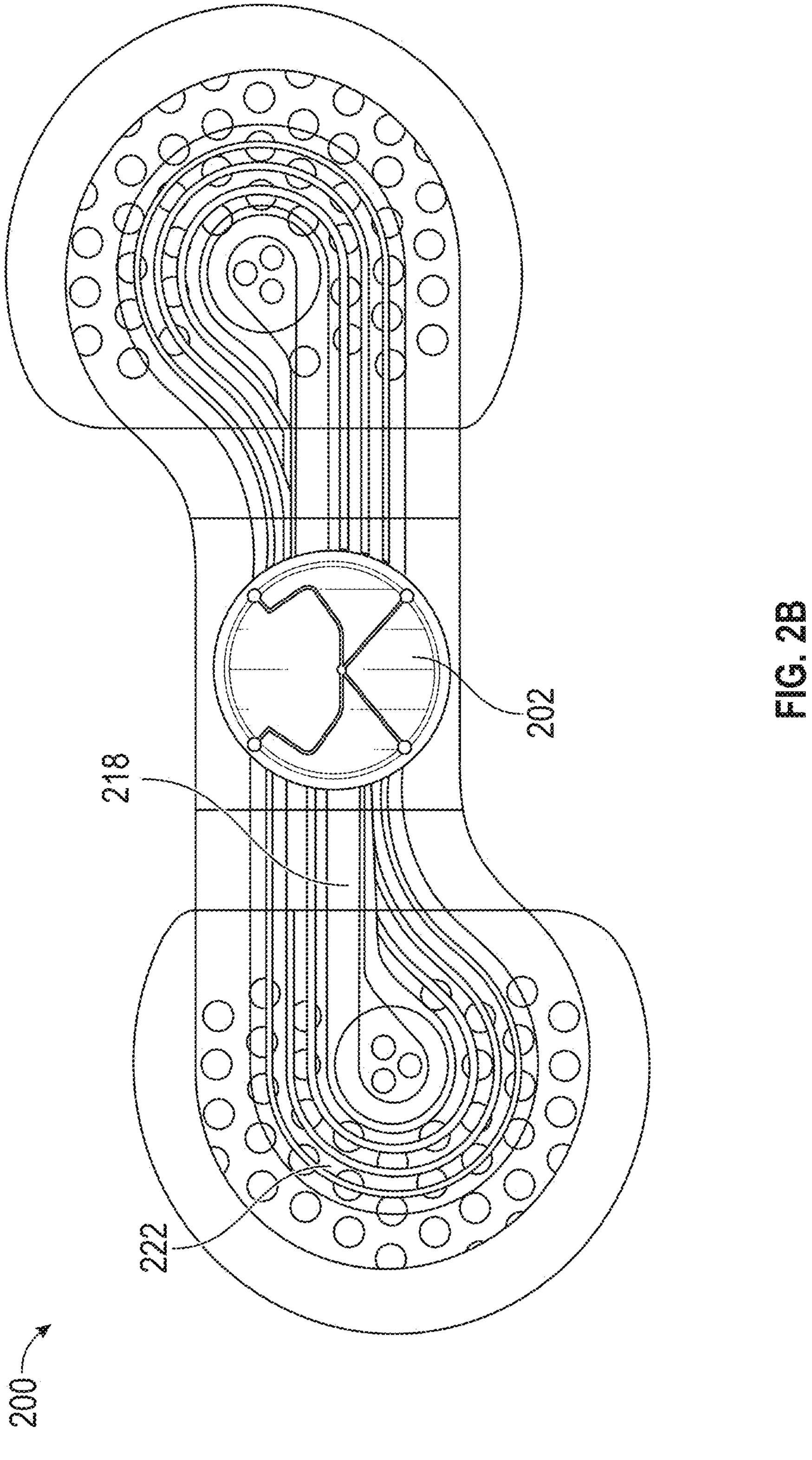
Figure 2C:
Figure 2C:
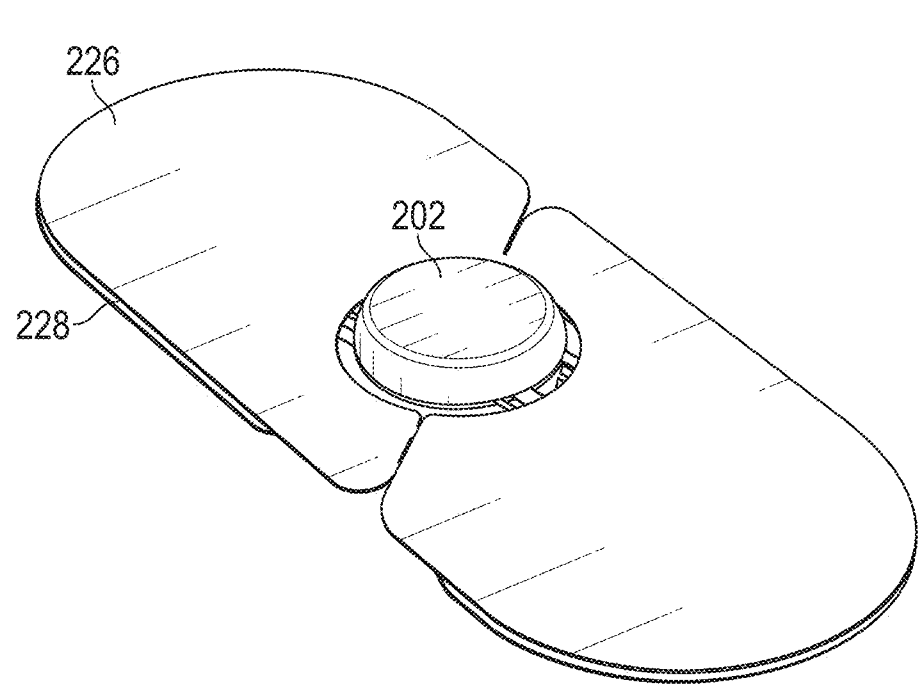
Figure 2D:
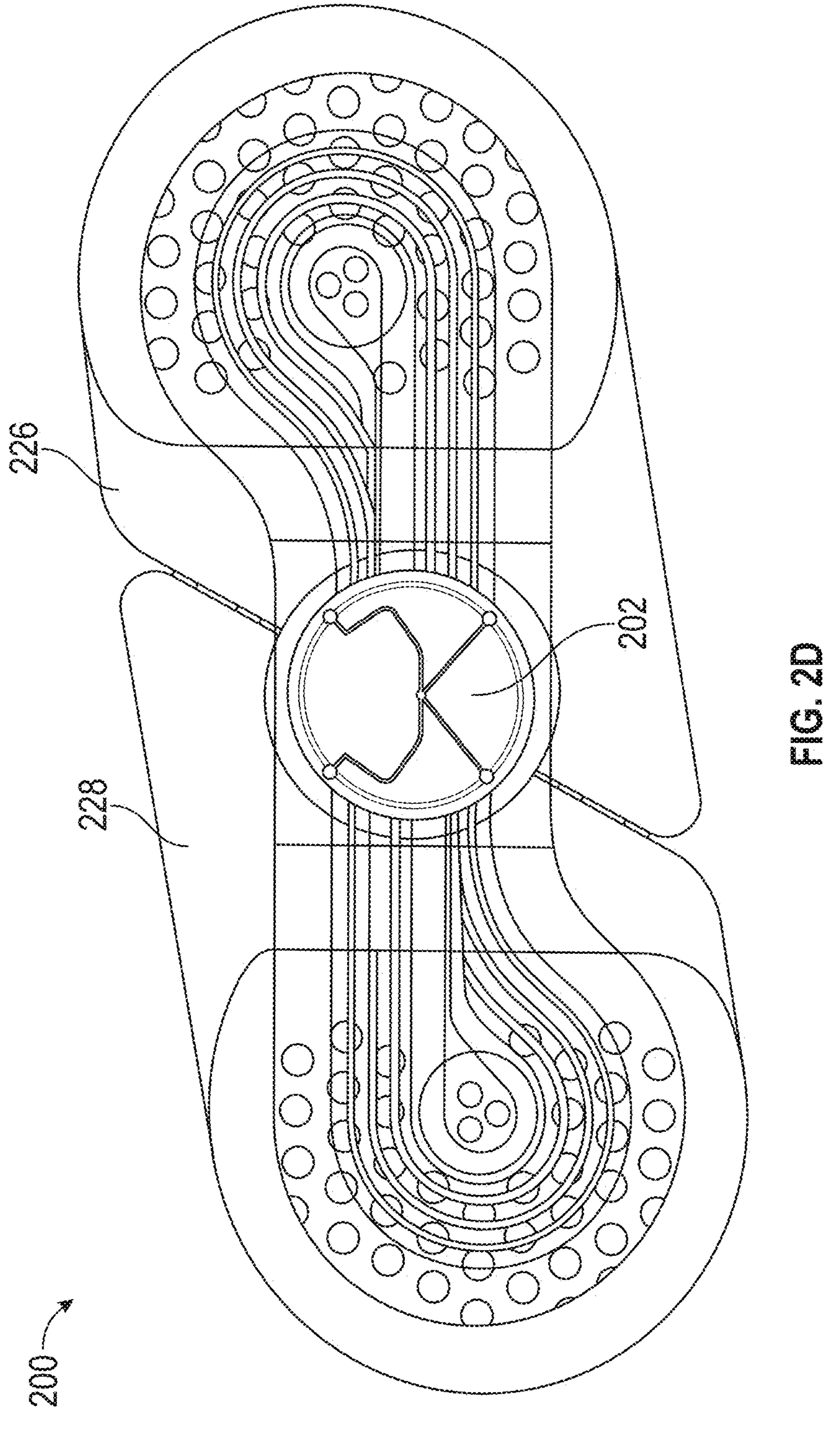

Extending outward from the housing and contained on or within the wings are electrode traces 218, similar to the electrode traces described elsewhere in the specification, such as with respect to FIG. 1A. As explained elsewhere in the specification, the electrode traces may be printed directly on a flexible substrate which may be part of a multi-layer flexible assembly 220. Additional printed lines 222 may surround the electrode trace 218 for visual enhancement of the physiological monitoring device, however said printed lines 222 may be printed on a different layer than the flexible substrate on which the electrode traces are printed. The printed lines may be printed such that they blend with the shape of the electrode trace. As explained elsewhere in the specification, the electrode trace may encircle a series of breathing holes 224 which allow for air passage to an underlying hydrogel. In examples, there may be one, two, three, four, or more breathing holes. As explained elsewhere in the specification, apertures 226 may extend through one or more layers of the physiological monitoring device to provide breathability and moisture management. In examples, an adhesive border layer 228 may extend outward from the wings, thereby allowing for improved adhesion. FIG. 2B depicts the underside of the physiological monitoring device 200 depicted in FIG. 2A. Here, lower housing 206 is clearly visible as are the electrode traces 218 and printed lines 222 extending outward from the housing. FIGS. 2C and 2D depict the physiological monitoring device 200 of FIGS. 2A-2B, here including an externally facing top liner 226 and skin facing patient release liner 228 overlying the wings and surrounding the housing 202. Such release liners serve to protect the physiological monitoring device 200 during storage, in particular to protect the adhesive surfaces of the physiological monitoring device. In examples, the liners may be shaped such that two sides meet to form an opening for the housing to extend vertically past the liners.

In some implementations, an abrader may be used to abrade the skin of the patient prior to adhesion of the physiological monitoring device 200 (such as described elsewhere in the specification) to the patient. The abrader may be used to remove a top layer of skin from the patient to improve long-term adhesion of the physiological monitoring device and/or signal quality form the physiological monitoring device.

In various alternative examples, the shape of a particular physiological monitoring device may vary. The shape, footprint, perimeter or boundary of the device may be circular, an oval, triangular, a compound curve or the like, for example. In some examples, the compound curve may include one or more concave curves and one or more convex curves. The convex shapes may be separated by a concave portion. The concave portion may be between the convex portion on the housing and the convex portion on the electrodes. In some examples, the concave portion may correspond at least partially with a hinge, hinge region or area of reduced thickness between the body and a wing.

While described in the context of a heart monitor, the device improvements described herein are not so limited. The improvements described in this application may be applied to any of a wide variety of physiological data monitoring, recording and/or transmitting devices. The improved adhesion design features may also be applied to devices useful in the electronically controlled and/or time released delivery of pharmacological agents or blood testing, such as glucose monitors or other blood testing devices. As such, the description, characteristics and functionality of the components described herein may be modified as needed to include the specific components of a particular application such as electronics, antenna, power supplies or charging connections, data ports or connections for down loading or off-loading information from the device, adding or offloading fluids from the device, monitoring or sensing elements such as electrodes, probes or sensors or any other component or components needed in the device specific function. In addition, or alternatively, devices described herein may be used to detect, record, or transmit signals or information related to signals generated by a body including but not limited to one or more of ECG, EEG and/or EMG. In certain examples, additional data channels can be included to collect additional data, for example, device motion, device flex or bed, heart rate and/or ambient electrical or acoustic noise.

The physiological monitors described above and elsewhere in the specification may further be combined with methods and systems of data processing and transmission that improve the collection of data from the monitor. Further, the methods and systems described below may improve the performance of the monitors by enabling timely transmission of clinical information while maintaining the high patient compliance and case-of-use of the monitor described above. For example, the methods and systems of data processing and transmission described herein this section of elsewhere in the specification may serve to extend the battery life of the monitor, improve the accuracy of the monitor, and/or provide other improvements and advantages as described herein this section or elsewhere in the specification.

Figure 3A:
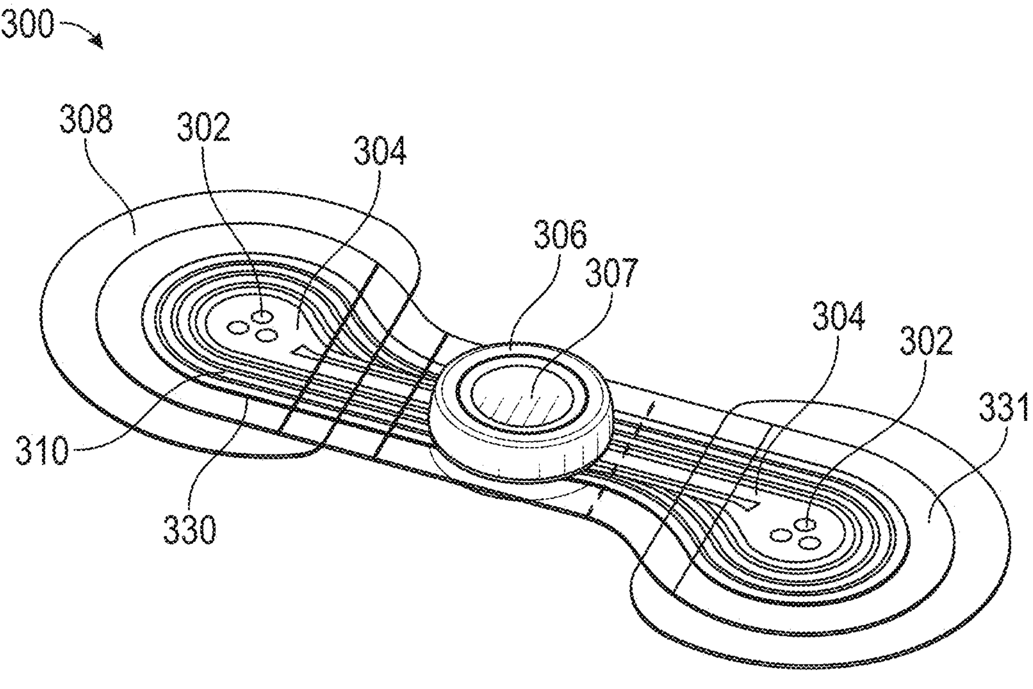
Figure 3B:
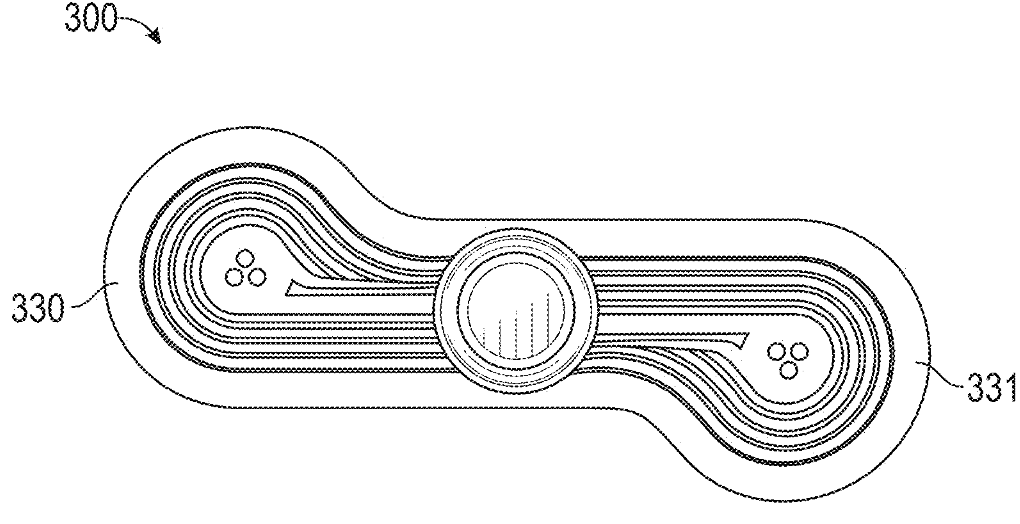
Figure 3C:
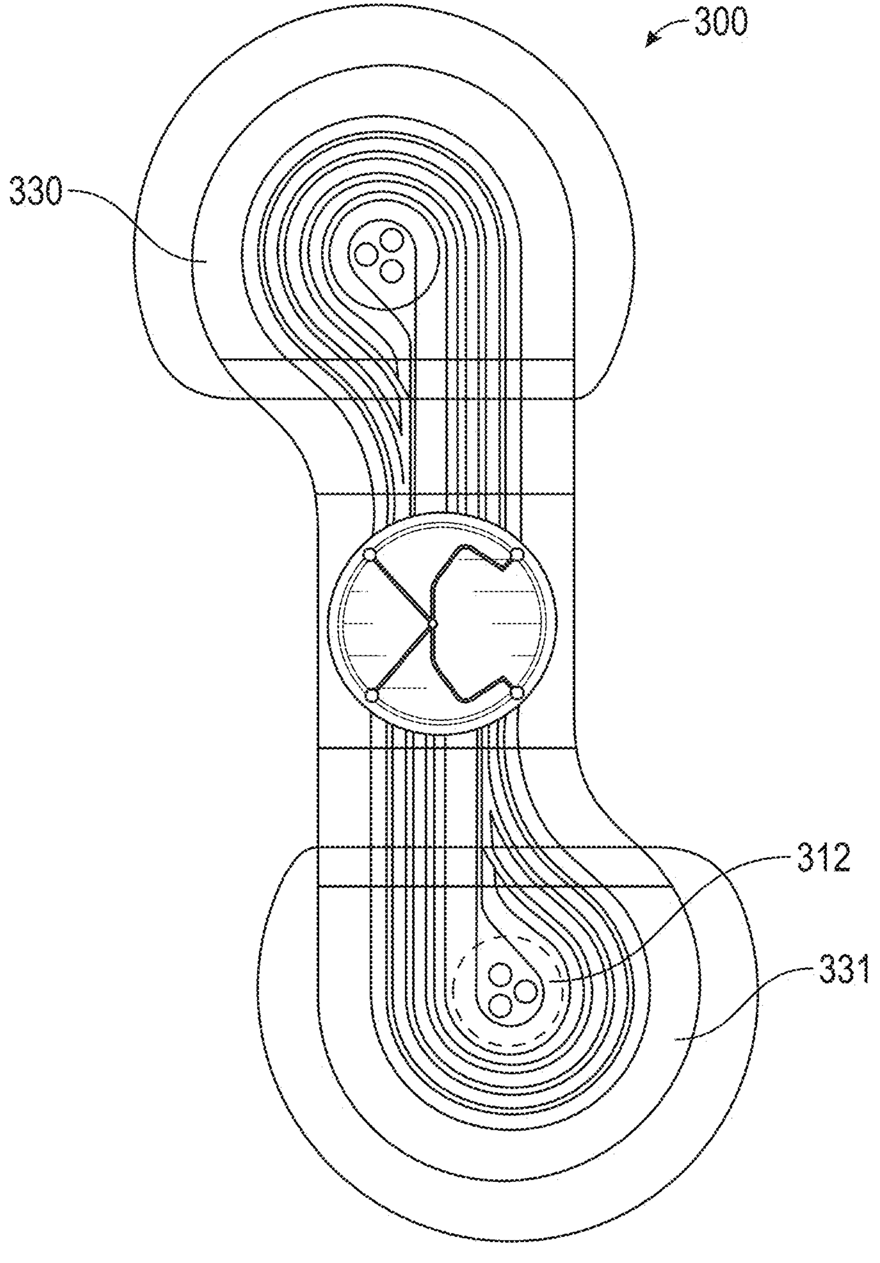

FIGS. 3A-3H depict an example of a physiological monitoring device 300, similar to the physiological monitoring devices depicted in U.S. Pat. No. 11,350,864, which is incorporated by reference in its entirety. FIG. 3A depicts a perspective view of the physiological monitoring device. The physiological monitoring device 300 may comprise wings 330, 331 which are each asymmetrical about a longitudinal axis approximately extending between the electrode interface portions 302 which overlie the electrodes positioned on the underside of the wings. Electrode traces 304, may extend from the housing to the electrodes, to provide electrical communication between the electrode and the central housing. One of the wings 330 may comprise a body which is disproportionately distributed above the longitudinal axis and the other wing 331 may comprise a body which is disproportionately distributed below the longitudinal axis. Therefore, the wings 330, 331, may make the flexible body asymmetric about a transverse axis, perpendicular to the longitudinal axis and extending through the housing 306, which may include patient trigger 307, similar to the other patient triggers disclosed herein this section or elsewhere in the specification. As described elsewhere herein, in certain examples, the patient trigger may encompass about: 10 to 30% of the total top area, such as about 20% of the top area or about 23% such as about 22.8% of the total top area. In certain examples, the patient trigger may encompass more than about 20%, more than about 30%, more than about 40%, more than about 50%, or more than about 75%. In certain examples, the patient trigger may encompass the entire top surface of the housing. The wings 330, 331 may comprise identical shapes which are reversed or flipped about both the longitudinal axis and the transverse axis as shown in FIGS. 3A-3C. In some examples, the wings may be asymmetrical in size and shape, for example the upper wing 330 may be larger than the lower wing 331 or vice-versa. The shapes of the wings 330, 331 may differ such that the relative shape of upper wing 330, differs from the relative shape of lower wing 331. In certain examples, the upper wing 330 may be under greater tension than the lower wing 331 or vice-versa, therefore different sizes and shapes between the two wings may aid in addressing unique force vectors during use of the physiological monitoring device. The configuration of the wings may be particularly suitable for positioning the electrodes in a diagonal arrangement with respect to the height of a subject, therefore potentially reducing peel off due to gravity. One of skill in the art will understand that the orientation of the wings may altered, such that the wings are mirrored, rather than being distributed disproportionately above or below a longitudinal axis. Further, those of skill in the art will understand that the shape of such wings, as described herein, may vary from the generally rounded shapes depicted in FIGS. 3A-3H. For example, the wings may be angular, such as a square shape, rectangular shape, triangular shape, pentagonal shape, or any suitable polygonal shape. These polygonal shapes may have rounded corners to reduce likelihood of peeling from the corner. A liner 308, such as depicted elsewhere herein may be used to cover and protect any adhesive, prior to application of the physiological monitoring device to a patient or user. In examples, the liner may be separated into two parts, one over each wing.

Figures 3E, 3F:
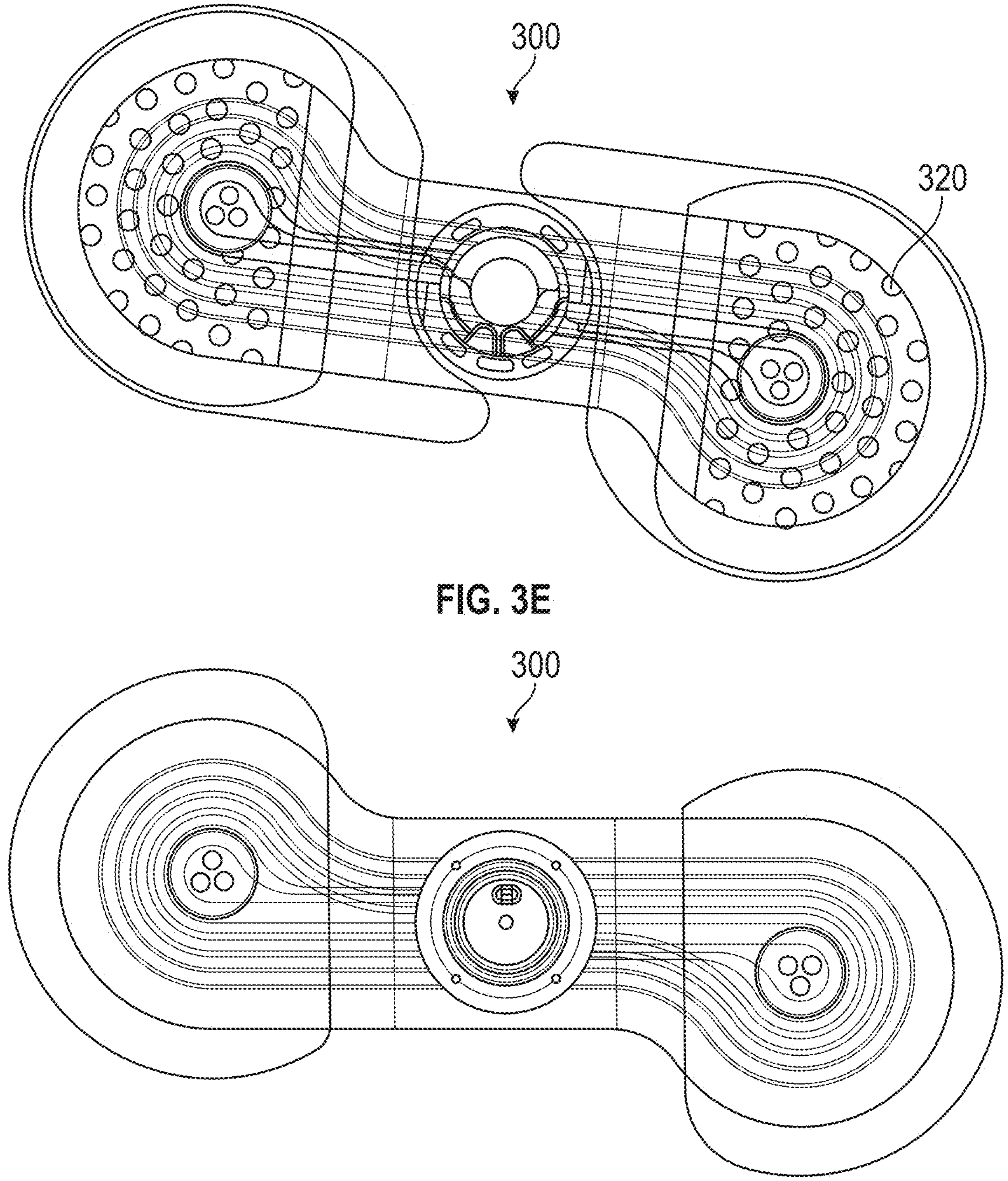

In certain examples, an additional visualization pattern 310 may extend through the wing. The visualization pattern 310 may be in any suitable size or shape to outline the electrode trace and frame the shape of the wings, for example, the visualization pattern 310 may be in the form of lines, such as rounded lines to reflect the contours of the electrode trace and the shape of the wings. In certain examples, there may be one, two, three, four, or more lines. In some examples, the visualization pattern may be formed from a pattern of dots, shapes or other combinations such that the visual cleanliness of the device is maintained as the otherwise clear adhesive layer becomes less visually acceptable to the user through the course of the wear period (e.g. if the adhesive layer picks up foreign material and/or becomes cloudy with absorption of moisture). In certain examples, the visualization pattern may have another functional purpose of alerting the user to how long they have been wearing the device, for example, by changing color over time or wearing down. This change in appearance may alert the user to remove the device at the right time. FIG. 3B shows a top view of an example of the physiological device 300, while FIG. 3C shows a bottom view, and FIG. 3D1 depicts a side view. In FIG. 3C, the flexible electrodes 312 are visible. As shown in FIG. 3D1, top 314 and bottom housing 316 portions of the housing may be positioned above and below the flexible body 318. FIGS. 3E and 3F show the underside and topside of the physiological monitoring device 300, with each layer transparent such that all layers are visible. Each layer will be described below in greater detail in the exploded view of the physiological monitoring device 300. Apertures 320 may be positioned in a substrate layer positioned above the adhesive layer. As described above in greater detail, such apertures may provide breathability through one or more layers and may promote transpiration of moisture from below the adhesive layer through the layer or layers comprising the apertures. As shown in FIG. 3D2, in examples, a gasket 319 may be positioned between the upper housing cover 314 and lower housing 316, co-molded into one or more of the housings. The gasket may compress down on the adhesive assembly and a ridged interface (shown below in FIG. 3D2) or another gasket on the opposite housing to provide waterproofing to the internal electronics hardware. As depicted in FIG. 3B2, a ridge 321 may be positioned on an upper edge of the lower housing 316, the ridge 321 configured to press into the adhesive layer 319. One of skill in the art will understand that the ridge 321 may be of any suitable shape, for example such as an edged ridge as depicted in FIG. 3D1. In some examples, the ridge may be rounded, square, and/or polygonal. In certain examples, the height of the ridge may be about 0.01 mm to 0.5 mm, about 0.05 mm to 0.4 mm, about 0.1 mm to 0.3 mm, about 0.1 mm to 0.2 mm, or about 0.15 mm such as about 0.13 mm.

Figure 3G:
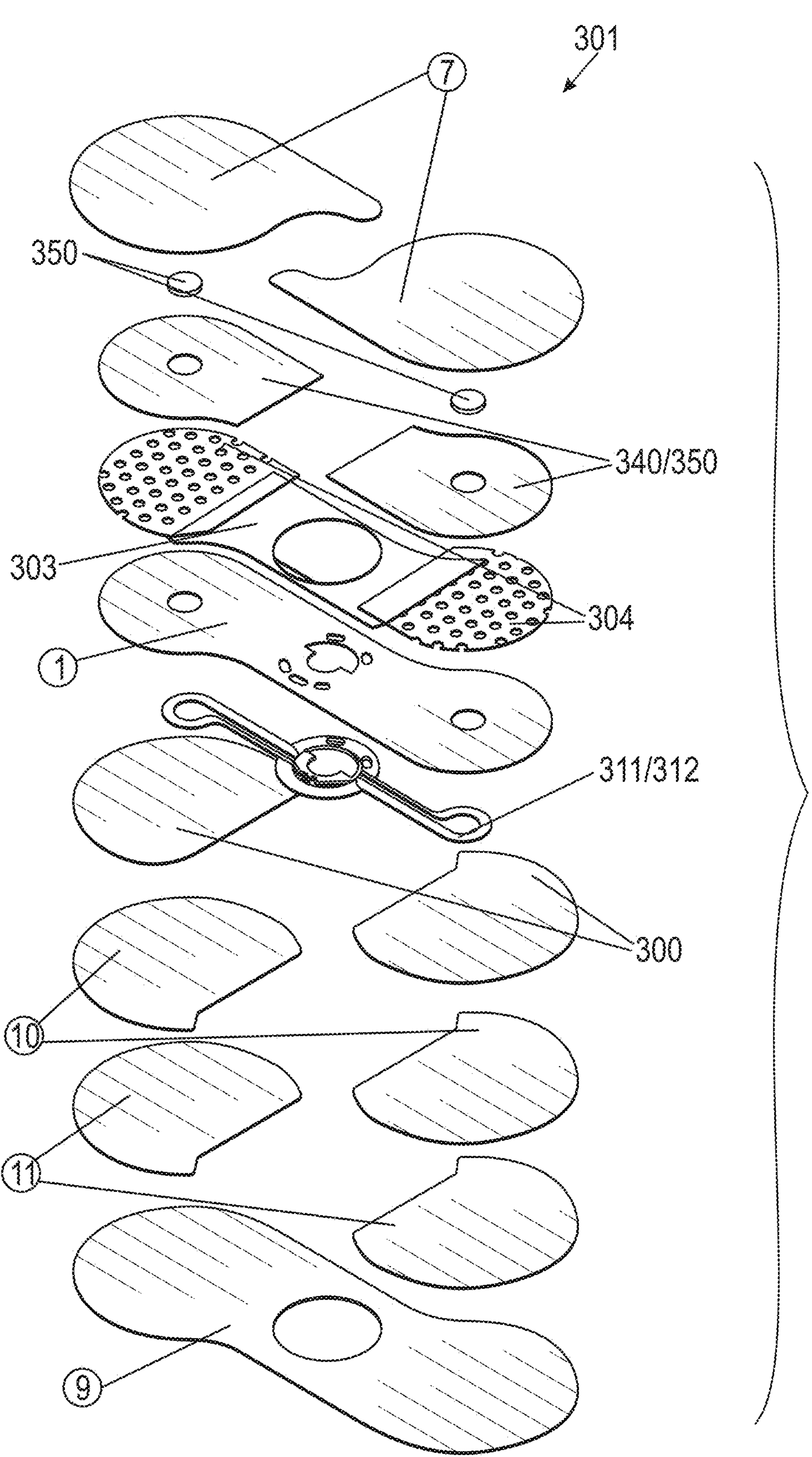

FIG. 3G depicts an exploded view of an example of flexible body 301 of the physiological monitoring device 300 described herein this section and elsewhere in the specification. The housing 306 is not shown. As will be understood by one of skill in the art, the image in FIG. 3G is oriented upside down in relation to positioning on the skin. Following the numbering within FIG. 3G, #7 depicts a release liner, which protects the adhesive layer (340 and hydrogel electrodes 350. Directly above the adhesive layer are a perforated layer 304 (containing apertures such as described herein) and a flap layer 303. In certain examples, the perforated layer and flap layers may be constructed from any suitable material, such as polyethylene terephthalate (PET) and/or polyurethane. Directly above the perforated layer may be a lower substrate layer #1, which may be constructed of polyurethane. In examples, the lower substrate layer may have at least one textured side, this side may be positioned such that the textured side faces flap layer #3. In examples, flap layer #3 may also include at least textured side. This textured side may be configured to face lower substrate layer #1. The conductive electrode traces may be printed on an additional, separate substrate (311,312). Or, in some examples, conductive electrode traces may be printed directly on the substrate layer #1. Positioned above the conductive electrode traces may be an upper substrate layer 300. Positioned over the upper substrate layer may be an additional carrier layer #10, followed by an adhesive layer #11 and a topmost rigid liner #9. One of skill in the art will understand that such an arrangement of layers may be applicable to any example of a physiological monitor described herein, such as the examples of FIGS. 3A-3F.

Figure 3H:
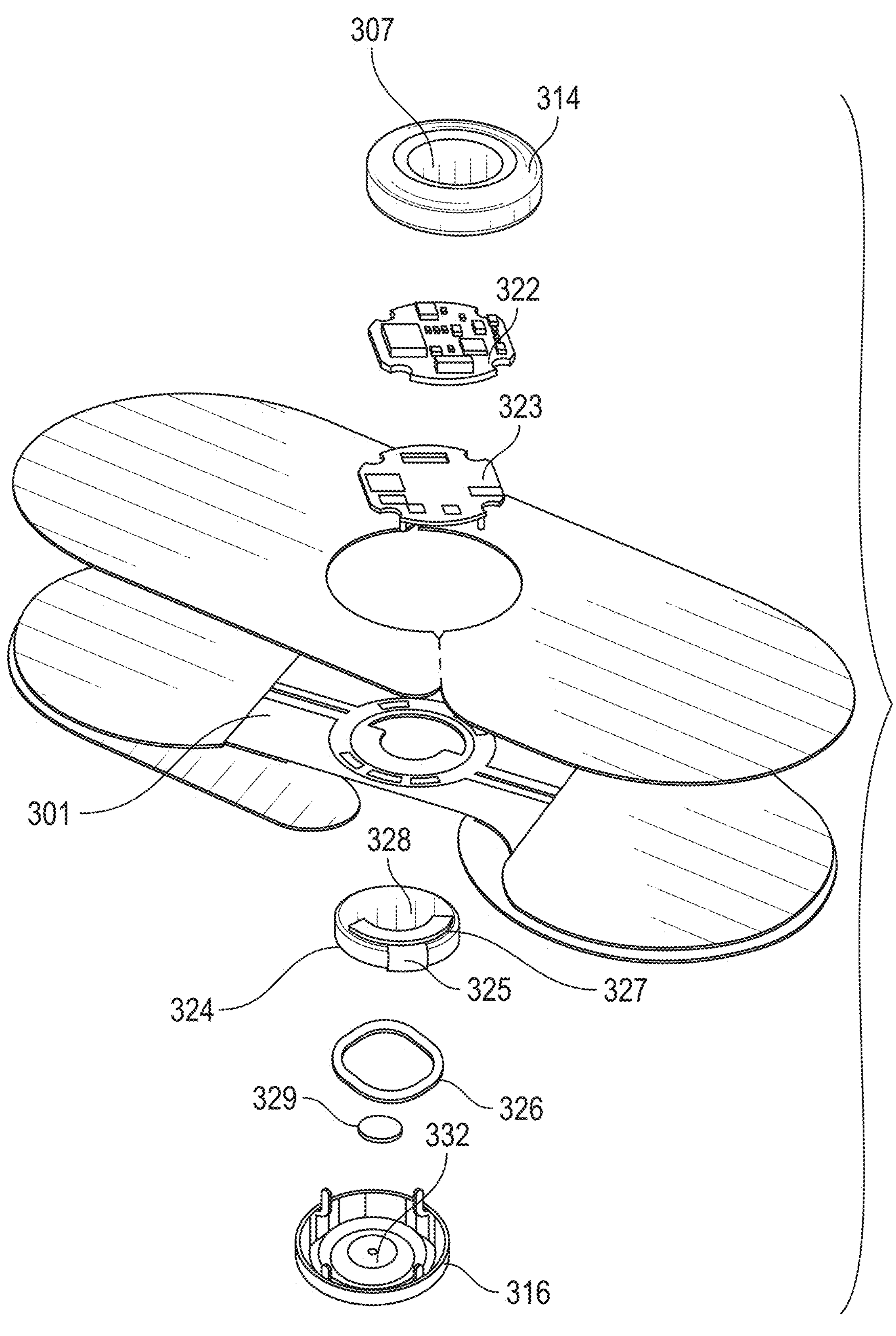

FIG. 3H depicts an exploded view of an example of the housing 306 of the physiological monitor device 300, through which passes flexible body 301, described in detail above. Top housing cover 314 may include a patient trigger 307. Top housing cover may encase circuit board 322. Spacer 323, positioned below the circuit board, is configured to maintain consistent spacing between the conductive contact springs that are on the underside of the circuit board and the battery terminals/ECG trace contacts. The spacer may additionally provide electrical insulation between the circuit board and battery. There may be holes in the spacer to allow conductive contact springs to pass through, the contact springs connected to the circuit board. Battery terminal 325, may be positioned below the flexible body 301 and circuit boards 322, thereby overlying wave spring 326. In examples, the battery terminal 325 may be wrapped around and adhered to a coin cell battery 328. The battery terminal 325 may be constructed as a flex circuit with conductive vias 327 that enables the positive underside of the coin cell battery 328 to be brought up to the negative top side of the battery, so that both the negative and positive terminals are presented on the top side of the battery to meet the circuit board contact springs. Alternatively, a battery contact or contacts in the bottom housing can enable the positive underside of the coin cell battery to be brought up to the negative top side to contact the circuit board. Venting layer 329 may be positioned against lower housing portion 316, over a vent hole 332 in the lower housing. In examples, the venting layer may be constructed from a material that blocks liquid passage while allowing gas passage, for example ePTFE or any other suitable material. The vent hole 332 in combination with the venting layer allows normalization of air pressure between the outside and inside of the housing. In examples, the vent hole 332 in combination with the venting layer prevents button and/or trigger 307 from blowing out or sucking in depending on external air pressure, for example if the patient is at a different altitude such as on a plane. The venting layer may be thin and round with adhesive in a ring configuration on the bottom. The area of the venting layer coated in adhesive may not be gas permeable, while the central portion may be gas permeable but liquid impermeable. The central portion of the venting layer may be positioned over the vent hole, thereby allowing gas passage into and out of the housing while limiting liquid egress and ingress. In certain examples, the venting layer may be integrated into the bottom housing by molding it in, or it could also be ultrasonically welded into the bottom housing, or adhered via any suitable means.

Figure 4A:
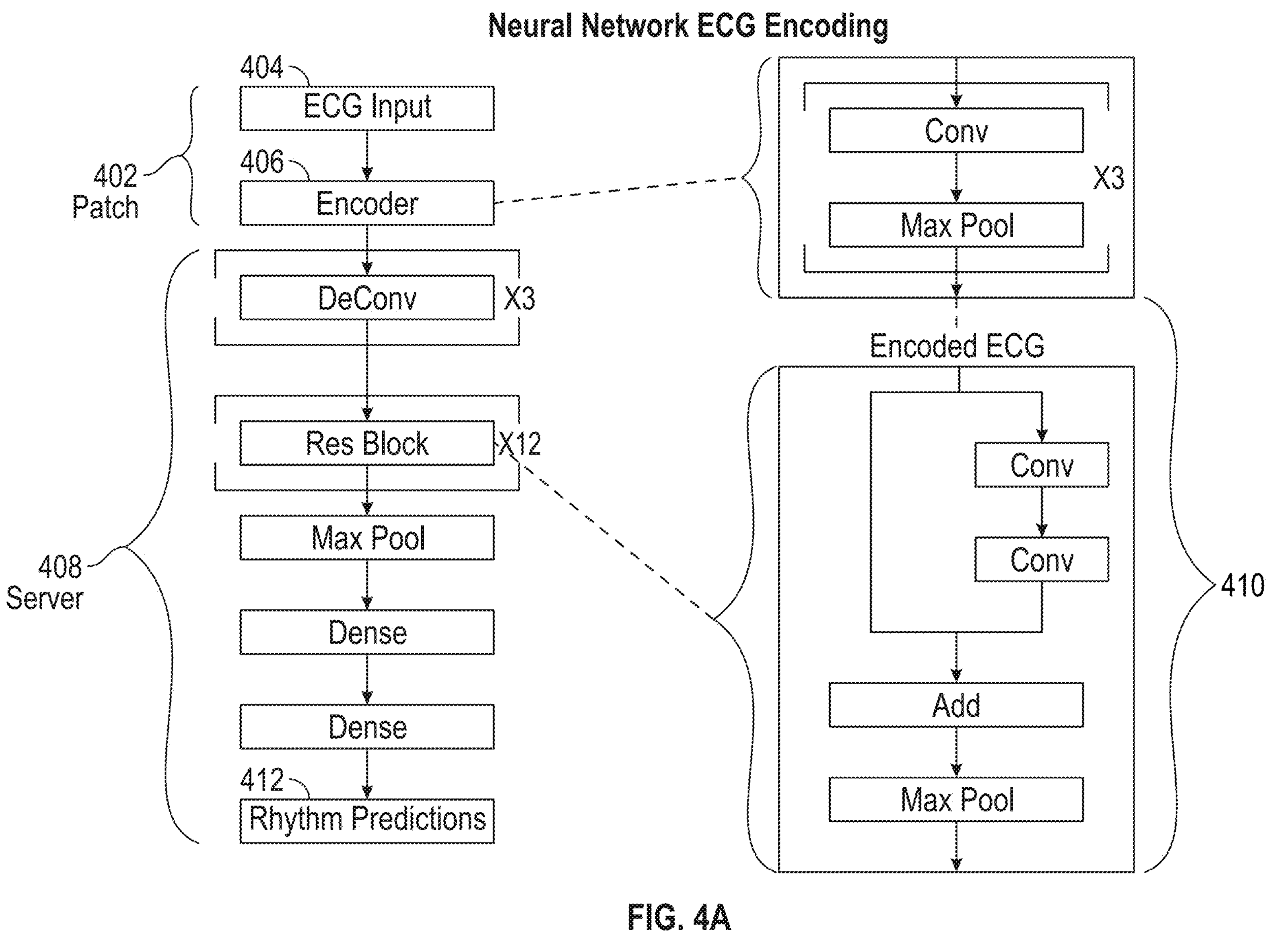
FIG. 4A is a schematic diagram of an implementation of a system for predicting rhythm annotations using neural network encoding.

Systems for Estimating Burden and/or predicting rhythm annotations using Neural Network Encoding Some implementations disclose a wearable device that can process the detected bio-signals through an encoder that includes a first subset of layers of a neural network, such as the features described in U.S. Pat. No. 11,246,524, which is incorporated by reference in its entirety. FIG. 4A is a schematic diagram of an implementation of a system for predicting rhythm annotations using neural network encoding. In some implementations, the system can make one or more predictions, such as predicting rhythm annotations or estimating burden for cardiac rhythms including Atrial Fibrillation and/or Atrial Flutter. The wearable device, such as a cardiac monitor patch 402, can process an ECG input 404 through a first subset of layers 406 of a neural network, such as an encoder. The wearable device can receive the output of a first subset 406 of layers of neural network, and transmit the output to a computing device 408 (e.g., an external system such as a smart phone or a server) to further process the data through a decoder that includes a second subset of layers 410 of the same neural network in order to derive a characteristic of the user 412, such as an indication or prediction of past cardiac arrhythmia and/or predict a future onset of arrhythmia.

Figure 4B:
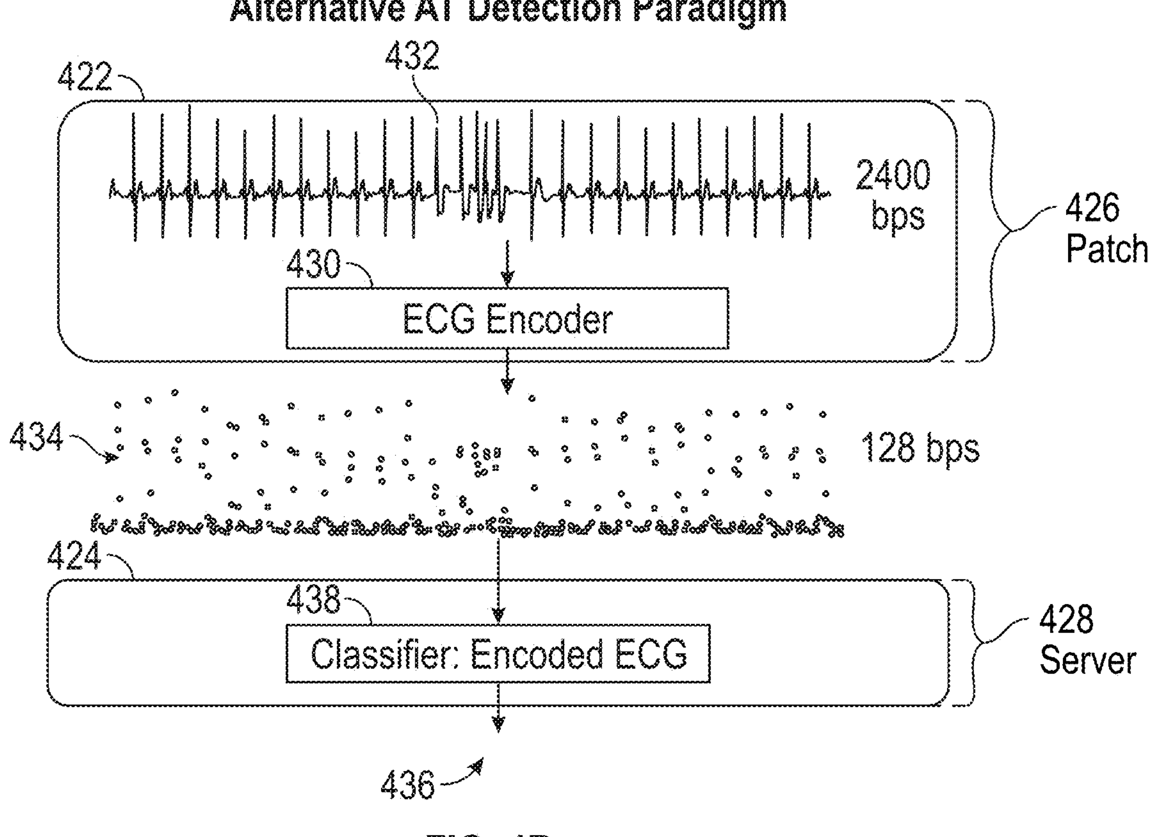
FIG. 4B is a schematic diagram of an implementation of a first and second subset of layers within a single neural network.

In some implementations, the first subset and the second subset of layers are within one neural network. The neural network can be designed such that the output of a first subset of layers can output data at a smaller dimensionality than the input to the neural network, and the output of the second subset of layers can be designed to provide an indication of a user characteristic, such as a past or future prediction of AFib. FIG. 4B is a schematic diagram of an implementation of a first and second subset of layers within a single neural network. The neural network can be trained simultaneously on both the first subset of layers 422 and second subset of layers 424. For example, if a neural network has 10 hidden layers, the first 4 layers is processed on the wearable device, such as a cardiac monitor patch 426, the output of the 4th layer, which is of lower dimensionality than the input (e.g., has good data compression features) to the 1st layer, is transmitted to an external computing system, such as a server 428. The external computing system processes the output of the 4th layer through the 5-10th layers. The dimensionalities of each layer of the neural network can be designed to output a certain data size (e.g., output dimensions for each convolution or pooling layers). For example, the patch 426 can include an ECG encoder 430 that receives ECG data 432 at 2400 bits per second (bps). The patch 426 can process the ECG data 432 through a first subset of layers 422 of the neural network (such as within the ECG encoder 430) and output a smaller dimensionality of data 434, such as data at 128 bps. The output data 434 can be transmitted to an external server 428. The external server 428 can include a classifier 438 that processes the output data 434 through a second subset of layers 424 of the neural network and outputs an indication or prediction 436 of the patient that it is trained for. The entire neural network, including the first subset 422 and the second subset 424 of layers can be designed and trained as a single neural network.

In some implementations, the output of the first subset of layers can be a smaller dimensionality than the input to the neural network. As such, instead of transmitting the entire ECG signal (e.g., the input to the neural network) from the wearable device to the external computing device, the wearable device can transmit a smaller amount of data to the external computing device, such as the 128 bps output data 434 of the first subset of layers instead of the full 2400 bps ECG signal 432. Advantageously, less network throughput is required to derive the indication of past cardiac arrhythmia and/or predict a future onset of arrhythmia.

Moreover, instead of processing the ECG signal on the wearable device through all layers of the neural network in order to derive the indication of past cardiac arrhythmia and/or predict a future onset of arrhythmia, the wearable device can process the ECG signal through only a first subset of the layers (such as through an encoder) of the neural network via the ECG encoder 430, and transmit the output of the first subset to an external device 428 that processes the second subset of layers (such as through a decoder or classifier 438).

Prognosis and Prediction Implementations

Some implementations described herein improve on traditional systems to detect atrial fibrillation using long term continuous monitoring technology. Some traditional monitors include implanted devices that typically have leads implanted into the heart. But such approaches are extremely invasive, do not have suitable communication technology, and are very difficult to update hardware/software.

Moreover, traditional monitors do not provide predictive outcomes based on current cardiac signals or current treatments, let alone provide treatment recommendations, such as intervention, and hospitalization recommendations.

Furthermore, traditional implantable technologies do not capture ECG continuously. These implantable monitors measure ECG data and capture events detected within the ECG data. These implantable monitors capture event data based on a small window of data, such as 10 seconds of ECG data, which can be insufficient to provide predictive outcomes on current cardiac signals, predive outcomes on current treatments provided to the patent, and determine recommendations on treatment recommendations.

Figure 5:
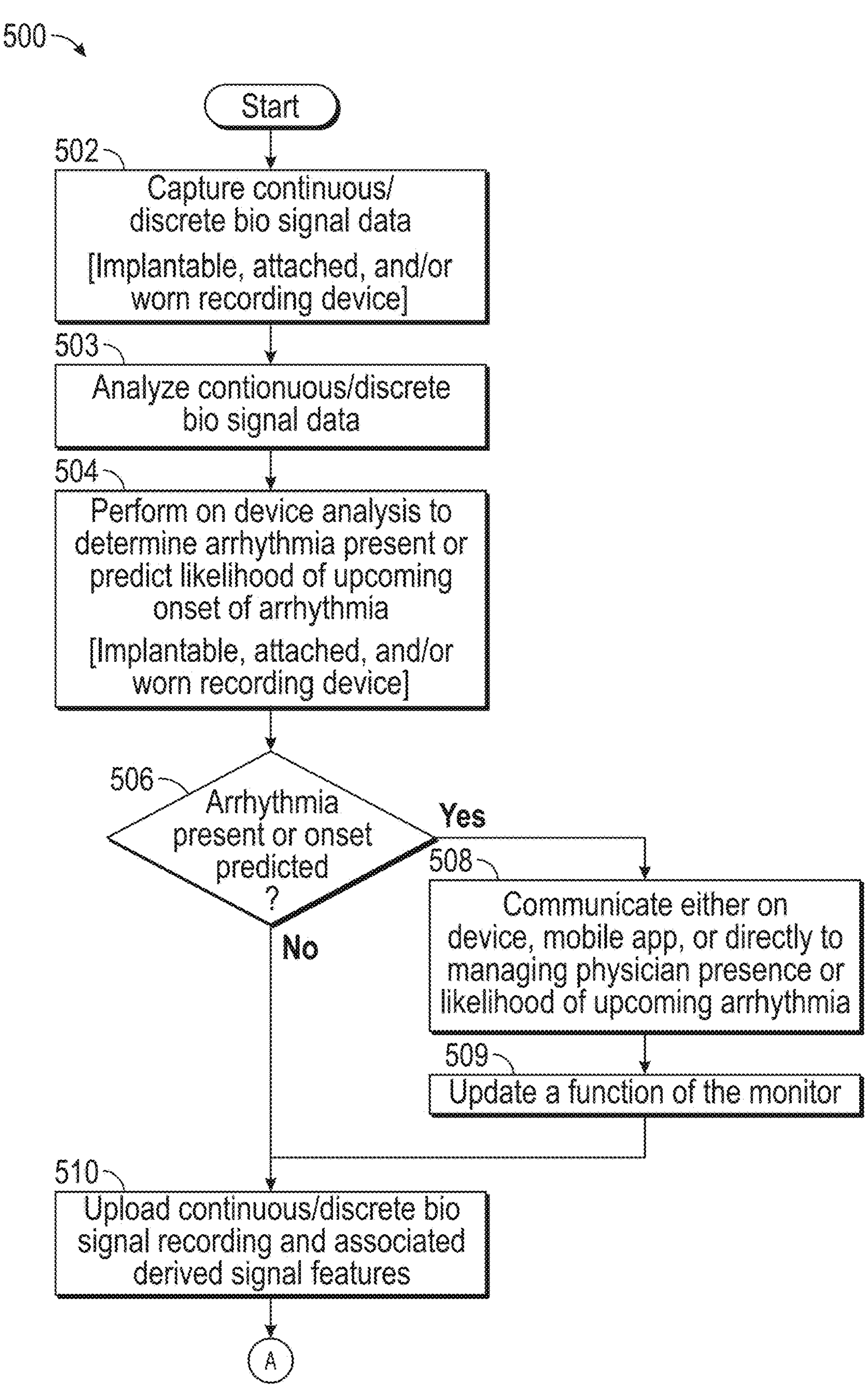
FIG. 5 is a flow diagram of an implementation of the system and an ambulatory monitor.
Figure 5:
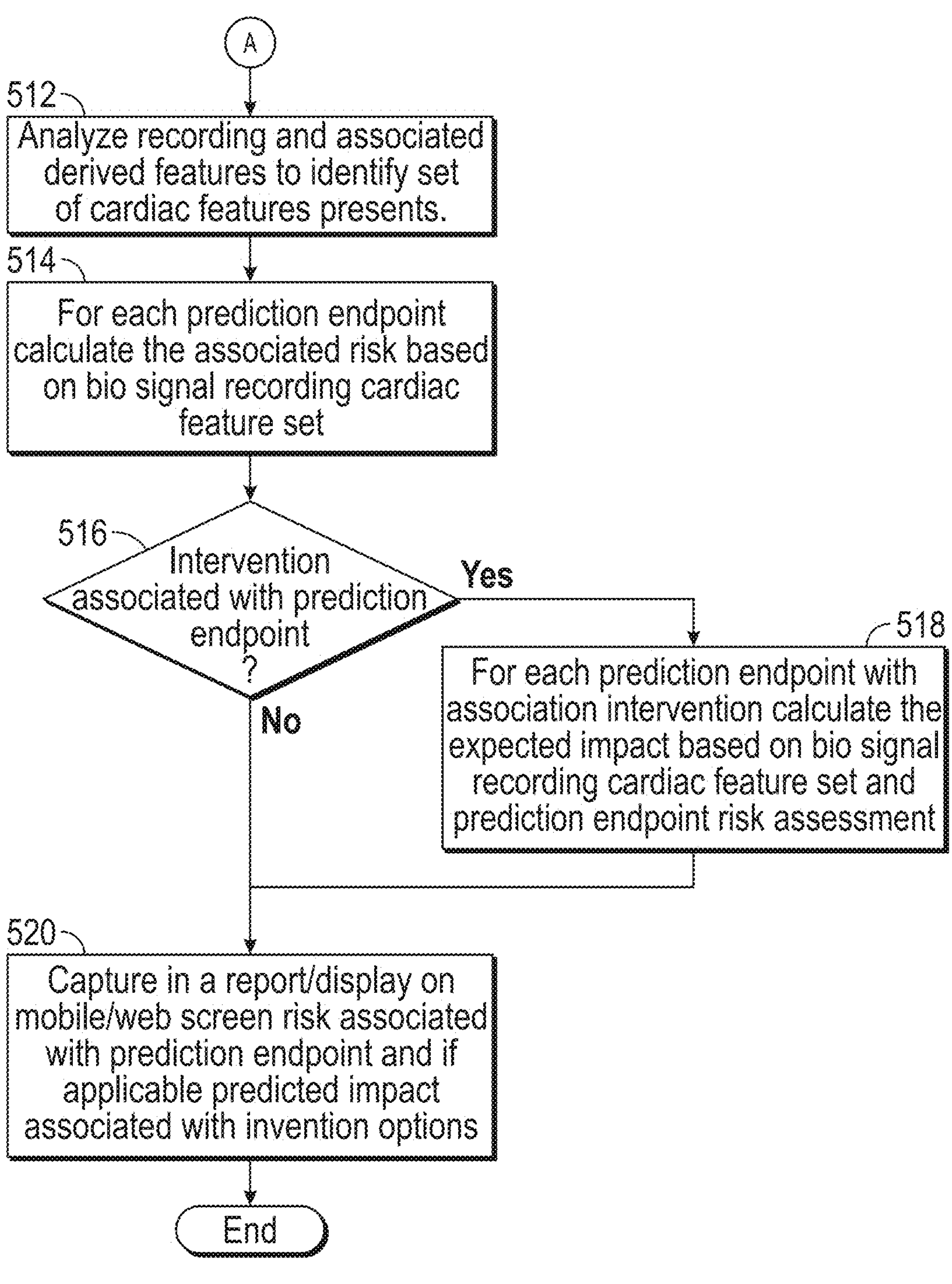

FIG. 5 is a flow diagram 500 of an implementation of the system and a monitor, such as an ambulatory monitor. The monitor can be an implantable, attached, and/or worn recording device. At block 502, the monitor can capture continuous and/or discrete bio-signal data. Some implementations described herein include monitors that can use electrodes and monitoring circuitry to continuously monitor cardiac signals over prolonged periods of time, such as longer than 7, 14, 21, 30, or more days. Some implementations can provide predictive outcomes based on currently measured cardiac signals of a patient over a longer period of time than just a few seconds, minutes, or hours. Some implementations can provide predictive outcomes on currently provided treatments to patients. Some implementations can provide recommendations of treatments to patients based on currently measured cardiac signals and/or current treatments.

In some implementations, the monitor can measure one or more physiological signals, such as, but not limited to: atrial fibrillation, ECG, PPG, Accelerometer data, Heart rate, pulse transit time, impedance measurements, acoustic measurements, RR intervals, blood pressure measurements, temperature measurements, and/or glucose levels.

In some implementations, the system can continuously measure, record, and/or analyze biosignals through a device implanted, attached, or worn by a person in an ambulatory setting. The signals can include raw measurements or features extracted based on signal processing, Machine Learning (ML), or Deep Learning (DL) methods.

At block 503, the monitor can analyze the received continuous or discrete bio-signal data to remove noisy segments or unwanted artifacts. The monitor can apply signal processing machine learned algorithms to classify between noisy segments and segments that are less than a noise threshold level, such as by using a pretrained model. The monitor can apply signal processing machine learned algorithms to determine whether the received signal is noise, an artifact (such as if the user is sleeping, performing a high intensity activity, has a pacemaker, etc.), and/or the like. The techniques can be used to remove or mitigate the noise to improve signal-to-noise ratio. The noise can be created by internal or external sources, such as environmental noise, noise caused by imperfect contact with the electrode, and/or the like.

In some implementations, the signal processing techniques to remove noise and/or unwanted artifacts can include a machine learned model, such as a neural network. The machine learned model can be a different machine learned model than the neural network to make inferences on physiological data (discussed more herein).

In some implementations, the noise machine learned algorithm can be trained to determine whether or not an artifact is present in the data. The noise machine learned algorithm can mitigate noise within the recorded data. In some implementations, the same machine learned algorithm can perform both or either of the identification of artifacts and the mitigation of noise. In other implementations, separate machine learned algorithms are used. In some implementations, the prediction of noise and/or artifacts can be performed on a sample-by-sample level or on groups of samples.

In some implementations, one or more of the following architectures can be used to perform artifact segment identification, noisy segment identification, and/or noise mitigation:

a) fully connected Neural Networks (NNs): for example, fully connected NNs can learn complex relationships between the signal morphology and the actual label of the signal being an artifact or noise or not. Training on diverse set of signals, representing artifact/noise or useful signals, coupled with dropout increases the ability of the network to learn the important relationships between signal and labels (e.g. useful signal, noise, artifact, etc) while reducing the chance of overfitting. For example, the system can nullify certain nodes of a layer or the neural network randomly during training to avoid overfitting and/or to train the neural network more restrictively learning weights that are more robust and predictive for the training purposes.

b) convolutional layers followed by encoder/decoder architectures and/or a fully connected NN: The use of the convolutional layers can allow the use of longer signal sequences as input providing better context (e.g., transitions from useful ECG signal to noisy) for identifying onset and/or offset of noise/artifact regions. The encoder/decoder portion can advantageously identify latent variables that can effectively learn the transitions into and/or out of the noise/artifact regions as well as other signal/noise characteristics using a much smaller set of features. These latent variables can be applied to fully connected layers to produce the complex prediction functions. Due to the smaller size of the network, the implementation of the noise prediction can be accomplished on the device itself, or alternatively the transmission of the encoder output can be efficiently and continuously transferred through a wireless connection in real time allowing the prediction to be performed on a server c) convolutional layers followed by a set of LSTM layers (e.g., in some implementations bidirectional LSTM layers), then and potentially followed by a number of fully connected layers: the addition of the LSTM layers can allow the recognition of parts of the signal that are highly correlated to other parts of the signal thus strengthening the predictive ability of the network. As an example, in a transition section between non-noisy and noisy signal, the LSTM can identify more correlation of the waveforms before and after the transition point and can adjust the sequence of output weights for the system to better identify transition points between noisy and non-noisy segments.

d) A Transformer architecture that can utilize the similarities/dependencies of the characteristics of the continuous signal to provide accurate classification taking into consideration the context within which noise/artifact might exist: The transformer network can advantageously provide a more flexible structure in encoding signal similarities/differences between sections of the signal. As an example, the transformer architecture can adjust its processing based on user selection of the distance in time that similarities are looked at, sequence of frequencies of the signal that should be considered, etc. For example, the transformer architecture can adjust the length of consecutive segments at specific lengths, such as looking at segments that are 1 minute apart, 1 second apart, 1 hour apart, 6 hours apart, and/or the like.

e) Self-supervised learning to extract latent features from a large number of unlabeled signals that include noise and non-noisy regions with diverse type of rhythms and train a model to classify the signals for noisy regions: pretrained features can be combined as input to smaller fully connected layers in order to produce a final prediction of noise or artifacts. Because of the richness of these features but the need of a smaller final classification network, implementation can be performed efficiently both on the device itself and/or a server. For example, a first pretrained model can extract latent features, and additional layers of a second pretrained model can be applied after the first pretrained features to receive the latent features as input and make classifications of noise or artifacts and/or additional layers that take the pretrained features from the self-supervised model and apply the features to make predictions.

f) Siamese networks: This approach can allow the system to train a network to identify specific waveforms as noise/artifact segments that are targeted and user selected. The system can then make a classification much more tailored to the application at hand. Furthermore, if new versions of the signal are considered as segments containing an artifact and/or noise, these segments can be added to the process through adding a newly trained network against the new waveforms of interest. For example, if a model is already trained to identify noise, the model can be trained to also identify artifacts without disturbing the portion of the model that has already been trained to identify noise.

At block 504, the monitor can perform analysis on the captured bio-signals to determine whether an arrhythmia is present and/or predict a likelihood of an upcoming onset of arrhythmia. Some implementations described herein include monitors that can determine that a patient does not have a current AF condition. The monitors can predict an onset of a potential AF condition in the future. Traditional monitoring devices are limited to providing current AF condition information.

At block 506, the monitor determines whether an arrhythmia is present in the cardiac signals and/or whether an onset of arrhythmia is detected. If yes, the flow diagram proceeds to block 508 where communication is sent to a physician or the user on a device, such as a mobile device, of the presence or onset of arrhythmia, and/or the monitor can change a function, such as analyzing a longer time period of data, or gathering more data over a longer period of time, and then the flow chart can proceed to block 509. In some implementations, the monitor can update a function based on the determined arrhythmia at block 509.

Advantageously, an alert can be sent to a physician that is remote from the patient, and the alert can be sent in real-time or substantial real-time of the arrhythmia or onset being detected. The physician's computing device and/or an application on the computing device can be activated by the system to display the alert. As such, even if the physician's computing device does not have the application open for the alert, the system described herein can send an alert that activates the application to then alert the physician. In some implementations, if arrhythmia or the onset thereof is not detected, the flow diagram proceeds to block 510.

Some implementations described herein include ambulatory monitors that monitor cardiac signals and can determine an association with a potential future stroke, death, AF, heart failure, hospitalization necessity, and/or the like. Such ambulatory monitors can make these predictions (such as predicting the onset of AF, or a potential stroke or hospitalization) based on cardiac signals under normal conditions of a patient, such as while a patient lives their daily lives in unhospitalized conditions. For example, for a prediction of a stroke, the ambulatory monitor can apply cardiac monitored data over a plurality of weeks, such as 2 weeks, to make such a prediction. A prediction of an onset of AF can require the same and/or less data than the prediction of a stroke. The amount of data to predict an onset of AF may depend on the age of the person, because an AF prevalence can increase much faster for patients over the page of 70.

Some implementations described herein include ambulatory monitors that can include the encoder on the patch. For example, for ambulatory monitors that process less data (such as less than a week) can include an encoder on the patch and the encoder can process the data to output a smaller dimensionality of data to then send to an external computing system, such as a server. The server can process the output of the encoder to determine physiological characteristics, such as whether AF can be detected in the cardiac monitoring data or predict an onset of AF. Advantageously, the signal can be processed partially on the patch, and partially by the server, such as a cloud server, within the wearable time of the patch. The cloud server can make predictions of the onset of AF and/or treatment recommendations, such as the onset of AF, while the user has the patch disposed on his or her body.

In some implementations, the cloud server can send an alert to a computing device, such as a mobile phone of a user and/or a computing device of a physician to notify him or her of the onset condition. The encoder can transmit less data because of the smaller dimensionality to the server side, and thus provide technical advantages such as automatic-encryption, longer battery life and less processing power required of the patch while the server side processes the data further, less network data throughput used, and the like as further described herein. Moreover if the patient is already hospitalized, such immediate processing and reduction of vital hospital resource usage can be vitally important, such as an onset of a stroke condition where response times correspond greatly with survival rates. The ambulatory monitors can provide a prediction of a physiological characteristic, such as a stroke, and/or provide treatment recommendations, such as sending the patient to an Immediate Care Unit (ICU). The encoder can be trained to output derived signal features from the monitored cardiac signals. For example, the encoder can output features of the cardiac signals, such as boundaries, edges, and/or the like.

At block 510, the monitor can upload the continuous and/or discrete bio signal recorded and/or associated derived signal features outputted from the encoder. The output of the encoder and/or portions of the measured biosignal can be continuously uploaded to the external computer, such as a cloud. The output of the encoder can be uploaded by connecting the patch to a device for the device to send to the external computer, such as via a USB connector to a mobile phone, which then the mobile phone sends the data to the server. Advantageously, if only the output of the encoder without the measured biosignal or only a portion of the measured biosignal is transmitted to the cloud, the monitor can store less data, transmit less data and require less network connection, and save battery life by requiring less transmission of the data and/or require less frequency of the transmission of the data.

At block 512, the external computing device, such as the server, can analyze the recording and/or the associated derived features to identify a set of cardiac characteristics. For example, features extracted from the machine learning and/or deep learning techniques can include one or more of: Afib burden, total time in AFib, longest bringed AFib episode, quantiles of Heart Rate, counts of rhythms, such as Supraventricular Tachycardia (SVT), Ventricular Tachycardia (VT), AFib, Premature Ventricular Contraction (PVC), Premature Atrial Contractions (PAC), Atrioventricular Block (AVB), etc), times of events and density (day, night, week), other arrhythmia burden, counts and durations of episodes within activity levels (low, mid, high), transition pattern features/clustering of features, transition time features, categories of rhythms, arrhythmia densities and changes in density, ectopic densities and changes in density, activity burdens, resting burdens, and/or sleep arrhythmias/burdens.

In some implementations, if an onset of AF is detected, the monitor can adjust a setting and/or the external computing system can instruct the monitor to adjust a setting, such as looking at longer monitor windows. In some implementations, when the monitor is measuring longer monitor windows, the monitor can change the data being transmitted to the external computing system. For example, with the longer monitor windows, the monitor can transmit only the encoder output and not the measured ECG signal, or the monitor can transmit the encoder output with a smaller or larger window of the measured ECG signal.

In block 514, the system, such as the external computing device, can, for each prediction endpoint, calculate the associated risk based on the biosignal recording cardiac feature set. Some implementations include a system that can determine a risk score based on the measured cardiac signals that indicate an onset of AF. The system can determine a risk score based on specific interventions and certain outcomes, such as by clustering prior patient data, as disclosed further herein. For example, a clustering algorithm can cluster patients based on current conditions, intervention types, and outcomes of the intervention types. Then the current patient can be identified as similar to one of the clusters.

In some implementations, based on the identified relevant cluster, the system can recommend an intervention for the physiological condition, such as the onset of AF. The clustering algorithm can be based on years of clinical trials where patients are monitored for current and/or onset conditions, patients are treated with various intervention types or not treated at all, and outcomes of these interventions are recorded. Such data is processed through the clustering algorithm to develop clusters of patients based on current/onset conditions, intervention types, and outcomes.

In block 516, the system can determine if a particular intervention is associated with a prediction endpoint, and if yes, the flow diagram can proceed to block 518, where the system can, for each prediction endpoint with an associated intervention, calculate an expected impact based on the bio signal recording cardiac feature set and prediction end point risk assessment. In block 520, the system can capture the risk in a report and display the report on a device of the patient and/or physician with the prediction endpoint and if applicable, predicted impact associated with the intervention options. For example, the intervention can be associated with a long-term change on the course of the disease. The intervention can be associated with a short-term treatment such as if the person is already hospitalized.

Thus, implementations of the system and/or ambulatory monitors advantageously provide significant advantages to cardiac monitoring technology. The system and/or ambulatory monitors provide prognosis, risk prediction/stratification and treatment guidance, for a host of outcomes and associated cost that are the result of, or associated with the presence of symptomatic and asymptomatic cardiac arrhythmia, for example, Atrial Fibrillation (AF). What results is a risk stratification system delivering superior performance to traditional risk factors. Whereas traditional system diagnosis is limited to providing information into potential treatment or the need for continuous monitoring on the population level, the system and/or ambulatory monitors described herein provides personalized guidance for continuous monitoring (timing and intensity) as well as treatment initiation and titration (such as depending on the current level of arrhythmia severity, and the predicted future severity of outcomes, if left untreated). In particular, the system and/or ambulatory monitors can predict the risk of adverse outcomes, need for intervention, estimate intensity, treatment cost, hospitalization and/or the like using partial or complete record signatures, created from wearable devices, such as signal sequences of multiple modalities, and/or for different time horizons.

In some implementations, the system and/or ambulatory monitors can use latent multimodal features (encoded markers), encapsulating temporal and physiological characteristics of an individual, that can be used as predictors for multiple, future health related endpoints. The system and/or ambulatory monitors can inform the user or physicians on specific combinations of explainable features that can be used to access the role of asymptomatic and symptomatic arrhythmias on the risk of adverse outcomes. The system and/or ambulatory monitors can evaluate the probability of the presence of undiagnosed (and often asymptomatic) AF, often referred to as Silent AF, or predict the onsite on AF, even in the case that a diagnostic device does not detect AF during wear time. AF detection can be a function of the rate of AF and the probability that the occurrence of an event coincides with the wear time of the device. Identification of markers that are indicators of active but undiagnosed AF, based on a single lead ECG or PPG sensor, worn during daily activities and not in a clinic setting, can lead to retesting strategies for those patients that have high confidence scores based on a prediction model, leading to an earlier diagnosis of the disease. The system and/or ambulatory monitors can provide time frames for follow-up testing for silent AF and inform on the recommended timing of this testing.

While this prediction approach is described for AF, the same method could just as well operate for other arrhythmias, for example, tachycardia (including Supraventricular Tachycardia and Ventricular Tachycardia) and bradycardia events (including Pause and AV Blocks). Predictions for ectopic beats (e.g., pre-mature atrial or ventricular beats) could also be developed. Indeed, an advantage to prediction accuracy could be achieved through predicting combinations or categories of future arrhythmias, rather than just one arrhythmia type specifically.

In some implementations, the use of a single-lead continuous monitoring device can provide the advantage of being able to detect and/or predict the presence of silent AF from signals associated with normal activities in a patient, something that an in-clinic 12-lead ECG has lower probability to provide since the measurement is taken for short amount of time (typically 10 secs) under controlled conditions. Traditional systems do not predict the development of AF in the future. The systems described herein can be useful in multi-device solutions, for example, informing if the patient should wear another ambulatory monitoring patch, or engage with extended monitoring paradigms (up to 2 years) provided by a watch/ring or implanted monitor.

In some implementations, the system and/or ambulatory monitors can assess the cluster patient records within specific disease and/or risk groups, and evaluate the clinical trajectory/journey based on the multitude of signatures obtained over time and evaluating the response probability to a specific or family of interventions. This advantage is distinct from the prediction of response to intervention as the groups will inform of the combination of disease trajectory and prior use of specific families of intervention that improve outcomes. This personalizes medicine further as it links disease characteristics with response to specific interventions. The system and/or ambulatory monitors can predict the potential trajectory of a patient's disease progression and the effect of intervention. The system and/or ambulatory monitors can use of risk scores for selection of an individual for inclusion in a clinical study for a given intervention or treatment. The system and/or ambulatory monitors can determine the likelihood of detection of a future event during the monitoring period, for which a clinician could utilize to access the need to continue/extend/terminate monitoring.

In some implementations, after the external computing device determines AF, onset AF, and/or an intervention, the external computing system can transmit data back to the monitor. Advantageously, the transmitted data can initiate a change in the monitor, such as how much data is being measured, the algorithms that are being applied on the monitor, the amount of data (such as a window length) of data being processed on the monitor and/or being transmitted to the external computing device, and/or the like. In some implementations, the external computing device notifies a physician, such as a cardiologist or a managing clinician, to indicate that an AF condition was detected, that an onset AF may be possible, and/or recommendations on intervention (such as providing ablation or medication based on the clustering algorithm described herein).

In some implementations, the system can connect to two wearable devices. The patient can wear one device and upload data to be analyzed by the cloud environment. The system can connect to a second device. In some implementations, the system connects to the second device at the same time as the first device. The system can retrieve similar data to correlate the two, and/or receive different data such as different types of data to further enhance the processing on the system side. In some implementations, the output of the autoencoder architecture recommends the patient to wear a second device, such as what type of device and/or when to wear the second device.

In some implementations, the system can connect to the second device at a later time and associate the record with previous records of the same patient. Thus, the system can create a longitudinal data set of a single modality (such as for ECG) and/or sets of concurrently measured modalities (such as heart rate, PPG, blood pressure, acceleration, acoustic, etc.). The various modalities can be combined to create a much more progressive score effectively. Advantageously, different modalities can provide a much better picture and prediction of onset AF and other physiological characteristics, as well as intervention treatment progression. For example, a differentiation between a signal under stress and a signal when a patient is sleeping may provide a better picture of onset AF. The collection of data by the wearable devices can include continuous signals from a long-term continuous monitor devices, such as cardiac monitor patches, smart watches, smart fabrics, smart eyewear, and/or the like. The wearable devices can post an upload to the system, and the system can perform analysis of the recorded signal on a mobile computing or cloud environment. The algorithm, data and results of such analysis can be stored in the cloud for long-term storage.

In some implementations, the data received from different devices can result in separate risk scores that can show progression of the physiological characteristic. For example, if based on a measurement of a smart watch wearable device (e.g., a score of 20 in time 1, and a score of 50 in time 2), the system can indicate a fast progression of AF and recommend wearing a patch.

Risk Prediction Implementations

In some implementations, the risk prediction models can require input of variables/features, and an algorithm that can appropriately weights these inputs to produce a risk score for a given outcome for a specific timeframe. The system can select inputs from any number of features, as described herein. For machine learning, statistical modeling, and deep learning models, discrete features from the aforementioned features can be combined to produce risk estimates using methods described herein. For continuously measured signals, or signals that have a time dimension (e.g., rhythm labels derived from ECG through an annotation algorithm, based on the waveform within a specified time interval), the system can use a number of numerical methods to produce appropriate forms of inputs for calculating a risk score through a trained algorithm. The system can use these methods on individual signal measurements or be combined together to convey concurrent information.

In some implementations, combinations of these signals can be aligned in time and sampled (upsampled, downsampled, or maintained) at the same sampling rate to produce a concurrent set of measurements. The one-dimensional signals of each type might be scaled and combined to form a strip of data. The x-axis of the strip can be running along time while the y-axis will be representing the stacking of the one-dimensional signal modalities. Advantageously, this organization of the data has the benefit of allowing feature creation based on different signal modalities simultaneously. This data structure can be further augmented by using signal transformations or interactions of the individual signals. Such transformations might include Fourier or wavelet transforms of the original waveforms. Interactions might include simple multiplications of two or more signals, or powers of these signals or time-lagged convolutions of the signals.

In some implementations, the system can form the data structure as an image and apply deep learning image analysis methodologies to produce reduced representations of the signals. Specifically, the system can use autoencoder models, utilizing 2D convolutions of the signals, to create a latent representation of the complete signal. Such latent features can be of varying dimensions, encapsulating the relationships of the different signal information in a reduced number of dimensions. In some implementations, these latent variables can be extracted from the bottleneck layer(s) of the autoencoder.

In some implementations, the system can apply an autoencoder architecture that represents a dimensionality reduction methodology that is able to extract a set of features that when combined with appropriate weights and layer architecture can reconstruct the original signal with high fidelity. This dimensionality reduction can enable the autoencoder to create a “record signature”, such as a unique characteristic of the partial or complete recording of a signal or concurrently measured signals that can uniquely represent the record. The representations that correspond to “similar” records can have similar “record signatures” in an appropriate distance metric. In alternate implementations, dimension reduction methodologies, like principal components analysis and random projections can be used instead of an autoencoder. The system can perform feature selection and/or extraction in a supervised or unsupervised way.

Supervised Feature Extraction and Model Development Implementations

Figure 6:
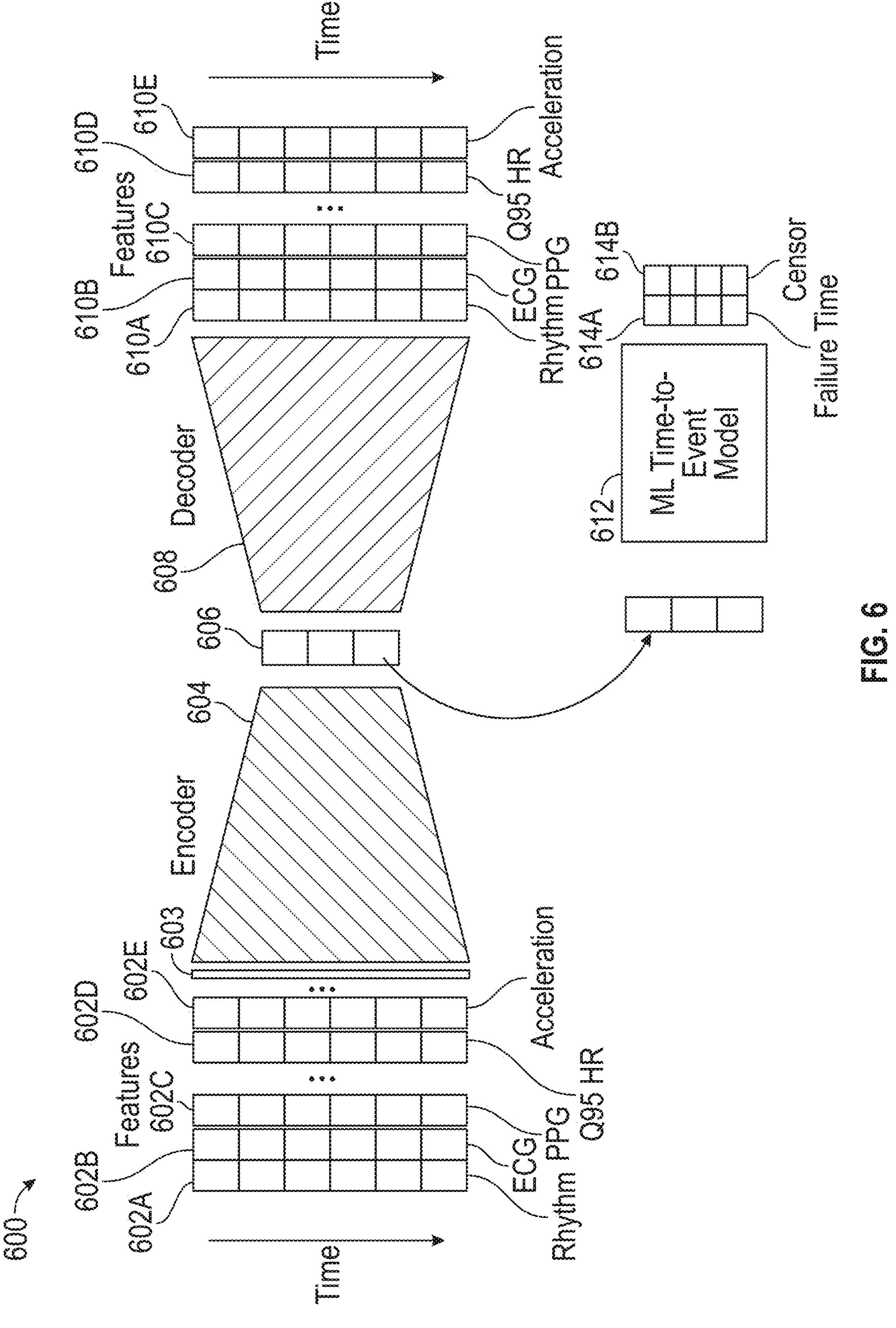
FIG. 6 illustrates a schematic of an implementation for an autoencoder.

FIG. 6 illustrates a schematic of an implementation for an autoencoder architecture 600. The autoencoder architecture can include a noise machine learned model 603 that removes unwanted artifacts and mitigates noise (as further described herein), an encoder 604 and inputs to the encoder, such as rhythm data 602A, ECG data 602B, PPG 602C, Q95 heart rate 602D, and acceleration 602E. The autoencoder architecture can also include the output of the encoder 606, a decoder 608 which receives the output of the encoder 606, and outputted features which represent the same input to the encoder, such as rhythm data 602A, ECG data 602B, PPG 602C, Q95 heart rate 602D, and acceleration 602E.

In some implementations, the encoder 604 can be trained with a decoder 608 such that the decoder 608 outputs an approximation (often with reduced levels of noise) of the same data as the data inputted to the encoder 604. The encoder 604 and the decoder 608 can be trained with a plurality of modalities such that the encoder 604 can be trained to analyze each of the inputted data into the encoder to extract features in the output of the encoder 606. The input of the encoder 604, such as the rhythm data 602A, ECG data 602B, PPG 602C, Q95 heart rate 602D, and acceleration 602E, can be aligned in time. Since the encoder decoder (604,606,608) is trained, the encoder 604 can automatically determine, based the training, that for a particular data set of a patient, that the end of the ECG that aligns with a lower point of the PPG with a $5^{th}$ percentile in heart rate and with high acceleration in that frame corresponds to the onset of AF. Advantageously, the encoder can be trained to assess multiple modalities at once to make predictions of features and/or onsets of AF.

In some implementations, the desired outcome can guide the feature extraction process. The autoencoder architecture can be trained to create a compressed representation of a large number of samples. The encoder 604 can be connected to another Deep learning network architecture that will be trained for classification or risk prediction, using an appropriate loss function. The encoder can be implemented on the device and send the encoded data to the server where the rest of the Deep Learning network will use the encoded features to predict the relevant outcome (classification probability, survival probability, outcome label e.g., AF).

In some implementations, the encoder can be trained along with the decoder in order to produce an approximation of the original data, followed by attaching the pre-trained encoder to other Deep Learning network architectures that are then trained simultaneously in order to predict a number of desired outcomes. Each attached architecture might be predicting a single outcome based on the same output 606 of the encoder, or a multi-task architecture might be used to predict multiple outcomes simultaneously (e.g. risk of stroke and heart failure and hospitalization). During this training the weights of the encoder may kept frozen or be allowed to continue to adjust, so that the complete network is trained to make predictions for the desired outcomes. An advantage of using a pre-trained encoder with frozen weights is that in can be output features in layer 606; this single outcome can be transmitted and used from multiple Deep Learning networks, that were trained along with the encoder, for the prediction of one outcome per network. Such a solution reduces the amount of data to be transmitted, since one output can be used from multiple Deep learning networks for the prediction of multiple desired outcomes or a single multi-task Deep Learning network. Furthermore, the dimensionality of the encoder bottleneck layer, or the output of the encoder 606, can be adjusted to satisfy conflicting operating requirements and performance. For example, the dimensionality can be reduced to reduce data transmission, require less processing of input data by the server, require less storage, and/or the like. The dimensionality of the encoder can be selected based on the desired algorithm on the server side, such as having multiple algorithms for different scenarios and/or desired outcomes.

In some implementations, the dimensionality of the encoder can be determined based on the desired accuracy of the output. For example, a smaller dimensionality can lead to a lesser accuracy, but with less network bandwidth usage. In some implementations, the dimensionality can be frozen to predict a certain set of outcomes. But if a different set of outcomes are desired, the system may adjust the dimensionality that may be better to predict a different set of outcomes, such as predicting hospitalization versus predicting stroke.

In some implementations, the training labels include one or more of: a disease/no disease classification, for different outcomes (stroke, MI, etc), a set of set of time to event values along with failure or censoring indices, a set of financial outcomes related to health care expenses, a set of hospital stay durations, a set of times to the next device prescription, and/or a set of times to the onset of an arrhythmia (e.g. AFib) with failure or censoring indices.

In some implementations, the encoder 604 and the decoder 608 are trained together. After training, the encoder 604 is applied to patient data, and the output of the encoder 606 is processed through a Machine Learning (ML) time-to-event model 612 that predicts probabilities of survival/failure (occurrence or not of an event) within a specified timeframe. The ML model has been trained to predict the probabilities using the output 606 and as outcome the combination of the failure time 614A (time to the event occurring) and censor 614B (whether the failure was observed at that time).

Two options for the development of a risk-based model are highlighted in FIG. 5. An autoencoder network can receive, at the encoder 604, a 2D tensor of time-aligned measurements or transformations (e.g., Heart Rate extracted from ECG or PPG signals) and through the process or reconstructing the signal it reduces its dimensional representation (bottleneck layer) as the output of the encoder 606. The 2D tensor has time as its first dimension and any combination of the aforementioned quantities as its second dimension. By using multiple of these inputs from the same, as well as multiple, device, the autoencoder architecture can record a lower-dimensional representation of a partial or complete device signal tensors and can be reconstructed. In the first version, the bottleneck layer can be extracted and introduced into a machine learning model 612 as its input (in case that the bottleneck layer id 2D or higher, it can be flattened to a vector). Standard parametric and non-parametric time-to-event statistical models (e.g., Cox proportional Hazard models, parametric (Weibull, lognormal, etc,), or survival tree models) can be used to appropriately weight and integrate the most informative of the bottleneck layer parameters to fit survival models.

In some implementations, transformer architectures can be used to incorporate features (either explainable or latent) with demographic (such as age, ethnicity, location), clinical (current measurements) and past historical health data to predict sequences of outcomes, interventions, and associated costs that can be used to predict a trajectory for a patient. These architectures can also incorporate longitudinal records and identify those records or segment of records that best predict the desired outcome. This architecture can be used in the prediction of a sequence of events of interest (occurrence of future AF episode, stroke, hospitalization, treatment, etc.), using longitudinal monitoring. The context might include events within a record, between longitudinally obtained records and/or future events (stroke, death, etc.) related to the measurements at hand. As an example, cardiac monitor patch may contain features that point to AF that is not yet detected by the patient.

In some implementations, a follow-on application of a monitoring patch, based on the information from the first one, may diagnose AF and the corresponding burden. A series of patches might be used to estimate the probability of an adverse event like stroke. A Transformer based model, trained with adequate data can thus be used, automatically selecting the most relevant of records to predict the next event of interest (e.g., patient doesn't know of an AF condition→asymptomatic AF→symptomatic AF→stroke), or incorporate treatment decisions that will reduce the probability of such events. Furthermore, the system may include predictions on the sequence of hospitalizations and corresponding cost associated with treatment and stays.

Advantageously, the encoder architecture can apply the encoder to generate features, and the features that are outputted by the encoder can be processed through another algorithm, such as a neural network, to determine the desired outcomes, such as the onset AF conditions. Traditional algorithms have limited ability to incorporate temporal relationship of the data within long time frames. However, architectures as described here (LSTMs, Transformers, etc.) are able to incorporate these relationships naturally in order to make such predictions.

In some implementations, the machine learned model for cleaning the noise (referred herein as the noise machine learned model) can be trained with the machine learned model for making inferences (referred herein as inference machine learned model). The training data can be inputted into the noise machine learned model and the output of the noise machine learned model (or a derived signal thereof) can be inputted into the inference machine learned model. It is appreciated that additional computations or signal processing techniques can be performed before and/or after either of the machine learned models.

In other implementations, the machine learned model can be the same model as the neural network that makes inferences. The single machine learned model can be trained to both clean the data of unwanted artifacts and/or noise, and to make inferences on the data.

In other implementations, the training of the machine learned models can be performed remote of the monitor. However, one or more of the machine learned models can be applied on the monitor side. In some implementations, one or more of the machine learned models can be applied on the sever side (such as all of the machine learned models). For example, for short term predictions on the data, the monitor can perform one or more of the machine learned models. Advantageously, an alert can appear to the user right away from either the monitor or another computing device, such as a mobile phone. Moreover, if a concerning inference is made, the device can trigger another process, such as applying a model for long term predictions or a different algorithm making different inferences (such as one that looks at different characteristics of the user). Such long term prediction models can be performed on the server side.

In some implementations, cleaning of the data can be made at certain time periods, such as every second, minute, hour, and/or the like. For example, an artifact can be found and/or noise mitigated based on a 30 minute window every 30 minutes. In other implementations, a sliding window of a certain time period can be used and data cleaning can be performed based on the amount the sliding window slides. For example, a 30 minute window of data can be used to make predictions every 5 minutes.

In some implementations, for long term predictions that require a longer period of data, one or more of the machine learned models can be performed on the server side (such as all of the machine learned models). For example, the monitor can record data for a prolonged period of time, such as days, weeks, months, and/or the like. The data on the monitor can be downloaded onto the server side, and the remote server can perform long term predictions on the data.

In some implementations, a subset of the machine learned models and/or portions of the machine learned models can be performed on the monitor side, while the rest of the architecture is run on the server side. For example, the noise machine learned model can be performed on the monitor while the inference machine learned model can be performed on the remote server. In some implementations, a portion of the inference machine learned model (e.g., a first subset of layers) can be performed on the monitor, while the remaining portion of the model (e.g., a second subset of layers) can be performed on the server side.

Advantageously, not all of the data would be required to be transmitted from the monitor to the server, reducing the amount of data transmitted. This would then require less network bandwidth. Moreover, the monitor could require a smaller memory as the whole dataset would not have to be saved before transmitted. The data can be processed through one or more machine learned models to output certain data, such as vectors. And these vectors would be saved and transmitted to the remote server.

Figure 7A:
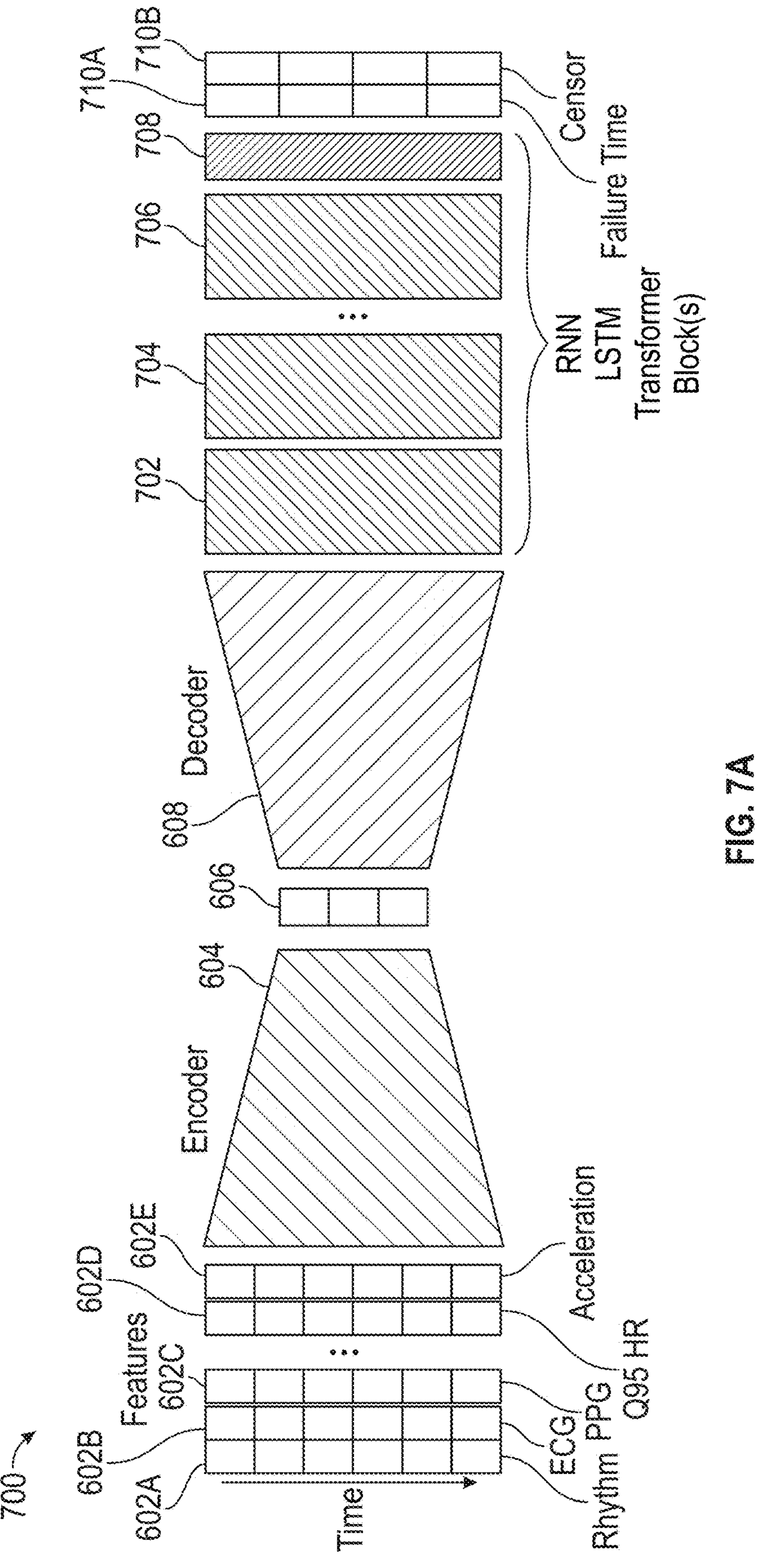
FIG. 7A illustrates a schematic of an implementation for applying an LSTM transformer block at the output of the decoder.

FIG. 7A illustrates an network architecture 700 of an implementation for applying an one or more LSTM transformer blocks at the output of the decoder. The network architecture 700 can include input features to an encoder 604, the encoder 604, an output of the encoder 606, a decoder 608, RNN and/or LSTM blocks 702, 704, 706, 708 This architecture will be trained with the use of data that include a failure time 710A, and a censor output 710B and will be producing probabilities of outcomes of interest within prespecified timeframes. The autoencoder can be separately pre-trained or be part of the complete model training. It is included as a feature extraction/compression and noise reduction tool targeted especially for long (in the time direction) records of combined inputs when methods that are applicable to image recognition are desired, otherwise it can be removed, and the input be connected to the remaining layers.

Figure 7B:
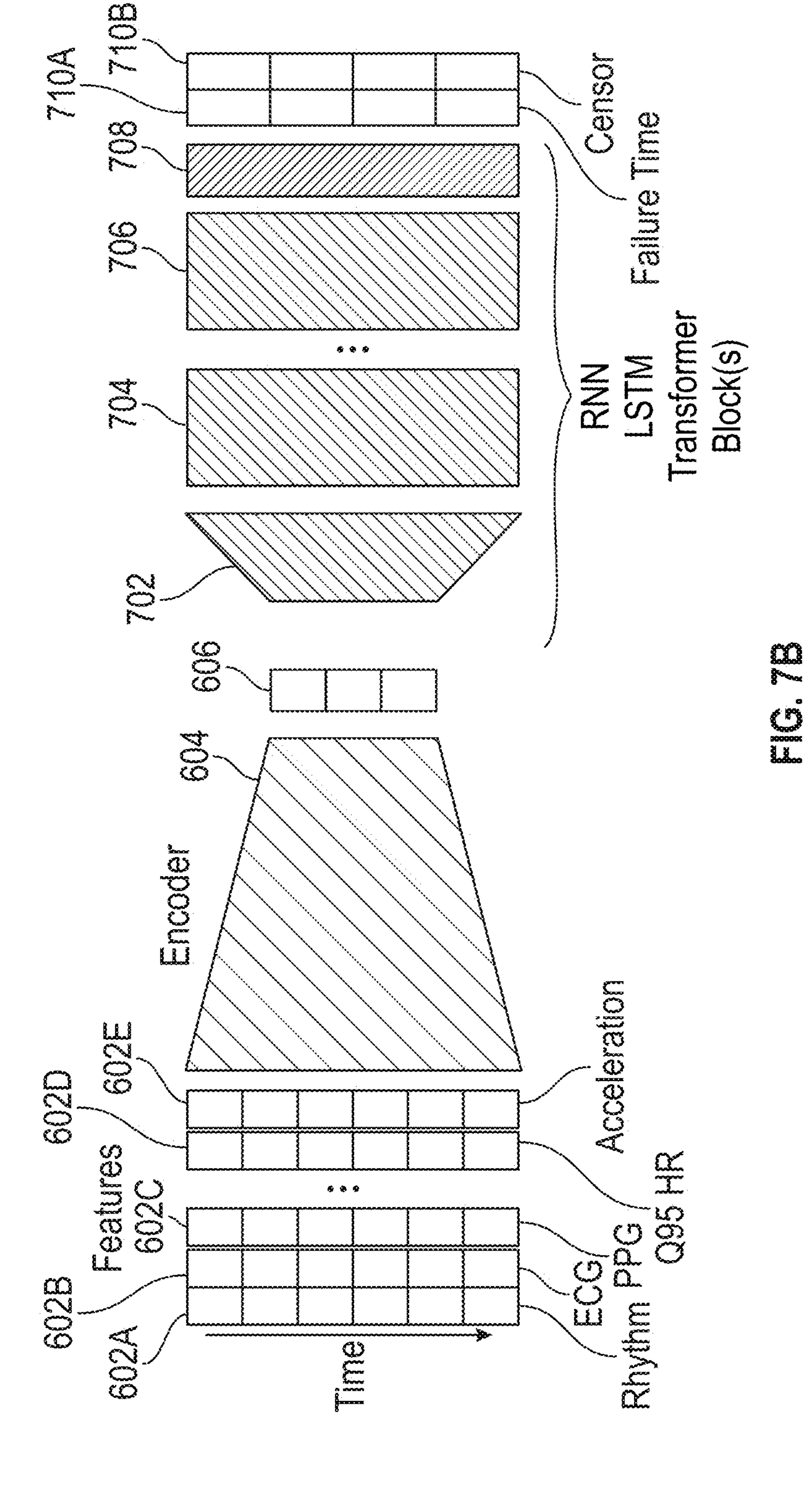
FIG. 7B illustrates an autoencoder architecture of an implementation for applying an LSTM transformer block at the output of the encoder.

FIG. 7B illustrates a Deep Learning architecture 750 of an implementation for applying a series of LSTM and/or Transformer blocks at the output of the encoder. In some implementations, the autoencoder can be composed of combinations of LSTM layers, capturing unidirectional or bidirectional relationships, RNN and/or Transformer blocks. Advantageously, these architectures can incorporate signal features, their interaction with other signal features in temporal, and physical distance that inform on the health state of the person and risk of development of health problems at different timeframes. Thus, the encoder architecture can naturally encode information of correlated features and/or timings between features (groups of patterns and timing characteristics) that can then be processed by other layers incorporating temporal relationships that can be more powerful in the prediction of time to event predictions.

In FIG. 7B, the input 602A, 602B, 602C, 602D, 602E, encoder 604, and output of the encoder 606 (e.g., bottleneck) can be attached to a number of other layers (possibly with repeated such blocks incorporated into the architecture of the model) followed by one or more models of dense layers, that might also incorporate demographic or clinical variables as inputs and connected to an output layer that represents the right censored data for either AF, stroke or other clinical outcomes of interest.

In some implementations, the autoencoder architecture 750 can be trained from front to end. The autoencoder architecture 750 can be trained using past cardiac data (such as PPG, ECG, heart rate, and/or the like) of patients and resulting conditions of the same patients. For example, the training data can include patient data from years in the past with current and/or subsequent patient conditions and/or subsequent conditions from the recording of the cardiac data. The training data can be used to train the system by adjusting weights in the encoder and the transformer block. The pretrained weights are adjusted in the encoder. The transformer that follows the encoder can be trained with random weights. During training, the encoder weights are expected to change slower than the rest of the network, including the transformer weights and other layers. Through the training, the encoder weights are adjusted to emphasize specific features that are better for detecting AF, onset of AF, and/or other arrhythmia elements.

Figure 7C:
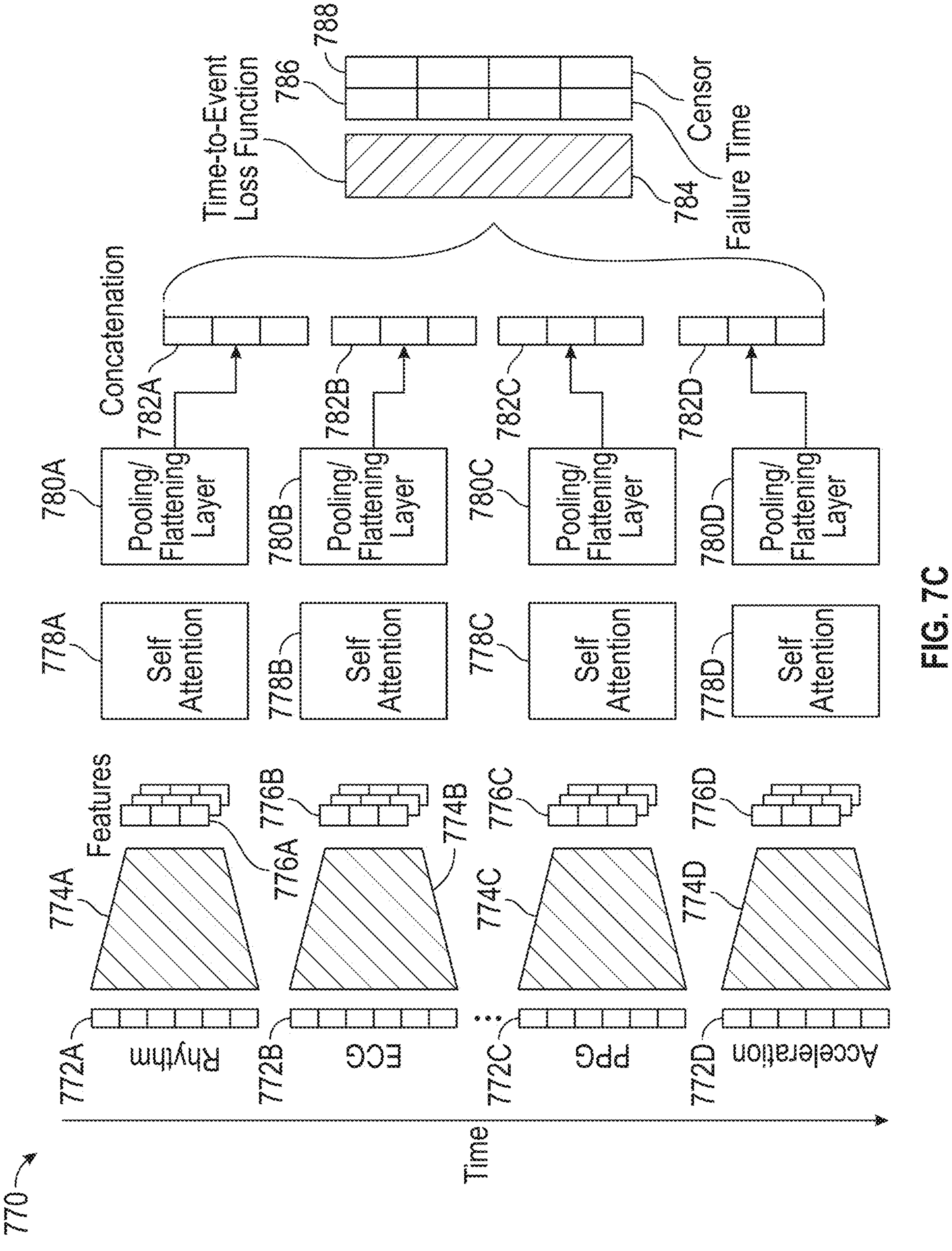
FIG. 7C illustrates a self-attention architecture for inferring an onset of cardiac arrythmia.

FIG. 7C illustrates a self-attention architecture for inferring an onset of cardiac arrythmia. The self-attention architecture 770 can include a plurality of input nodes 772A, 772B, 772C, 772D (collectively referred to as input nodes 772), encoders 774A, 774B, 774C, 774D (collectively referred to as encoders 774), latent features 776A, 776B, 776C, 776D (collectively referred to as latent features 776), self-attention modules 778A, 778B, 778C, 778D (collectively referred to as self-attention modules 778), pooling and/or flattening layers 780A, 780B, 780C, 780D (collectively referred to as pooling and/or flattening layers 780), concatenation module that concatenates the outputs 782, and output nodes, such as time-to-event loss function 784, failure time 786, censor 788, and/or the like.

In some implementations, the self-attention architecture can receive as input a plurality of different types of data, such as heart rhythm data 772A, ECG data 772B, PPG data 772C, acceleration data 772D, and/or the like. The architecture can include a plurality of encoders 774, each of which can take one or more of the input data. For example, each encoder can be trained to output latent features for individual input data types (e.g., first encoder for rhythm data, second encoder for ECG data).

In some implementations, the self-attention modules 778 can receive as input the latent features that were outputted by the encoders. The self-attention modules 778 can find similarities of these latent features based on a distance metric or loss function. The self-attention modules 778 can calculate a weighted output vector based on these similarities and the input latent features. For example, the self-attention module 778A can determine an output by weighing rhythm data on the second, fifth, and tenth minute higher than the rest, while the self-attention module 778B can determine an output by weighing ECG data on the first, fourth, and sixth minute higher than the rest.

In some implementations, the output of the self-attention module 778 can be pooled and/or flattened to a single value or a vector. For example, a maximum or mean value can be taken from the output of the self-attention modules. The self-attention architecture can concatenate the outputs into a single vector. The lengths of the outputs 782 do not have to be the same size because in some instances, the outputs 782 are aligned in time.

In some implementations, the self-attention architecture can be trained using patient outcome information that includes a failure time and a censor variable through a time to event loss function (e.g. negative log partial likelihood of the Cox proportional hazard) 784 that predicts probabilities of survival/failure (occurrence or not of an event) within a specified timeframe, a failure time 786 (time to the event occurring) and censor 788 (whether the failure was observed at that time). In some implementations, the output can include a single probability of survival or death, or a vector of probabilities of survival or death (e.g., a vector of probabilities across different time periods).

Figure 7D:
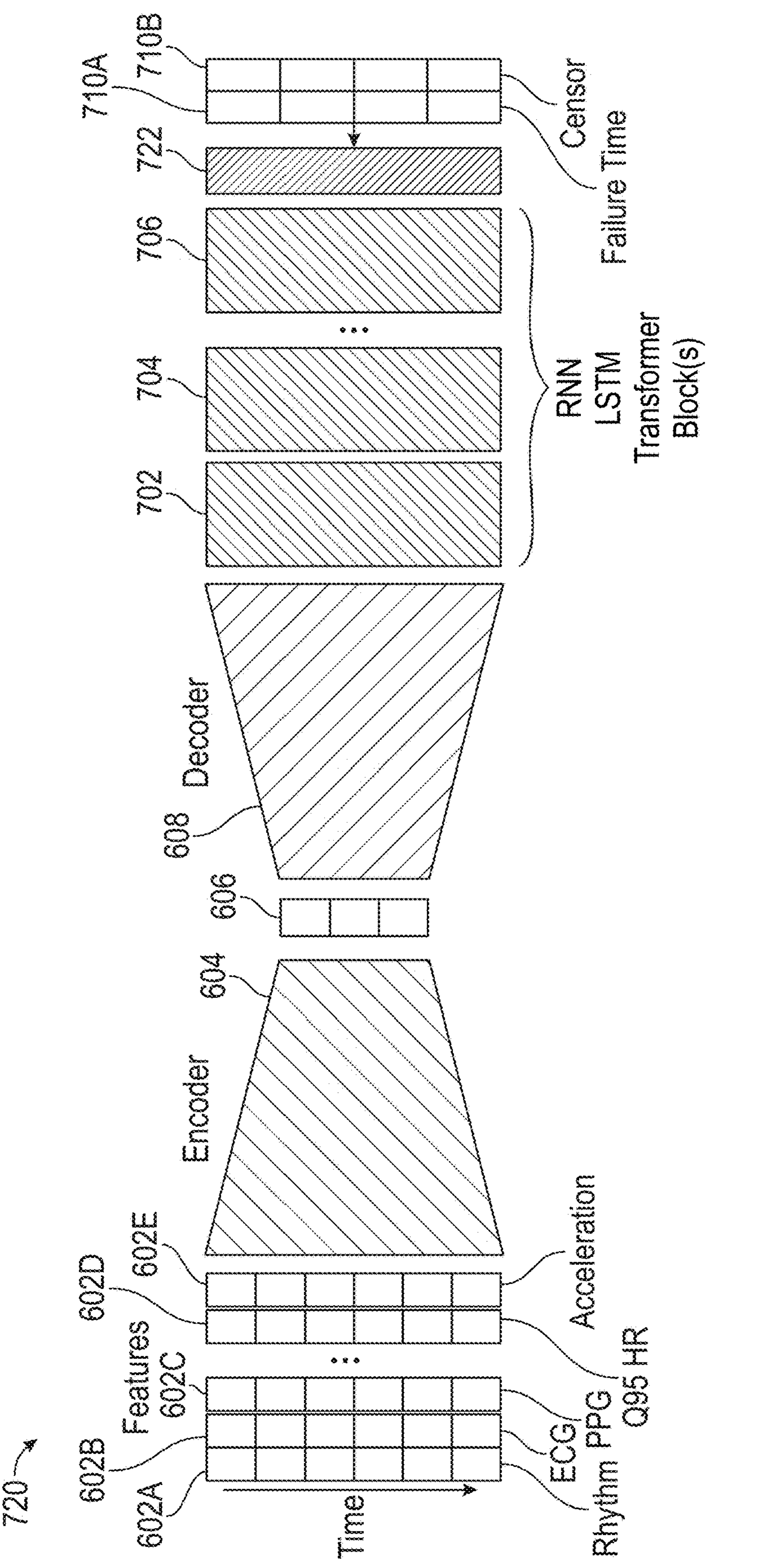
FIG. 7D illustrates a network training architecture for applying an LSTM transformer block at the output of the decoder.

FIG. 7D illustrates a network training architecture for applying an LSTM transformer block at the output of the decoder. In this example, the autoencoder and LSTM transformer blocks of FIG. 7A are shown. However, it is appreciated that other neural networks and/or architectures can be applied. During training, input data (such as historical patient data including rhythm, ECG, PPG, and/or the like) is inputted to the encoder 604. The data is processed through the encoder 604, decoder 608, and the LSTM transformer blocks 702, 704, 706, 708. The output of the last block of the LSTM transformer 708 is inputted into the loss function 722. The true values (e.g., from the failure time 701A, censor 710B) are also inputted into the loss function 722. Based on the output of the loss function 722, the system will adjust the weights of the neural network. For example, if the output of the last block of the LSTM transformer 708 is close to the true values, then the loss function 722 could output a minimal loss, whereby the system can then reinforce the weights of the neural network (such as increasing the weights such that the neural network would be reinforced to produce an output similar to the output that was similar to the true values.

Figure 7E:
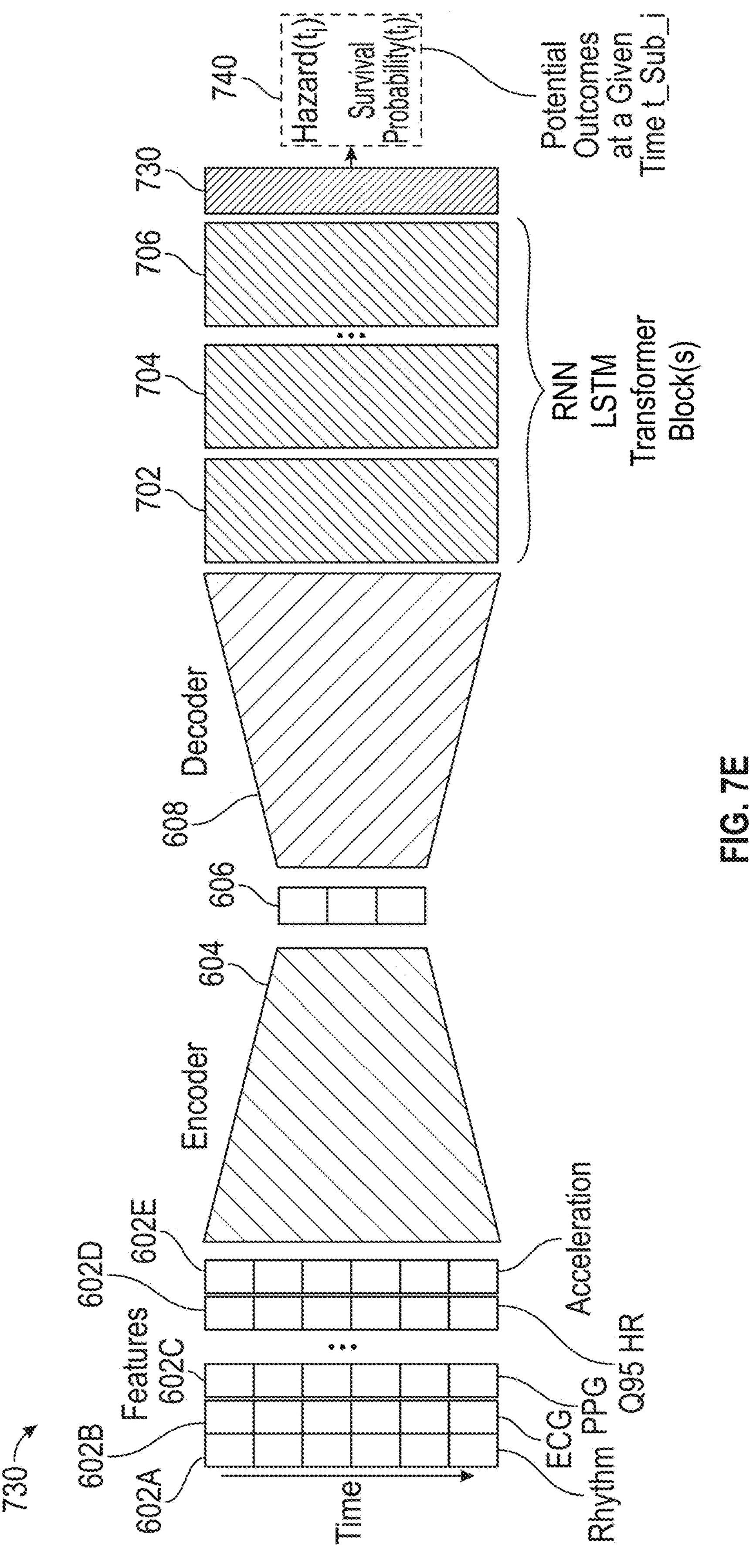
FIG. 7E illustrates a network inference architecture for applying an LSTM transformer block at the output of the decoder to generate a hazard and/or survival probability.

FIG. 7E illustrates a network inference architecture for applying an LSTM transformer block at the output of the decoder to generate a hazard and/or survival probability. In this example, the autoencoder and LSTM transformer blocks of FIG. 7A are shown. However, it is appreciated that other neural networks and/or architectures can be applied. During inference, input data (such as current patient data including rhythm, ECG, PPG, and/or the like) is inputted to the encoder 604. The data is processed through the encoder 604, decoder 608, and the LSTM transformer blocks 702, 704, 706, 708. The output of the last block of the LSTM transformer 708 is outputted via an output node or layer 730.

In some implementations, the potential outputs can include probabilities of the patient or user, such as a hazard probability or a survival probability. The hazard probability can include a probability of a failure (e.g., a patient's death) at time $t_i$. Such a probability can be a conditional probability (e.g., the probability that the patient dies at time $t_i$ on the condition that the patient survived up to time $t_i$). Thus, the hazard probability can be determined by filtering users that have survived up to that point, and then determining the user's probability based on the subset of historical users that have survived up to that point in time. The survival probability can include a probability of a user surviving past time $t_i$.

Figure 7F:
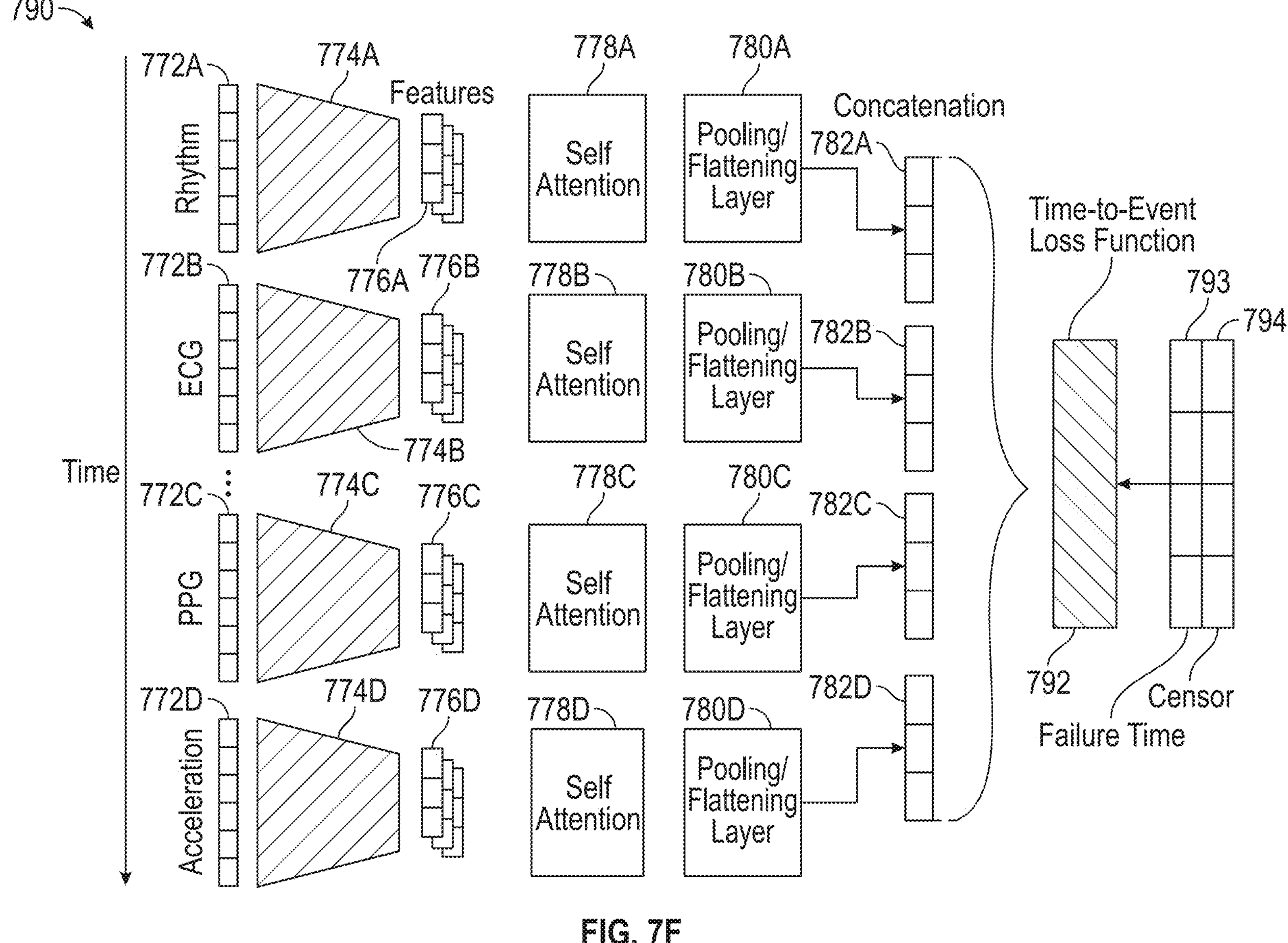
FIG. 7F illustrates a network training architecture for applying a self-attention architecture using a loss function.

FIG. 7F illustrates a network training architecture for applying a self-attention architecture using a loss function. In this example, the self-attention architecture of FIG. 7C is shown. However, it is appreciated that other neural networks and/or architectures can be applied. During training, input data (such as historical patient data including rhythm, ECG, PPG, and/or the like) is inputted to the encoders 774. The data is processed through the encoders 774, self-attention architectures 778, pooling/flattening layers 780, and the concatenation 782. The output of the concatenation 782 is inputted into the time-to-event loss function 784. The true values (e.g., from the failure time 786, censor 788) are also inputted into the loss function 784. Based on the output of the loss function 784, the system will adjust the weights of the neural network.

Figure 7G:
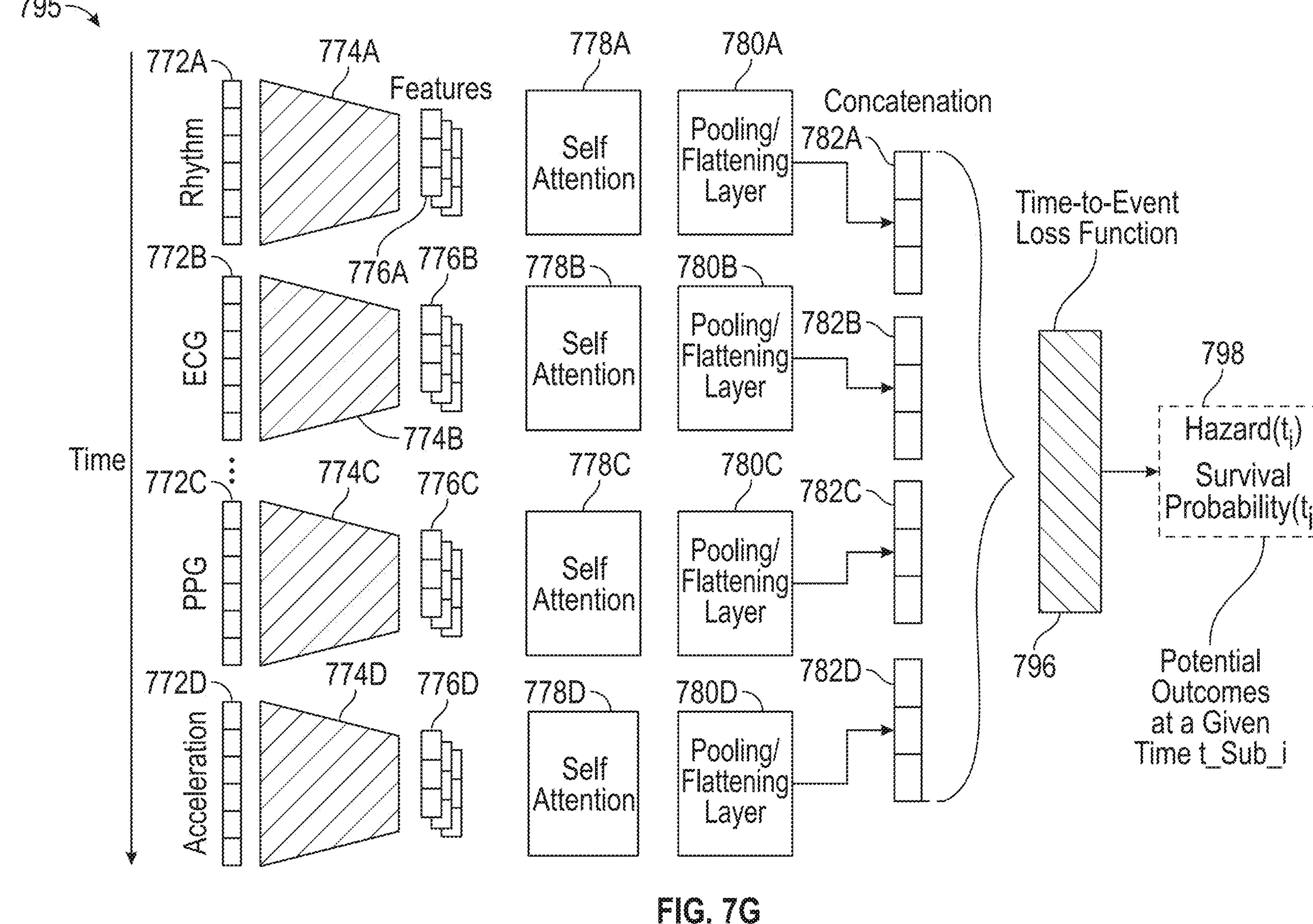
FIG. 7G illustrates a network inference architecture for applying a self-attention architecture to generate a hazard and/or survival probability.

FIG. 7G illustrates a network inference architecture for applying a self-attention architecture to generate a hazard and/or survival probability. In this example, the self-attention architecture of FIG. 7C are shown. However, it is appreciated that other neural networks and/or architectures can be applied. During inference, input data (such as current patient data including rhythm, ECG, PPG, and/or the like) is inputted to the encoders 774. The data is processed through the encoders 774, self-attention architectures 778, pooling/flattening layers 780, and the concatenation 782. The output of the concatenation 782 is outputted via an output node or layer 796. Potential outcomes are determined, such as a hazard probability or a survival probability 798.

Unsupervised Feature Extraction, Model Development and Patient Clustering Implementations In some implementations, the models are referred to a "feature engineering" engine. Specifically, the models can provide a representation of the complexity and interaction structure of the features that mostly distinguish one record from the other. As examples, the autoencoder, principal components, and/or the Random Projections architectures can be able to extract characteristics of complete or partial records that represent the record's overall information content.

In some implementations, every record can be passed through the model to obtain a "feature representation summary" ("or signature") that can then be used with a number of other modeling techniques to identify the feature summaries that best associate with or predict a specific outcome of the set described earlier. A "signature" can include a compressed mathematical representation of the original signal. The signature can be composed of a set of numerical values that represent the original signal(s) in a lower dimensional space. The signature can be represented as vectors or tensors and each numerical value of the representations can be thought as the coordinate of the original signal in a new k-dimensional space. As an example, in FIG. 8 (as described further herein), a set of individual signatures that have been run through the model have been projected on a 2-dimensional space and are represented as points, clustered based on their similarity. A higher dimension representation, including but not limited to the original signal is given for the centroid of each cluster in the form of a line plot and a color strip both representing the magnitude of the original signal projection to a coordinate space with dimensions greater than two that the points represent. The advantage is that these models extract informational content that is not specific to a given outcome or even modeling approach (e.g., classification vs. survival).

In some implementations, every new record can be run through the model and a new "signature" can be created for the record. These signatures can be stored in the database and be clustered based on an appropriate similarity metric. Such clusters can be created based on traditional machine learning clustering approaches or deep learning representations such as a sparse autoencoder. This database can be used, along with demographic and clinical data to develop supervised models for outcomes of interest.

Alternatively, based on the creation of a universe of patient signatures, that might also include demographic and clinical data, the system can evaluate the proximity of a new record to the existing ones and if the later are annotated, with specific class labels and/or risk groups, an assignment of a clinically useful characterization for the new record can be made. Furthermore, sequential results can produce signatures for a single patient, which will provide info about the clinical trajectory of a patient over time, allowing one to evaluate the speed and severity of transitioning from a healthy to a disease state and to a new state after interventions.

Risk Prediction

In some implementations, a number of categories of algorithms can be available to be used with the features extracted, as described herein. Examples of such algorithms include: Time-to-event approaches (parametric/non-parametric survival analysis), combined with demographic and clinical factors as predictors to time to event approaches (combination of multiple methods), Classification of event/no event probabilities obtained from ML/DL classification methods, combined with demographic and clinical factors as predictors to time to event approaches (combination of multiple methods), and/or Deep learning approaches for event risk prediction including methods that use loss functions to the ones used in traditional statistical models for survival, LSTM, RNN and Transformer models.

Reporting Predictions

In some implementations, the system can provide a digital representation of risk predictions. The system can provide a risk score, for example, on a 100-point range where 0 is no risk and 100 is guaranteed occurrence of a future event, and the corresponding risk of the specific event(s), for a given individual within a pre-specified amount of follow up time (see, e.g., FIG. 9). The system can include corresponding risk curves from validation studies as supporting evidence (see, e.g., FIG. 10). The curves might be stratified based on demographic characteristics, indications for monitoring, clinical characteristics, such as a CHA2DS2-VASc score, or HAS-BLED score, treatment regiment, and/or the like. The system can include corresponding treatment benefit curves as a function of event risk score and other demographic/clinical characteristics based on retrospective or randomized prospective studies, as supportive evidence of treatment benefit. The system can display a visual representation of "record signatures" and measures of proximity to neighborhood records. The system can report of treatment choices (specific interventions, medications, percentages of such information) and outcomes for patients in the vicinity of the record of interest.

Implementations of Clustering Patient Data

Figure 8:
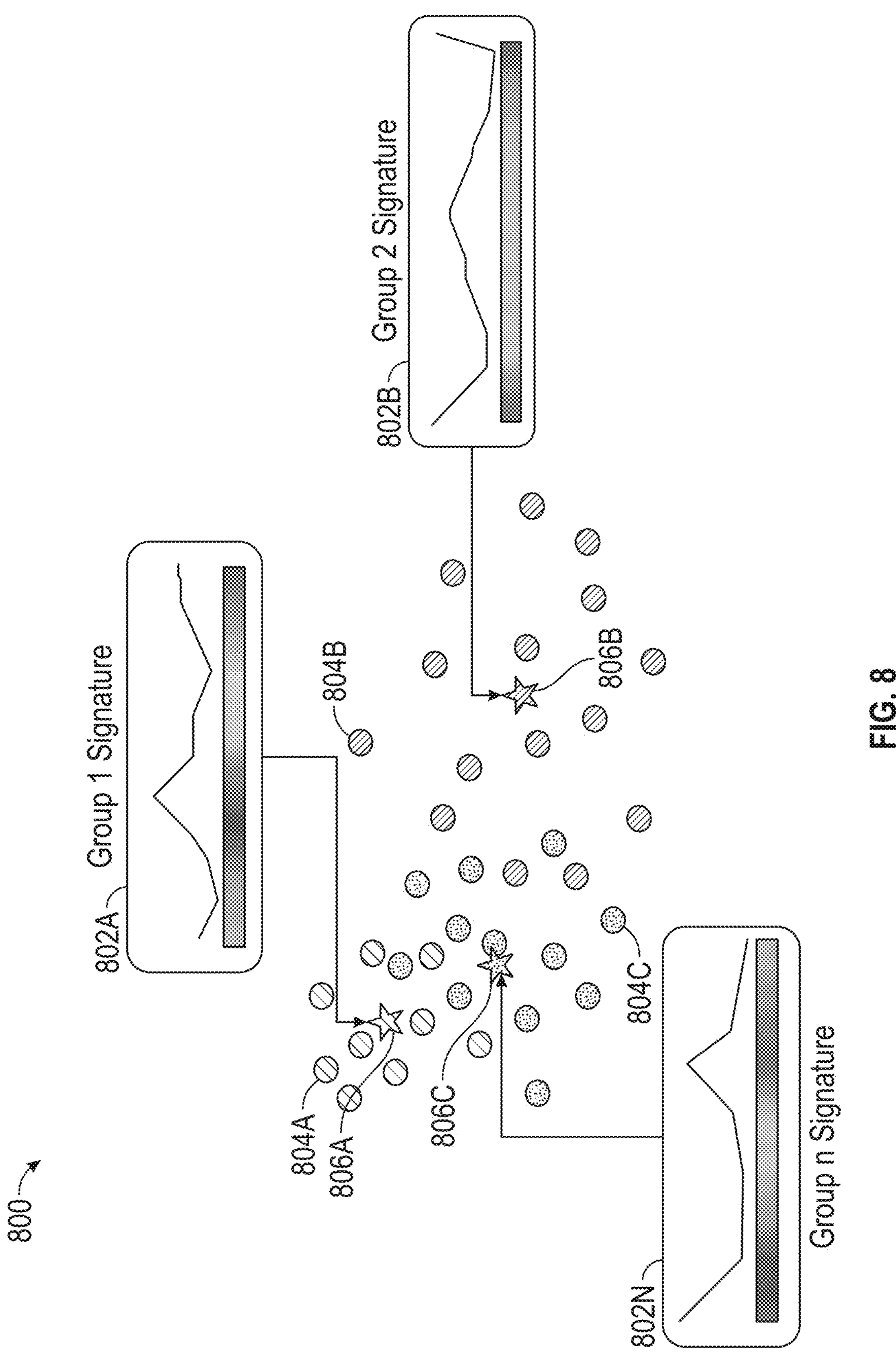
FIG. 8 illustrates an implementation of grouping individual signatures (represented as a projection on a 2D plane) from individuals that may have different progression to an event timeframes and or respond better to a specific intervention.

FIG. 8 illustrates an implementation 800 of grouping individual signatures (represented as a projection on a 2D plane) from individuals that may have different progression to an event timeframe and or respond better to a specific intervention (such as that the signature is indicative of the probability to response to a given intervention). For example, the various group signatures 802A, 802B, 802C can be projected onto a 2D plane as circles 804A, 804B, 804C in various groupings. The stars 806A, 806B, 806C represent the representative signature (centroid) for a group with similar characteristics where the circles represent individual observations that are "closer" in a mathematical distance sense to the specific centroid. Among other dimensionality reduction methods, an encoder can create, from a large amount of data, a reduced dimensionality representation of the information at the bottleneck, such as a 2-dimensional vector. If you would like to reduce the dimensionality to 2 dimensions, then the system can determine predictions into these two dimensions. For example, the 2 dimensions can include two different groups of people, where the first group benefited from the intervention and the second group did not. Then, if the patient falls nearer to the centroid of the group of people that benefited from a treatment, the system can predict that the patient can benefit from a certain type of intervention.

In some embodiments, the system can create clusters from multiple modalities. The system can generate a representation of the signals in a latent space using one or more neural networks (such as deep learning algorithms). These neural networks can be trained to incorporate contrastive loss for assigning distances between signals. Contrastive loss can include training examples that are "close" in value (e.g., measurement vectors that correspond to individuals with similar characteristics and identical or similar clinical outcome) along with other characteristics that are "far" from the reference sample.

In some embodiments, the system can take a sample as a reference and contrasting it with other samples that are "close" and a number of others that are "far". The neural network is trained to generate and apply a function that can calculate a distance matrix between samples. This distant metric is based on a latent representation of each sample, (e.g., a projection into a system of coordinates that places closer elements that are more similar and places elements that are more dissimilar further away).

In some embodiments, the system can apply these latent vectors as the basis in clustering algorithms (e.g., k-means, hierarchical clustering, BIRCH, etc) to create clusters of patients with similar outcomes and establish their representative sample ("centroid"). Advantageously, the system can make a better prediction based on a holistic view of the data (neighborhood of patients samples with similar outcomes), instead of corresponding with any single patient's samples. A new sample can then be clustered using a combination of the latent projections obtained from the contrastive loss-based network and the clustering algorithm. In another implementation, the same latent features can be used to create a classification of outcome classes through the use of a classification neural network. Then, any new observation can be predicted using the trained network.

Figure 9:
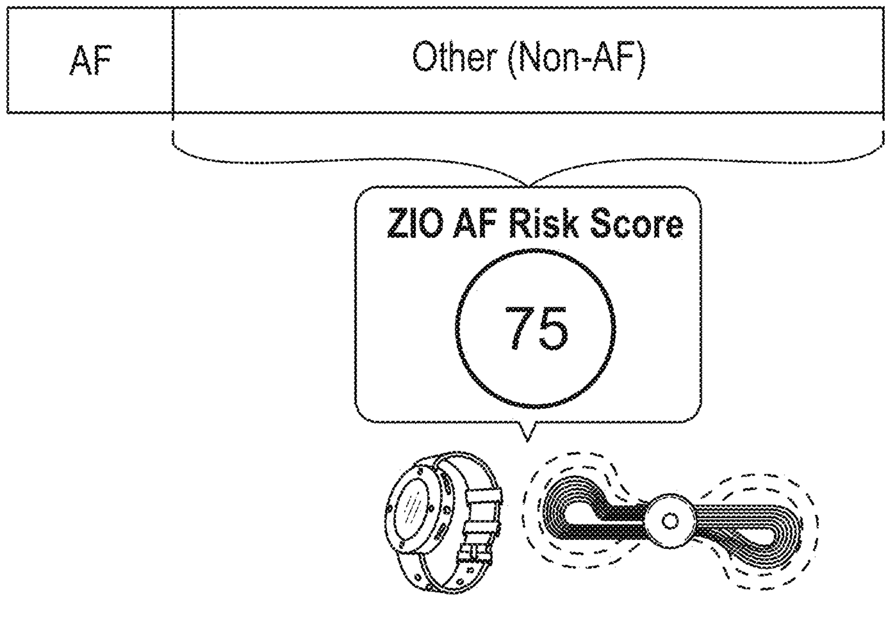
FIG. 9 illustrates schematic of a risk score alert for a patient that did not have an event within a current patch wear time but the record contains markers that indicate high degree of confidence in the onset/detection of AF within a pre-specified follow up period

FIG. 9 illustrates schematic 900 of a risk score alert for a patient that did not have an event within a current patch wear time but the record contains markers that indicate high degree of confidence in the onset/detection of AF within a pre-specified follow up period. The risk score can be a score between 1-100, such as 75, other scores within score ranges, such as between 1-5, 1-10, or other scores, such as a letter grading. The AF portion and the Other (Non-AF) portion can represent a population of people. For example, 80% of the population do not have AF, but 20% do. The risk score can apply to people that do not have AF to help direct monitoring strategy to manage future risk. The risk score can also apply to those that have AF to manage the condition, such as via pharmacological, surgical, or lifestyle interventions. The risk score can apply to the entire population, regardless of whether the patient has or does not have AF, to optimize public health for the population.

Figure 10:
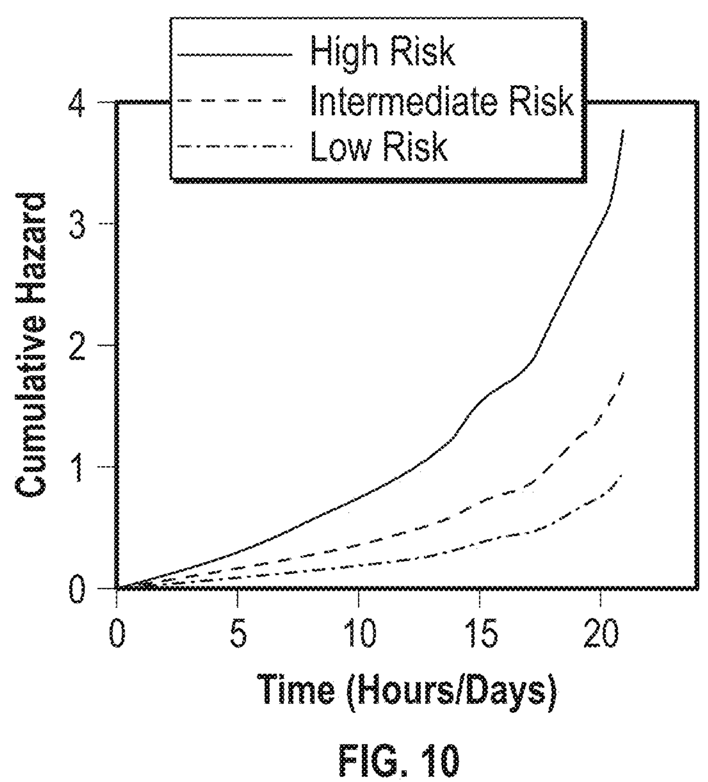
FIG. 10 illustrates a graph according to an implementation of risk curves stratified by demographic or clinical characteristics.

FIG. 10 illustrates a graph 1000 according to an implementation of risk curves stratified by demographic or clinical characteristics. The graph can show risk score curves based on cumulative hazard over time, such as hours/days/years. The same risk score might provide a different probability for an outcome based on such characteristics. For example, the low risk curve may be to provide implications for patients between 30-50 years old. As such, a risk score can have a different meaning for patients of different ages. In some implementations, the risk curves can be stratified by clinical characteristics, such as current measurements of the patient (e.g., blood pressure, PPG). In some implementations, the risk curves can be stratified by past historical health.

Implementations of Reports

Figure 11:
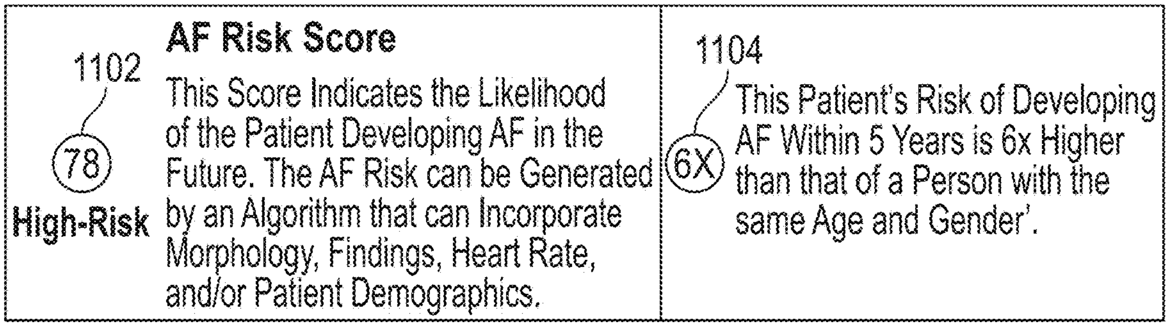
FIG. 11 illustrates an implementation of a report of a patient with no AF identified.
Figure 11:
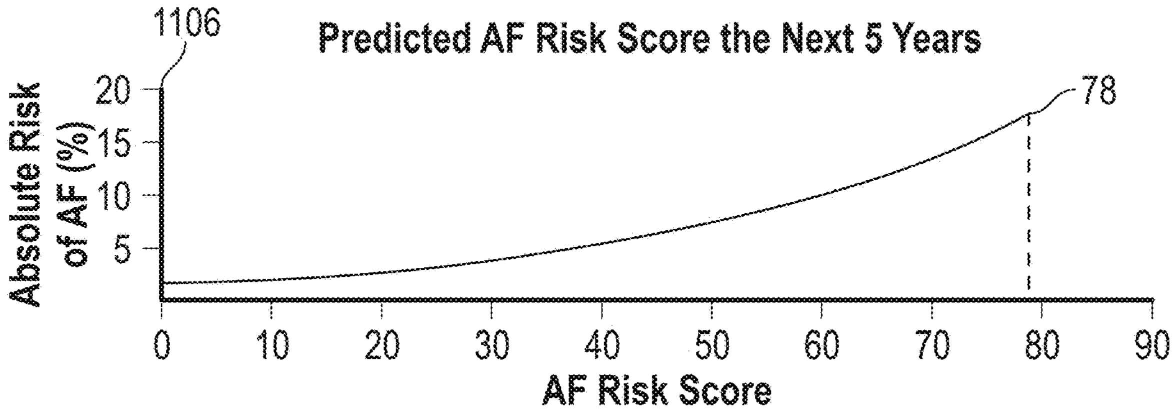
Figure 11:
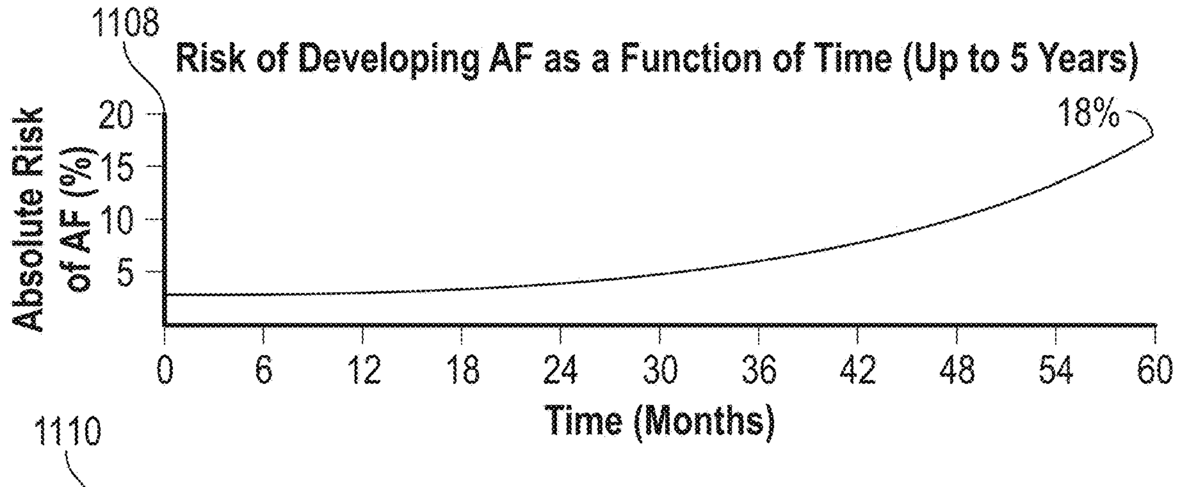

FIG. 11 illustrates an implementation of a report 1100 of a patient with no AF identified. The report can include an indication of an AF Risk Score 1102 that indicates the likelihood of a patient developing AF in the future. The number 78 can represent a high score (and/or displayed in a circle). The report can include an indication of a relative risk 1104. The 6× can represent the relative risk as a fold change for this patient, for example, for a person with the same age and gender characteristics but no abnormal features. The relative risk can be another representation of risk that can be obtained from the model, and/or determined based on morphology, heart rate, demographics, and/or other findings.

In some implementations, the report 1100 can include a graph 1106 of a predicted AF risk over the next five years. In some implementations, the graph can be over a different time period, such as over days, weeks, months, etc. The graph 1106 can display the risk curve as a function of the score (at 5 years). The report 1100 can include another graph 1108 that provides the predicted progression in absolute risk for this person as a function of time. The absolute risk can be displayed as a percentage, such as an absolute risk of 18% at 5 years. The report 1100 can include a table 1110 that provides the risk of onset over time, such as several months, and the AF risk score and/or the progression of risk.

Figure 12B:
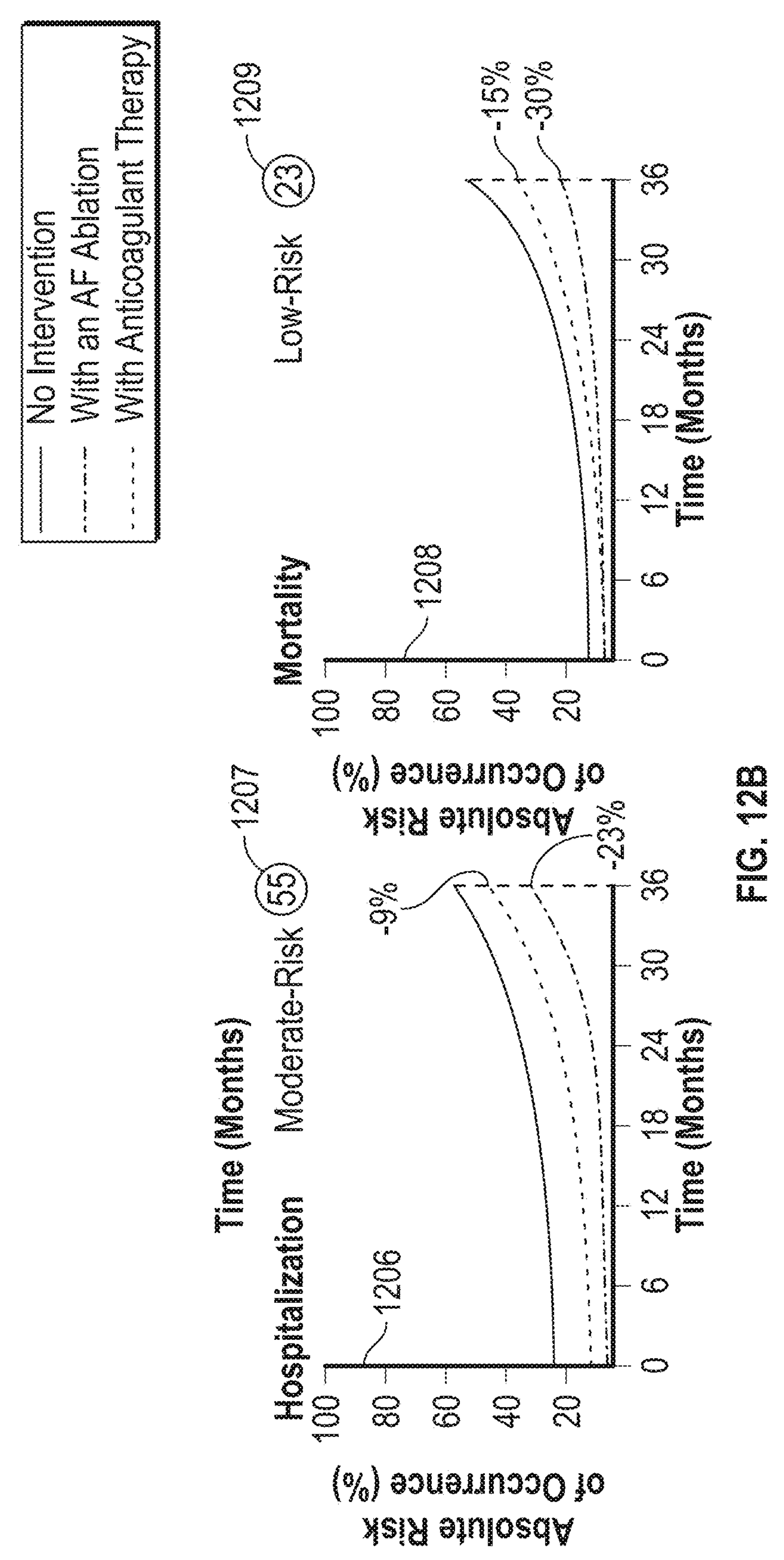

FIGS. 12A and 12B illustrate implementations of a report 1200, 3500 of a patient with AF identified in the recording of the cardiac monitor. The reports 1200, 1250 can indicate a risk of adverse patient outcomes over time. The outcomes can correspond to a risk score that indicates the likelihood of an event occurring within a time period, such as 36 months. The score and/or the risk curves can be generated by a deep learning algorithm that can take into account, among other things, the patient's ECG morphology, findings, heart rate, and/or demographics. The reports 1200, 3500 can include risk curve graphs that represent risks related to outcomes of interest, such as for stroke 1202, heart failure 1204, hospitalization 1206, and/or mortality 1208. Each of the risk curve graphs can include a risk curve for no intervention (solid line), with AF Ablation (first dotted line), and with anticoagulant therapy (second dotted line). For example, the no intervention risk curve can represent a risk as a function of time for a cohort with the same characteristics and no intervention. The risk circles 1203, 1205, 1207, and 1209 can indicate levels of risk, such as high-risk for a score of 78. The risk curves can indicate a reduction of risk based on certain treatment. For example for the stroke curve 1202, a patient's risk can be reduced by 28% with an AF ablation, and 23% with anticoagulant therapy.

In some implementations, system can generate the risk score and/or curves for one or more other physiological signals. For example, the system can generate a curve graph of future risk for stroke, heart failure, cardiovascular hospitalization, structural heart disease (such as left/right ventricular hypertrophy, reduced injection fraction, atrial/mitral regurgitation, stenosis, tricuspid regurgitation), and/or the like.

Example Flow Diagrams

Figure 13A:
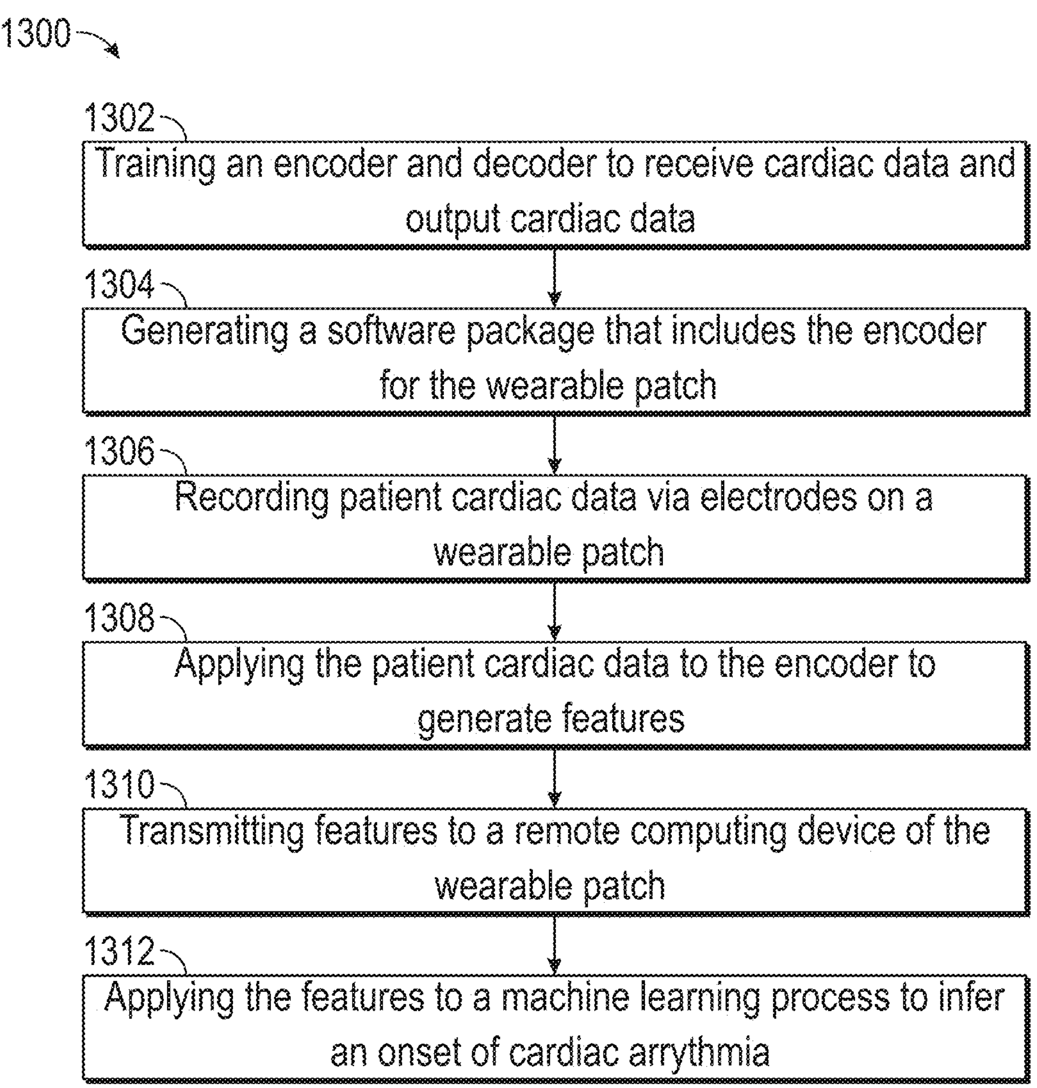
FIG. 13A illustrates an example implementation of a flow diagram for training an encoder and decoder, and applying the encoder on the wearable device to infer an onset of cardiac arrhythmia.

FIG. 13A illustrates an example implementation of a flow diagram 1300 for training an encoder and decoder, and applying the encoder on the wearable device to infer an onset of cardiac arrhythmia. In block 1302, the system can train an encoder and decoder to receive cardiac data and output cardiac data. The encoder can output features of the cardiac data. The encoder and decoder can be trained to output data that represents the inputted cardiac data with sufficient fidelity, such as a threshold level of similarity.

In block 1304, the system can generate a software package that includes the encoder for a wearable patch for the wearable patch to apply the encoder to cardiac data of a new patient. In block 1306, the wearable patch can record patient cardiac data, such as by using electrodes on a wearable patch. In block 1308, the wearable device can apply the patient cardiac data using an encoder to generate features of the patient cardiac data. The encoder can output features such as boundaries, edges, single-line slopes, offset, signal magnitude, and/or the like. The output of the encoder can be of a smaller dimensionality than the data that was inputted into the encoder.

In block 1310, the wearable device can transmit the features that were outputted from the encoder to a remote computing device. Advantageously, the wearable device can have many technical advantages, such as longer battery life, smaller storage requirements, and/or the like, such as the advantages described further herein. In block 1312, the remote computing device can apply the features to a machine learning process to infer an onset of cardiac arrhythmia. The machine learning process can be a separate process than the encoder and the decoder. The machine learning process can be trained separately than the encoder and the decoder, as further described herein.

Figure 13B:
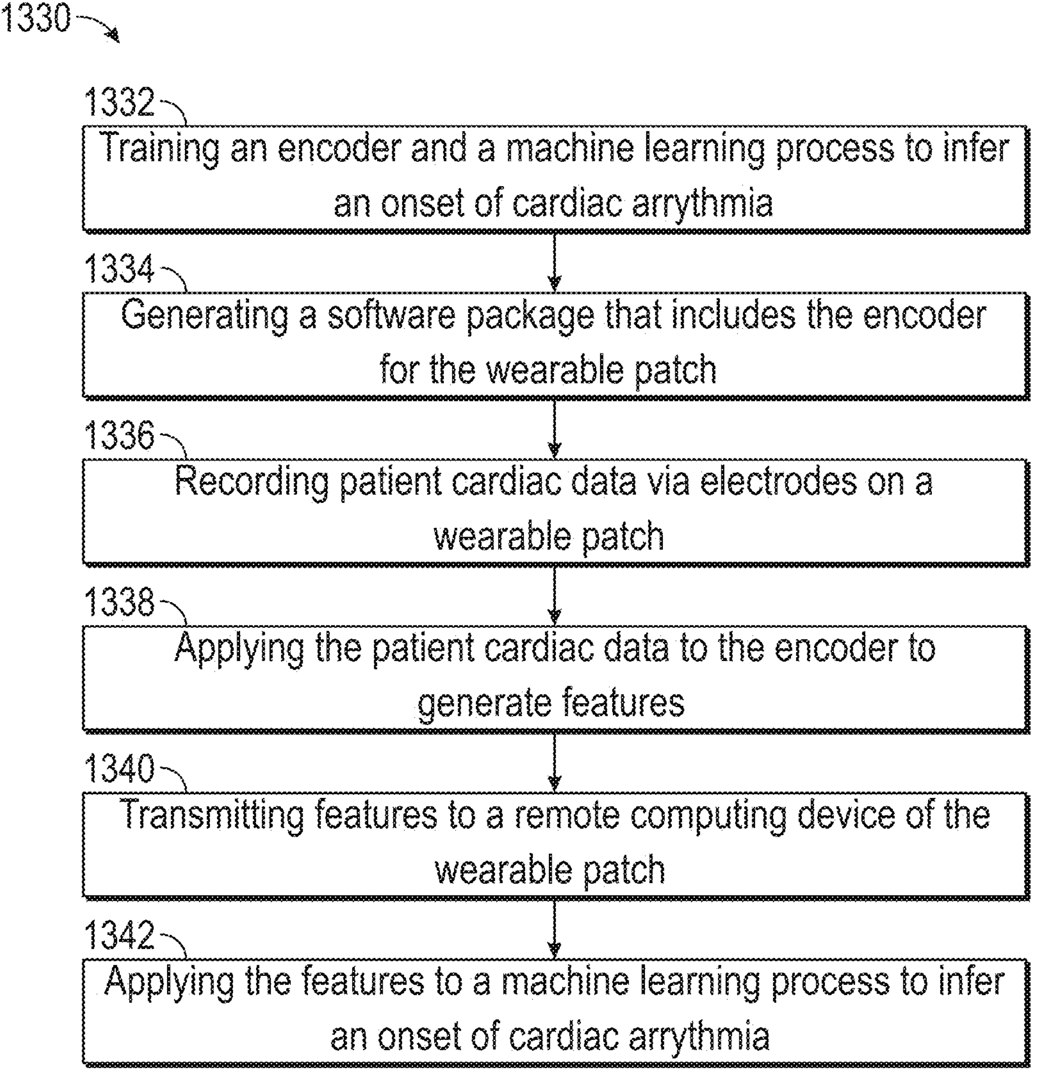
FIG. 13B illustrates an example implementation of a flow diagram for training an encoder and machine learning model, applying the encoder on the wearable device, and applying the machine learning model on a remote computing device to infer an onset of cardiac arrhythmia.

FIG. 13B illustrates an example implementation of a flow diagram 1330 for training an encoder and machine learning model, applying the encoder on the wearable device, and applying the machine learning model on a remote computing device to infer an onset of cardiac arrhythmia. In block 1332, the system can train an encoder and a separate machine learned model to receive cardiac data and output to an inference of an onset of cardiac arrythmia. The training can apply historical patient cardiac data and a status of cardiac arrhythmia for the same patient at a later time, such as a month, five months, a year, or five years later. Advantageously, the encoder can be specifically trained to output features of the cardiac data that are most relevant for inferring the onset of cardiac arrhythmia.

In block 1334, the system can generate a software package that includes the encoder for a wearable patch for the wearable patch to apply the encoder to cardiac data of a new patient, such as block 1304 and/or described further herein. In block 1336, the wearable patch can record patient cardiac data, such as by using electrodes on a wearable patch, such as block 1306 and/or described further herein. In block 1338, the wearable device can apply the patient cardiac data using an encoder to generate features of the patient cardiac data, such as block 1308 and/or described further herein.

In block 1340, the wearable device can transmit the features that were outputted from the encoder to a remote computing device, such as block 1310 and/or described further herein. In block 1342, the remote computing device can apply the features to the machine learning process to infer an onset of cardiac arrhythmia. The machine learning process is trained with the encoder. However, the encoder is applied on the wearable device, and the machine learning process is applied on the remote computing device.

Figure 13C:
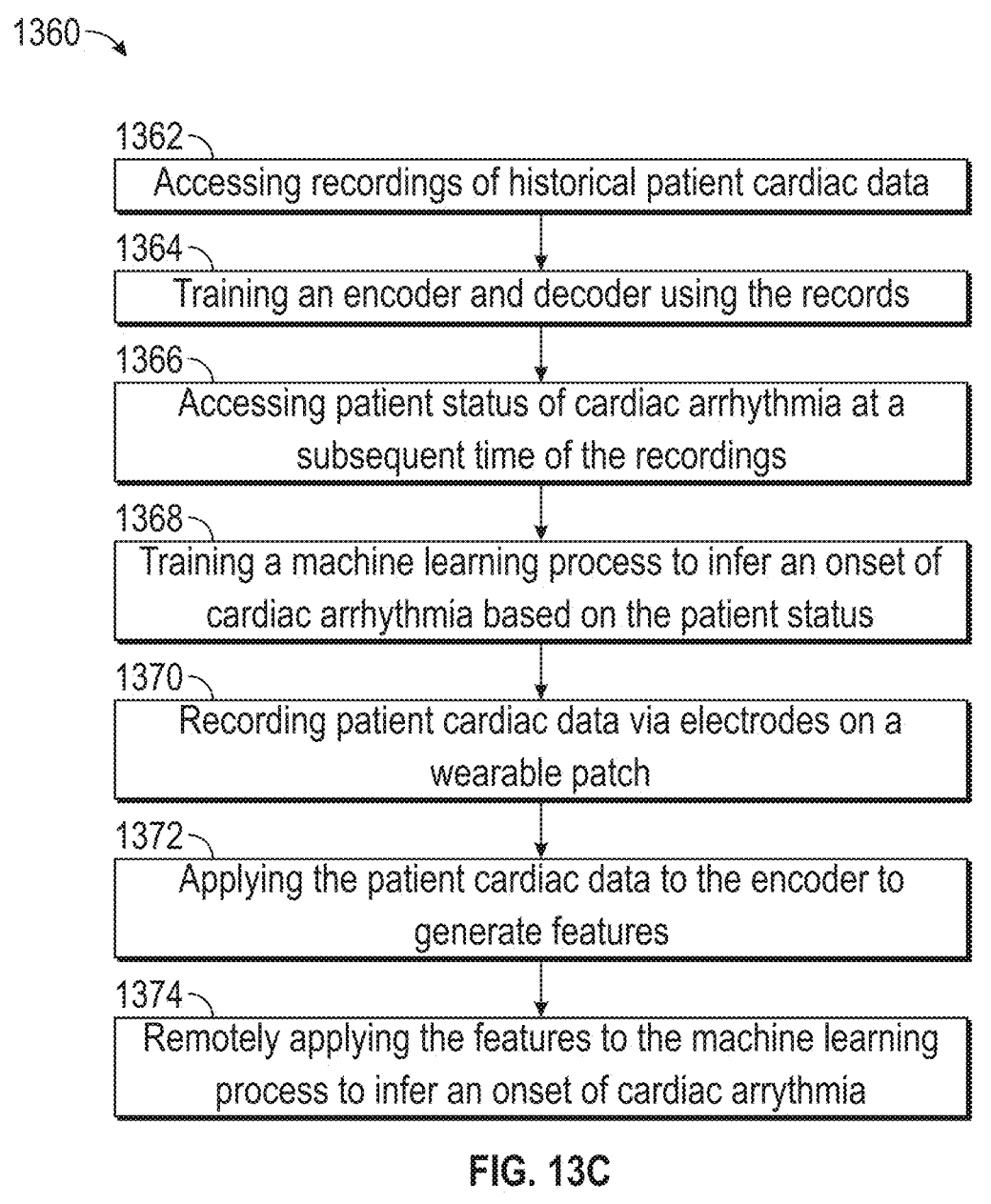

FIG. 13C illustrates an example implementation of a flow diagram 1360 for training an encoder, decoder, and machine learning model using historical patient cardiac data to infer an onset of cardiac arrhythmia. In block 1362, the system can access records of historical patient cardiac data. For example, the historical patient cardiac data can include data of hundreds or thousands of past patients and corresponding cardiac data in the past. In block 1364, the system can train an encoder and decoder using the historical patient cardiac data, such as block 1302 and/or described further herein.

In block 1366, the system can access patient status of cardiac arrhythmia at a subsequent time of the cardiac data measurement recordings. For example, the historical patient cardiac data of a patient can be five years old, where the data does not indicate cardiac arrhythmia five years ago. However, the status of the patient five years later was that the patient later acquired cardiac arrhythmia.

In block 1368, the system can train a machine learning process to infer an onset of cardiac arrhythmia based on the patient status. The data that can be used can include the features that are outputted by the trained encoder that used the historical patient cardiac data. Thus, the status and the historical patient cardiac data can correspond to the same individual.

In block 1370, the wearable patch can record patient cardiac data, such as by using electrodes on a wearable patch, such as block 1306 and/or described further herein. In block 1372, the wearable device can apply the patient cardiac data using an encoder to generate features of the patient cardiac data, such as block 1308 and/or described further herein In block 1374, the remote computing device can apply the features to a machine learning process to infer an onset of cardiac arrhythmia, such as block 1312 and/or described further herein.

Computing Systems and Methods

Figure 14:
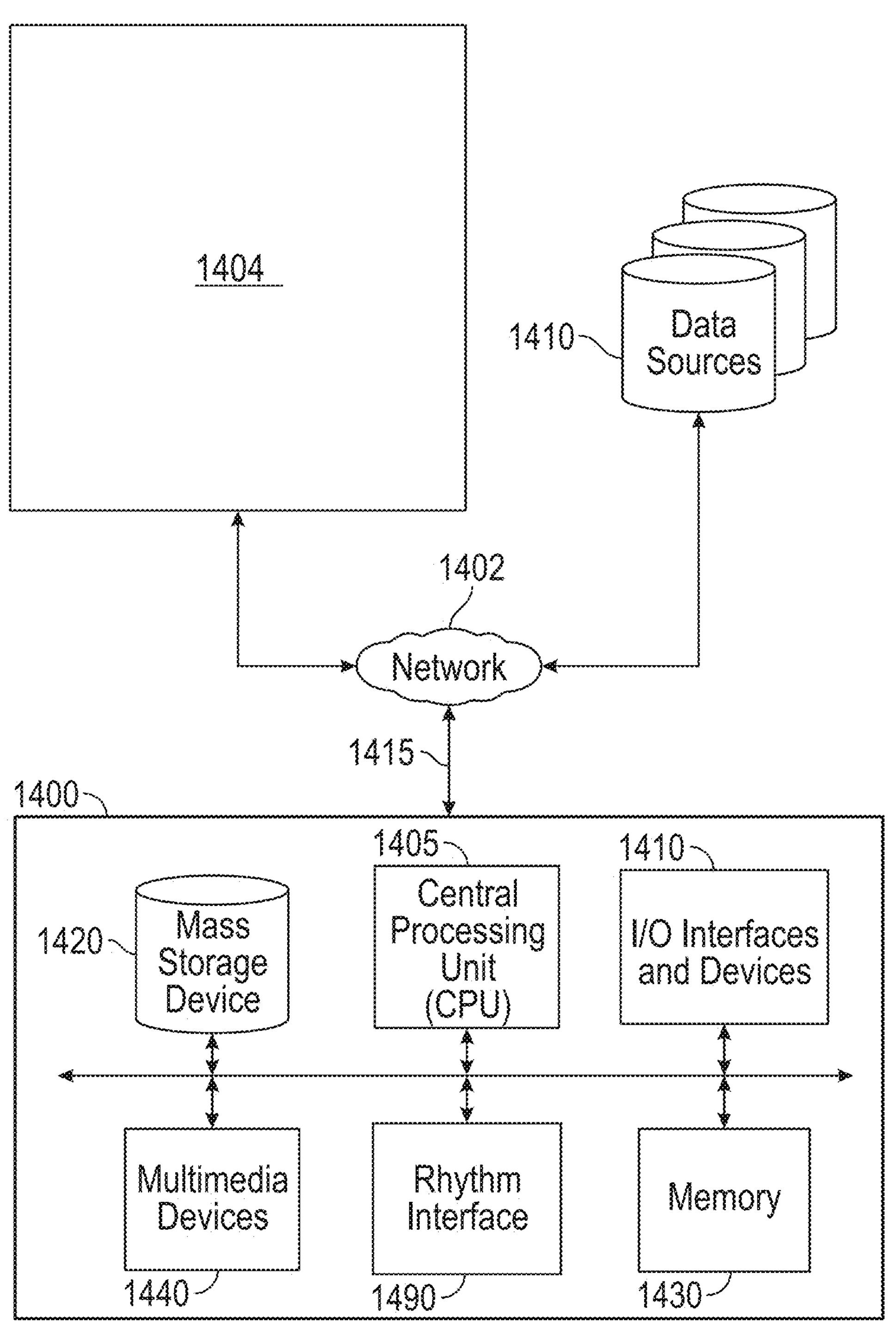
FIG. 14 is a schematic diagram of an implementation of a computer network system.

In some implementations, the systems, tools and methods of using same described above enable interactivity and data collection performed by a computing system 1400. FIG. 14 is a block diagram showing an implementation in which the computing system 1400 is in communication with a network 14002 and various external computing systems 1404, such as a wearable system 14005, a gateway device 13006, which are also in communication with the network 14002. The computing system 1400 may be used to implement systems and methods described herein. While the external system 1404 are shown as grouped it is recognized that each of the systems may be external from each other and/or remotely located.

Computing Systems and Methods

Figure 15:
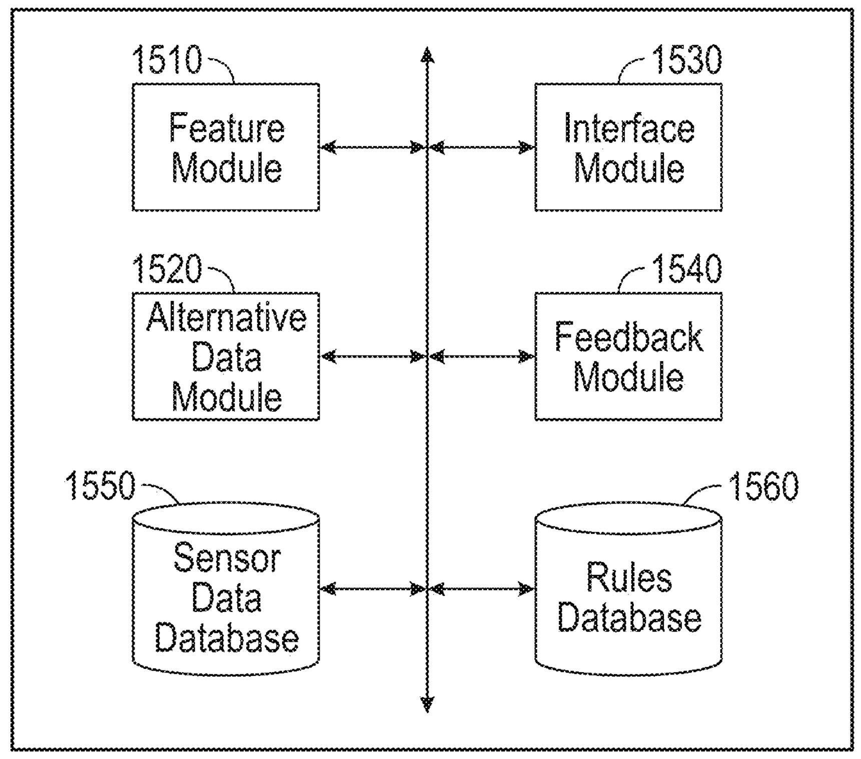
FIG. 15 is a schematic diagram of an implementation of a programming and distribution module.

In some implementations, the systems, tools and methods of using same described above enable interactivity and data collection performed by a computing system 1400. FIG. 15 is a block diagram showing an implementation in which the computing system 1400 is in communication with a network 14002 and various external computing systems 1404, such as a wearable system 14005, a gateway device 13006, which are also in communication with the network 14002. The computing system 1400 may be used to implement systems and methods described herein. While the external system 1404 are shown as grouped it is recognized that each of the systems may be external from each other and/or remotely located.

In some implementations, the computing system 1400 includes one or more computing devices, for example, a server, a laptop computer, a mobile device (for example, smart phone, smart watch, tablet, personal digital assistant), a kiosk, automobile console, or a media player, for example. In one implementation, the computing device 1400 includes one or more central processing units (CPUs) 1405, which may each include a conventional or proprietary microprocessor. The computing device 1400 further includes one or more memory 1430, such as random access memory (RAM) for temporary storage of information, one or more read only memory (ROM) for permanent storage of information, and one or more mass storage device 1420, such as a hard drive, diskette, solid state drive, or optical media storage device. In certain implementations, the processing device, cloud server, server or gateway device, may be implemented as a computing system 1300. In one implementation, the modules of the computing system 1400 are connected to the computer using a standard based bus system. In different implementations, the standard based bus system could be implemented in Peripheral Component Interconnect (PCI), Microchannel, Small Computer computing system Interface (SCSI), Industrial Standard Architecture (ISA) and Extended ISA (EISA) architectures, for example. In addition, the functionality provided for in the components and modules of computing device 1400 may be combined into fewer components and modules or further separated into additional components and modules.

The computing device 1400 may be controlled and coordinated by operating system software, for example, iOS, Windows XP, Windows Vista, Windows 7, Windows 8, Windows 10, Windows Server, Embedded Windows, Unix, Linux, Ubuntu Linux, SunOS, Solaris, Blackberry OS, Android, or other operating systems. In Macintosh systems, the operating system may be any available operating system, such as MAC OS X. In other implementations, the computing device 1400 may be controlled by a proprietary operating system. Conventional operating systems control and schedule computer processes for execution, perform memory management, provide file system, networking, I/O services, and provide a user interface, such as a graphical user interface (GUI), among other things.

The exemplary computing device 1400 may include one or more I/O interfaces and devices 1410, for example, a touchpad or touchscreen, but could also include a keyboard, mouse, and printer. In one implementation, the I/O interfaces and devices 1410 include one or more display devices (such as a touchscreen or monitor) that allow visual presentation of data to a user. More particularly, a display device may provide for the presentation of GUIs, application software data, and multimedia presentations, for example. The computing system 1400 may also include one or more multimedia devices 1440, such as cameras, speakers, video cards, graphics accelerators, and microphones, for example.

The I/O interfaces and devices 1410, in one implementation of the computing system and application tools, may provide a communication interface to various external devices. In one implementation, the computing device 1400 is electronically coupled to a network 14002, which comprises one or more of a local area network, a wide area network, and/or the Internet, for example, via a wired, wireless, or combination of wired and wireless, communication link 1415. The network 14002 can communicate with various sensors, computing devices, and/or other electronic devices via wired or wireless communication links.

In some implementations, the filter criteria, signals and data are processed by rhythm inference module an application tool according to the methods and systems described herein, may be provided to the computing system 1400 over the network 14002 from one or more data sources 1410. The data sources may include one or more internal and/or external databases, data sources, and physical data stores. The data sources 1410, external computing systems 1404 and the rhythm interface module 1490 may include databases for storing data (for example, feature data, raw signal data, patient data) according to the systems and methods described above, databases for storing data that has been processed (for example, data to be transmitted to the sensor, data to be sent to the clinician) according to the systems and methods described above. In one implementation of FIG. 6, the sensor data 1550 may, in some implementations, store data received from the sensor, received from the clinician, and so forth. The Rules Database 1560 may, in some implementations, store data (for example, instructions, preferences, profile) that establish parameters for the thresholds for analyzing the feature data. In some implementations, one or more of the databases or data sources may be implemented using a relational database, such as Sybase, Oracle, CodeBase, MySQL, SQLite, and Microsoft® SQL Server, and other types of databases such as, for example, a flat file database, an entity-relationship database, and object-oriented database, NoSQL database, and/or a record-based database.

The computing system, in one implementation, includes a rhythm interface module 1490 that may be stored in the mass storage device 1420 as executable software codes that are executed by the CPU 1405. The rhythm interface module 1490 may have a Feature Module 1510, an Alternate Data Module 1520, an Inference Module 1530, a Feedback Module 1540, a Sensor Data Database 1550, and a Rules Database 1560. These modules may include by way of example, components, such as software components, object-oriented software components, subroutines, segments of program code, drivers, firmware, microcode, circuitry, data, databases, data structures, tables, arrays, and variables. These modules are also configured to perform the processes disclosed herein.

In some implementations, the various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry.

What is claimed is:

1. A computing system for inferring an onset of cardiac arrythmia of a user, the computing system comprising:

a receiver configured to receive cardiac signals of a user detected by a sensor applied to the user; and a hardware processor configured to apply the cardiac signals to a first machine learning model, wherein the first machine learning model is configured to infer an onset of cardiac arrhythmia based on the cardiac signals of the user, and wherein the first machine learning model is generated using a machine learning training process comprising:

accessing historical patient data for a plurality of patients, wherein the historical patient data comprises historical cardiac signal data for the plurality of patients;

accessing a status of cardiac arrhythmia for each of the plurality of patients, wherein the status of cardiac arrhythmia for the plurality of patients is determined subsequent to a time when the historical cardiac signal data were recorded for each patient of the plurality of patients; and training the first machine learning model based at least in part on the historical cardiac signal data for the plurality of patients and the status of cardiac arrhythmia of each patient of the plurality of patients to infer an onset of cardiac arrhythmia, wherein the user is different than the plurality of patients, wherein the hardware processor is further configured to apply the cardiac signals of the user to a second machine learning model, wherein the second machine learning model is trained to remove artifacts from the cardiac signals of the user to obtain filtered cardiac signals, and wherein applying the cardiac signals to the first machine learning model comprises applying the filtered cardiac signals as input to the first machine learning model.

2. The computing system of claim 1, wherein the second machine learning model is further trained to reduce noise from the cardiac signals of the user to obtain the filtered cardiac signals.

3. The computing system of claim 1, wherein inferring the onset of cardiac arrhythmia comprises determining a probability of an occurrence of cardiac arrythmia at a later time.

4. The computing system of claim 1, wherein at least a portion of the historical patient data does not indicate cardiac arrhythmia at a time of recording the historical cardiac signal data.

5. The computing system of claim 1, wherein the first machine learning model is further configured to process photoplethysmography (PPG) data, heartbeat data, or heart rate acceleration data to infer the onset of cardiac arrythmia.

6. The computing system of claim 1, wherein the cardiac arrhythmia comprises at least one of: ventricular tachycardia, supraventricular tachycardia, ectopy, or ventricular fibrillation.

7. The computing system of claim 1, wherein the historical patient data further comprises the status of cardiac arrhythmia for each of the plurality of patients.

8. The computing system of claim 1, wherein the sensor comprises an electrode.

9. A method of training a machine learning model to infer an onset of cardiac arrhythmia, the method comprising:

by a hardware processor configured to execute computer-implemented instructions:

accessing historical patient data for a plurality of patients, wherein the historical patient data comprises historical cardiac signal data for the plurality of patients, wherein the historical cardiac signal data comprises cardiac signals, and wherein at least a portion of the historical cardiac signal data does not indicate cardiac arrhythmia at a time of recording the cardiac signals;

accessing a status of cardiac arrhythmia for each patient of the plurality of patients, wherein the status of cardiac arrhythmia for each of the plurality of patients is determined subsequent to a time when the cardiac signals were recorded for the patient;

training a first machine learning model based on the historical cardiac signal data for the plurality of patients and the status of cardiac arrhythmia of each patient of the plurality of patients to infer an onset of cardiac arrhythmia of a user, wherein the user is not included in the plurality of patients;

applying cardiac signals of the user to a second machine learning model that is trained to remove artifacts from the cardiac signals of the user to obtain filtered cardiac signals; and applying the filtered cardiac signals to the first machine learning model to infer the onset of cardiac arrhythmia of the user.

10. The method of claim 9, wherein the second machine learning model is further trained to reduce noise from the cardiac signals of the user.

11. The method of claim 9, wherein inferring the onset of cardiac arrhythmia comprises determining a probability of an occurrence of cardiac arrythmia within a particular time period.

12. The method of claim 9, wherein training the first machine learning model further comprises training the first machine learning model to infer an occurrence of hospitalization, heart failure onset, onset of a stroke, or death of the user.

13. The method of claim 9, further comprising training a second machine learning model to infer an occurrence of hospitalization, heart failure onset, an onset of a stroke, or death of the user, wherein an input to the second machine learning model comprises cardiac signals of a longer duration than cardiac signals provided to the first machine learning model.

14. The method of claim 9, further comprising determining an atrial fibrillation burden from cardiac signals of the user, wherein the atrial fibrillation burden comprises an amount of time spent in atrial fibrillation by the user during a period of time.

15. A non-transitory computer storage medium storing computer-executable instructions that, when executed by a processor, cause the processor to perform operations comprising:

accessing historical patient data for a plurality of patients, wherein the historical patient data comprises historical cardiac signal data for the plurality of patients, wherein the historical cardiac signal data comprises cardiac signals, and wherein at least a portion of the historical cardiac signal data does not indicate cardiac arrhythmia at a time of recording the cardiac signals;

accessing a status of cardiac arrhythmia for each patient of the plurality of patients, wherein the status of cardiac arrhythmia for each of the plurality of patients is determined subsequent to a time when the cardiac signals were recorded for the patient;

training a first machine learning model based on the historical cardiac signal data for the plurality of patients and the status of cardiac arrhythmia of each patient to infer an onset of cardiac arrhythmia of a user, wherein the user is not included in the plurality of patients;

applying cardiac signals of the user to a second machine learning model that is trained to remove artifacts or reduce noise from the cardiac signals of the user to obtain filtered cardiac signals; and applying the filtered cardiac signals to the first machine learning model to infer the onset of cardiac arrhythmia of the user.

* * * * *